(12) United States Patent
Hashizume et al.

(10) Patent No.: US 6,294,567 B1
(45) Date of Patent: Sep. 25, 2001

(54) PYRAZOLINONE DERIVATIVES

(75) Inventors: Masaya Hashizume, Toyonaka; Norio Kimura, Minoo; Noboru Yamamoto, Kawanishi, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/673,888

(22) PCT Filed: Apr. 22, 1999

(86) PCT No.: PCT/JP99/02147

§ 371 Date: Oct. 23, 2000

§ 102(e) Date: Oct. 23, 2000

(87) PCT Pub. No.: WO99/54307

PCT Pub. Date: Oct. 28, 1999

(30) Foreign Application Priority Data

| Apr. 23, 1998 | (JP) | 10-113290 |
| Oct. 5, 1998 | (JP) | 10-282487 |
| Nov. 30, 1998 | (JP) | 10-339441 |

(51) Int. Cl.[7] ..................... A61K 31/4152; C07D 231/52
(52) U.S. Cl. ...................... 514/404; 548/368.7
(58) Field of Search ................. 548/368.7; 514/404

(56) References Cited

U.S. PATENT DOCUMENTS

| 5,869,684 | 2/1999 | Hashizume et al. |
| 5,869,687 | 2/1999 | Sato et al. |

FOREIGN PATENT DOCUMENTS

| 10316733 | 5/1989 | (EP) |
| 1160968 | 6/1989 | (JP) |
| 8208621 | 8/1996 | (JP) |
| 8301867 | 8/1996 | (JP) |
| 8301867 | 11/1996 | (JP) |
| 9636229 | 12/1996 | (WO) |
| 9700612 | 1/1997 | (WO) |
| 9823155 | 6/1998 | (WO) |

OTHER PUBLICATIONS

Martin Scobie, et al. "A New Strategy for the Synthesis of Cinnoline Derivatives" *J. Chem. Soc. Commun.*, 1993 pp. 1756–1757.

Manuel A. Martinez "Synthesis of O–Alkyl Carbonochloridothioates" *Synthesis*, 1986 pp. 760–761.

Geiner Eckert, et al. "Triphosgene, a Crystalline Phosgene Substitute" *Angew. Chem. Int. Ed. Engl.*, 1987 vol. 26 pp. 894–895.

Harry Tilles "Thiolcarbamates. Prepartion and Molar Refrations[1]" *J. Am. Chem. Soc.*, 1959 vol. 81 pp. 714–727.

J. H. Saunders et al. "The Vapor Phase Reaction between Phosgene and Alcohols" *J. Am. Chem.*, 1951 vol. 73 pp. 3796–3797.

*Organic Syntheses*, vol. I pp. 147.

*Primary Examiner*—Robert W. Ramsuer
(74) *Attorney, Agent, or Firm*—Birch, Stewart, Kolasch & Birch, LLP

(57) ABSTRACT

The pyrazolinone derivatives represented by the formula [I]:

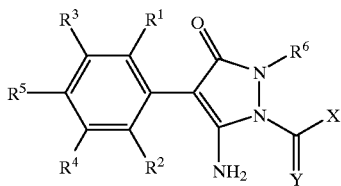

[wherein $R^1$, $R^2$, $R^3$, $R^4$ and $R^5$ may be identical or different and represent independently a hydrogen atom, a halogen atom, an alkyl group, a haloalkyl group, an alkoxyl group, etc.; $R^6$ represents an optionally substituted alkyl group, etc.; X represents an optionally substituted alkyl group, etc,; and Y represents an oxygen atom or a sulfur atom] are provided.

25 Claims, No Drawings

PYRAZOLINONE DERIVATIVES

This application is the national phase under 35 U.S.C. §371 of PCT International Application No. PCT/JP99/02147 which has an International filing date of Apr. 22, 1999, which designated the United States of America.

TECHNICAL FIELD

The present invention relates to the pyrazolinone derivatives, their uses and intermediate products.

BACKGROUND ART

The present invention aims at providing the compounds having an excellent plant disease controlling agent.

DETAILED DESCRIPTION OF THE INVENTION

As a result of extensive studies on the subject matter, the present inventors found that the pyrazolinone derivatives represented by the following formula [1] have an excellent controlling effect against plant diseases, and attained the present invention on the basis of this finding.

The present invention provides the pyrazolinone derivatives (hereinafter referred to as the present compounds) represented by the formula [I]:

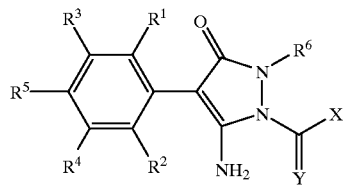

[wherein $R^1$, $R^2$, $R^3$, $R^4$ and $R^5$ may be identical or different and represent independently an hydrogen atom, a halogen atom, an alkyl group, a haloalkyl group, an alkoxy group, an alkoxyalkyl group, an alkoxyalkoxy group, a haloalkoxy group, an alkylthio group, a haloalkylthio group, a cyano group, a nitro group, an optionally substituted phenyl group or an optionally substituted phenoxyl group, or adjacent two of $R^1$, $R^2$, $R^3$, $R^4$ and $R^5$ are combined at the ends to represent a group of the formula CH=CH—CH=CH, a methylenedioxy group which may be substituted with a halogen atom, or an alkylene group which may contain one oxygen atom and may be substituted with an alkyl group;

$R^6$ represents an optionally substituted alkyl group, an optionally substituted alkenyl group, an optionally substituted alkynyl group, an optionally substituted phenyl group, or an optionally substituted alicyclic hydrocarbon group;

X represents an optionally substituted alkyl group, an optionally substituted alkenyl group, an optionally substituted alkynyl group, an optionally substituted phenyl group, an optionally substituted group, an optionally substituted alkenyloxy group, an optionally substituted alkynyloxy group, an optionally substituted phenoxyl group, an optionally substituted alkylthio group, an optionally substituted alkenylthio group, an optionally substituted alkynylthio group, an optionally substituted phenylthio group, or an optionally substituted alicyclic hydrocarbon group; and Y represents an oxygen atom or a sulfur atom] and the plant disease controlling agents containing the present compound as an active ingredient.

The present invention further provides the pyrazolinone compounds represented by the following formula [II] which are useful as the intermediates for the preparation of the present compounds (these pyrazolinone compounds being hereinafter referred to as intermediates A):

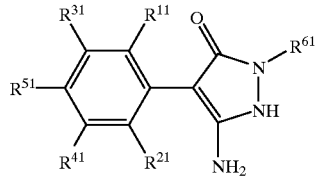

[wherein $R^{11}$, $R^{21}$, $R^{31}$, $R^{41}$ and $R^{51}$ may be identical or different and represent independently a hydrogen atom, a halogen atom, an alkyl group, a haloalkyl group, an alkoxy group, an alkoxyalkyl group, an alkoxyalkoxy group, a haloalkoxy group, an alkylthio group, a haloalkylthio group, a cyano group, a nitro group, an optionally substituted phenyl group or an optionally substituted phenoxyl group; or adjacent two of $R^{11}$, $R^{21}$, $R^{31}$, $R^{41}$ and $R^{51}$ are combined at the ends to represent a group of the formula CH=CH—CH=CH, a methylenedioxy group which may be substituted with a halogen atom, or an alkylene group which may contain one oxygen atom and may be substituted with an alkyl group; and $R^{61}$ represents an optionally substituted alkyl group, an optionally substituted alkenyl group, an optionally substituted alkynyl group, an optionally substituted phenyl group or an optionally substituted alicyclic hydrocarbon group]

and the pyrazolinone compounds represented by the formula [III] which are also useful as the intermediates for the preparation of the present compounds (these pyrazolinone compounds being hereinafter referred to as intermediates B):

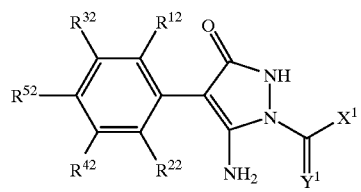

[wherein $R^{12}$, $R^{22}$, $R^{32}$, $R^{42}$ and $R^{52}$ may be identical or different and represent independently a hydrogen atom, a halogen atom, an alkyl group, a haloalkyl group, an alkoxy group, an alkoxyalkyl group, an alkoxyalkoxy group, a haloalkoxy group, an alkylthio group, a haloalkylthio group, a cyano group, a nitro group, an optionally substituted phenyl group or an optionally substituted phenoxyl group, or adjacent two of $R^{12}$, $R^{22}$, $R^{32}$, $R^{42}$ and $R^{52}$ are combined at the ends and represent a group of the formula CH=CH—CH=CH, a methylenedioxy group which may be substituted with a halogen atom, or an alkylene group which may contain one oxygen atom and may be substituted with an alkyl group;

$X^1$ represents an optionally substituted alkyl group, an optionally substituted alkenyl group, an optionally substituted alkynyl group, an optionally substituted phenyl group, an optionally substituted alkoxy group, an optionally substituted alkenyloxy group, an optionally substituted alkynyloxy group, an optionally substituted phenoxyl group, an optionally substituted alkylthio group, an optionally substituted alkenylthio group, an optionally substituted alkynylthio group, an optionally substituted phenylthio group, or an optionally substituted alicyclic hydrocarbon group; and $Y^1$ represents an oxygen atom or a sulfur atom].

MODES FOR CARRYING OUT THE INVENTION

In the present invention, the halogen atoms represented by $R^1$, $R^2$, $R^3$, $R^4$, $R^5$, $R^{11}$, $R^{21}$, $R^{31}$, $R^{41}$, $R^{51}$, $R^{12}$, $R^{22}$, $R^{32}$, $R^{42}$ and $R^{52}$ in the formulae [I] to [III] include fluorine, chlorine, bromine and iodine.

The alkyl groups include C1–C5 alkyl groups such as methyl, ethyl, n-propyl, isopropyl, tert-butyl and n-pentyl.

The haloalkyl groups include C1–C5 haloalkyl groups such as trifluoromethyl, tetrafluoroethyl and heptafluoropropyl.

The alkoxy groups include C1–C5 alkoxy groups such as methoxy, ethoxy, normal propyloxy, isopropyloxy, n-butoxy and n-pentyloxy.

The alkoxyalkyl groups include C1–C3 alkoxy C1–C3 alkyl groups such as methoxymethyl, methoxyethyl, methoxypropyl, ethoxymethyl, ethoxyethyl and ethoxypropyl.

The alkoxyalkoxy groups include C1–C3 alkoxy C1–C3 alkoxy groups such as methoxymethoxy, methoxyethoxy, methoxypropoxy, ethoxymethoxy, ethoxyethoxy and ethoxypropoxy.

The haloalkoxy groups include C1–C5 haloalkoxy groups such as trifluoromethoxy, difluoromethoxy and tetrafluoroethoxy.

The alkylthio groups include C1–C5 alkylthio groups such as methylthio, ethylthio, n-propylthio, n-butylthio and n-pentylthio.

The haloalkylthio groups include C1–C5 haloalkylthio groups such as trifluoromethylthio.

The optionally substituted phenyl and phenoxyl groups include those which may be substituted with at least one group selected from halogen atoms, C1–C5 alkyl groups, C1–C5 alkoxy groups, C1–C5 alkylthio groups, C1–C5 haloalkyl groups, C1–C5 haloalkoxy groups, C1–C5 haloalkylthio groups and cyano groups.

Examples of the above-mentioned substituents are shown below:

Halogen atoms: fluorine, chlorine, bromine and iodine;

C1–C5 alkyl groups: methyl, ethyl, n-propyl, isopropyl, n-butyl and n-pentyl;

C1–C5 alkoxy groups: methoxy and ethoxy;

C1–C5 alkylthio groups: methylthio and ethylthio;

C1–C5 haloalkyl groups, preferably C1–C2 haloalkyl groups: trifluoromethyl;

C1–C5 haloalkoxy groups, preferably C1–C2 haloalkoxy groups: trifluoromethoxy and difluoromethoxy;

C1–C5 haloalkylthio groups, preferably C1–C2 haloalkylthio groups: trifluoromethylthio; and Cyano groups.

Referring to the above R's, adjacent two of $R^1$ to $R^5$, $R^{11}$ to $R^{51}$, and $R^{12}$ to $R^{53}$ may be combined at the ends to form a methylenedioxy group which may be substituted with a halogen atom, such as difluoromethylenedioxy, or an alkylene group (such as C1–C6 alkylene group) which may contain an oxygen atom and may be substituted with an alkyl group (e.g. C1–C4 alkyl group), such as trimethylene, tetramethylene, a group of the formula $OCH_2CH_2$ or a group of the formula $OCH_2CH(CH_3)$.

In the present compounds in view of the controlling effect against plant diseases, it is desirable that 1 to 3 substituents selected from $R^1$ to $R^5$ is a halogen atom (especially chlorine), a haloalkyl group (especially trifluoromethyl) or an alkyl group (especially methyl), and the remainder of the substituents are a hydrogen atom. In view of the efficacy against Botrytis cinerea, it is desirable that $R^3$, $R^4$ and $R^5$ are a hydrogen atom.

Examples of the optionally substituted alkyl groups represented by $R^6$ and $R^{61}$ in the present invention include the following:

C1–C10 alkyl groups such as ethyl, propyl, isopropyl, butyl, isobutyl, sec-butyl, tert-butyl, 1-methylbutyl and 1-ethylpropyl;

C1–C10 haloalkyl groups such as 1-methyl-2,2,2-trifluoroethyl and 1-methyl-3-chloropropyl;

C1–C5 alkoxy C1–C5 alkyl groups such as 2-methoxyethyl;

C1–C5 alkylthio C1–C5 alkyl groups such as 2-methylthioethyl;

C1–C5 haloalkoxy C1–C5 alkyl groups such as 1-methyl-(2,2,2-trifluoroethoxy)ethyl;

C1–C5 haloalkoxy C1–C5 haloalkyl groups;

C1–C5 haloalkylthio C1–C5 alkyl groups such as 1-methyl-(2,2,2-trifluoroethylthio)ethyl;

C1–C5 haloalkylthio C1–C5 haloalkyl groups;

Cyano C1–C5 alkyl groups such as 1-cyanoethyl;

Cyano C1–C5 haloalkyl groups such as 1-cyano-2,2,2-trifluoroethyl;

C1–C5 alkoxycarbonyl C1–C5 alkyl groups such as 1-(methoxycarbonyl)ethyl; and

C1–C5 alkyl groups substituted with a C3–C8 alicyclic hydrocarbon group which may be substituted with a halogen atom and may contain unsaturated bonds, such as 1-cyclopropyethyl.

Examples of the optionally substituted alkenyl groups represented by $R^6$ and $R^{61}$ include:

C3–C10 alkenyl groups such as 1-methyl-2-propenyl; and

C3–C10 haloalkenyl groups.

Examples of the optionally substituted alkynyl groups include:

C3–C10 alkynyl groups such as 1-methyl-2-propynyl, and

C3–C10 aloalkynyl groups.

Examples of the optionally substituted alicyclic hydrocarbon groups include:

C3–C8 alicyclic hydrocarbon groups;

C3–C8 alicyclic hydrocarbon groups which may be substituted with a halogen atom and may contain unsaturated bonds, such as cyclopentyl and cyclohexyl; and Phenyl groups and C7–C17 aralkyl groups which may be substituted with at least one group selected from halogen atoms, C1–C5 alkyl groups, C1–C5 alkoxyl groups, C1–C5 alkylthio groups, C1–C5 haloalkyl groups, C1–C5 haloalkoxyl groups and C1–C5 haloalkylthio groups and cyano group, such as benzyl, α-methylbenzyl and α,α-dimethylbenzyl.

Examples of the optionally substituted alkyl groups represented by X or $X^1$ in the present invention include:

C1–C10 alkyl groups such as methyl, ethyl, propyl, isopropyl, butyl, isobutyl, secondary butyl, 2-methylbutyl, isopentyl and tertiary butyl;

C1–C10 haloalkyl groups such as trifluoromethyl, tetrafluoroethyl, 2-chloroethyl, 3-chloropropyl and 4-chlorobutyl;

C1–C5 alkoxy C1–C5 alkyl groups such as methoxymethyl and 2-methoxyethyl;

C1–C5 alkylthio C1–C5 alkyl groups such as methylthiomethyl and 2-methylthioethyl;

C1–C5 haloalkoxy C1–C5 alkyl groups such as 2,2,2-trifluoroethoxymethyl;

C1–C5 haloalkoxy C1–C5 haloalkyl groups;

C1–C5 haloalkylthio C1–C5 alkyl groups such as 2,2,2-trifluoroethylthiomethyl;

C1–C5 haloalkylthio C1–C5 haloalkyl groups;

Cyano C1–C5 alkyl groups such as cyanomethyl, 1-cyanoethyl and 2-cyanoethyl;

Cyano C1–C5 haloalkyl groups; and

C1–C5 alkoxycarbonyl C1–C5 alkyl groups such as 1-(methoxycarbonyl)ethyl.

Examples of the optionally substituted aralkyl groups include C7–C17 aralkyl groups which may be substituted with at least one group selected from halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano groups, such as benzyl, α-methylbenzyl and α,α-dimethylbenzyl; and C1–C5 alkyl groups substituted with a C3–C8 alicyclic hydrocarbon group which may be substituted with a halogen atom and may contain unsaturated bonds, such as cyclopropylmethyl, cyclobutylmethyl, cyclopentylmethyl and cyclohexylmethyl.

Examples of the optionally substituted alkenyl groups include C2–C10 alkenyl groups such as vinyl, 1-propenyl, 2-propenyl, 1-butenyl, 2-butenyl and 3-butenyl; and C2–C10 haloalkenyl groups such as 3,3,3-trifluoropropenyl, and 1,1,2,3,3-pentafluoro-2-propenyl.

Examples of the optionally substituted alkynyl groups include C2–C10 alkynyl groups such as ethynyl, propalgyl, 2-butynyl and 3-butynyl; and C2–C10 haloalkynyl groups such as 3,3,3-tetrafluoropropynyl.

Examples of the optionally substituted alkoxyl groups include C1–C10 alkoxyl groups such as methoxy, ethoxy, propoxy, butoxy, pentyloxy, hexyloxy, isobutoxy, 2-methylbutoxy and isopentyloxy;

C1–C10 haloalkoxyl groups such as trifluoroethoxy, tetrafluoroethoxy, pentafluoroethoxy, tetrafluoropropoxy, 2-chloroetoxy, 3-chloropropoxy and 4-chlorobutoxy;

C1–C5 alkoxy C1–C5 alkoxyl groups such as 2-methoxyethoxy;

C1–C5 alkylthio C1–C5 alkoxyl groups such as 2-methylthioethoxy;

C1–C5 haloalkoxy C1–C5 alkoxyl groups such as 2,2,2-trifluoroethoxymethoxy;

C1–C5 haloalkoxy C1–C5 haloalkoxyl groups;

C1–C5 haloalkylthio C1–C5 alkoxyl groups such as 2,2,2-trifluoroethylthiomethoxy;

C1–C5 haloalkylthio C1–C5 haloalkoxyl groups;

Cyano C1–C5 alkoxyl groups such as 2-cyanoethoxy;

C1–C5 alkoxycarbonyl C1–C5 alkoxyl groups such as 2-(methoxycarbonyl)ethoxyl;

C1–C5 alkoxyl groups substituted with a C3–C8 alicyclic hydrocarbon group which may be substituted with a halogen atom and may contain unsaturated bonds, such as cyclopropylmethoxy, cyclobutylmethoxy, cyclopentylmethoxy and cyclohexylmethoxy.

Examples of the optionally substituted alkenyloxy groups include C2–C10 alkenyloxy groups such as 2-propenyloxy, 2-butenyloxy and 3-butenyloxy; and C2–C10 haloalkenyloxy groups such as 2,3,3-trifluoro-2-propenyloxy, 4,4,4-trifluoro-2-butenyloxy, 2,3-difluoro-2-butenyloxy, and 2,4,4,4-trifluoro-2-butenyloxy.

Examples of the optionally substituted alkynyloxy groups include C2–C10 alkynyloxy groups such as 2-propynyloxy, 2-butynyloxy, and 3-butynyloxy; and C2–C10 haloalkynyloxy groups such as 4-chloro-2-butynyloxy.

Examples of the optionally substituted alkylthio groups include C1–C10 alkylthio groups such as methylthio, ethylthio, propylthio, butylthio, pentylthio, hexylthio, isobutylthio, 2-methylbutylthio and isopentylthio;

C1–C10 haloalkylthio groups such as trifluoroethylthio, tetrafluoroethylthio, pentafluoroethylthio, tetrafluoropropylthio, 2-chloroethylthio, 3-chloropropylthio, and 4-chlorobutylthio;

C1–C5 alkoxy C1–C5 alkylthio groups such as 2-methoxyethylthio:

C1–C5 alkylthio C1–C5 alkylthio groups such as 2-methylthioethylthio;

C1–C5 haloalkoxy C1–C5 alkylthio groups such as 2,2,2-tetrafluoroethoxymethylthio;

C1–C5 haloalkoxy C1–C5 haloalkylthio groups;

C1–C5 haloalkylthio C1–C5 alkylthio groups such as 2,2,2-tetrafluoroethylthiomethylthio:

C1–C5 haloalkylthio C1–C5 haloalkylthio groups;

Cyano C1–C5 alkylthio groups such as 2-cyanoethylthio;

C1–C5 alkoxycarbonyl C1–C5 alkylthio groups such as 2-(methoxycarbonyl)ethylthio;

C1–C5 alkylthio groups substituted with a C3–C8 alicyclic hydrocarbon group which may be substituted with a halogen atom and may contain unsaturated bonds, such as cyclopropylmethylthio, cyclobutylmethylthio, cyclopentylmethylthio, cyclohexylmethylthio, (1-cyclopentenyl)methylthio, and (1-cyclohexenyl)methylthio.

Examples of the optionally substituted alkenylthio groups include C2–C10 alkenylthio groups such as 2-propenylthio, 2-butenylthio and 3-butenylthio;

C2–C10 haloalkenylthio groups such as 2,3,3-tetrafluoro-2-propenylthio, 4,4,4-tetrafluoro-2-butenylthio, 2,3-difluoro-2-butenylthio and 2,4,4,4-tetrafluoro-2-butenylthio.

Examples of the optionally substituted alkynylthio groups include C2–C10 alkynylthio groups such as 2-propynylthio, 2-butenylthio and 3-butenylthio; and C2–C10 haloalkynylthio groups.

Examples of the optionally substituted alicyclic hydrocarbon groups include C3–C8 alicyclic hydrocarbon groups which may be substituted with a halogen atom and may contain unsaturated bonds, such as cyclopropyl, cyclobutyl, cyclopentyl, cyclohexyl, 1-cyclopentenyl, 2-cyclopentenyl, 3-cyclopentenyl, 1,3-cyclopentadienyl, 2,4-cyclopentadienyl, 1-cyclohexenyl, 2-cyclohexenyl and 3-cyclohexenyl.

Examples of the optionally substituted phenyl groups, phenoxyl groups, C7–C17 aralkyloxy groups, C7–C17 aralkylthio groups and phenylthio groups include the phenyl groups, phenoxyl groups, C7–C17 aralkyl groups (such as benzyl, α-methylbenzyl and α,α-dimethylbenzyl), C7–C17 aralkyloxy groups and C7–C17 aralkylthio groups (such as benzylthio) which may be substituted with at least one group selected from halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano group.

Examples of the substituents include:

halogen atoms such as fluorine, chlorine, bromine and iodine;

C1–C5 alkyl groups such as methyl, ethyl, n-propyl, i-propyl, n-butyl and n-pentyl;

C1–C5 alkoxyl groups such as methoxy and ethoxy;

C1–C5 alkylthio groups such as methylthio and ethylthio;

C1–C5 haloalkyl groups, preferably C1–C2 haloalkyl groups such as trifluoromethyl;

C1–C5 haloalkoxyl groups, preferably C1–C2 haloalkoxyl groups such as trifluoromethoxy and difluoromethoxy;

C1–C5 haloalkylthio groups, preferably C1–C2 haloalkylthio groups such as trifluoromethylthio; and cyano groups.

In the present compounds in view of their efficacy for plant diseases, preferred examples of the substituents represented by X are C1–C5 alkyl groups, C1–C5 haloalkoxyl groups, C2–C5 alkenyloxy groups, C2–C5 haloalkenyloxy groups, C2–C5 alkynyloxy groups, C2–C5 haloalkynyloxy groups, C1–C5 alkylthio groups, C1–C5 haloalkylthio groups, C2–C5 alkenylthio groups, C2–C5 haloalkenylthio groups, C2–C5 alkynylthio groups and C2–C5 haloalkynylthio groups.

The present compounds can exist in the form of various tautomeric structures represented by the following formula [VII], and all of these tautomers are embraced within the concept of the present compounds.

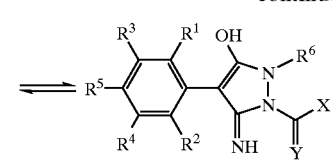

Further, the present compounds may take the form of stereoisomers originating in the presence of double bonds and asymmetric carbon atoms, and these stereoisomers and their mixtures are also comprehended in the present compounds.

The intermediate A can exist in the form of various tautomeric structures represented by the following formula [VIII], and all of these tautomers are included in the intermediate A of the present invention.

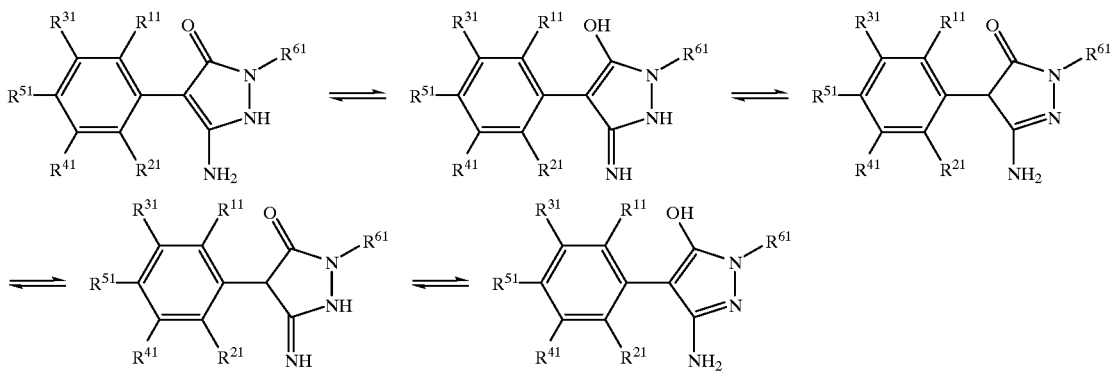

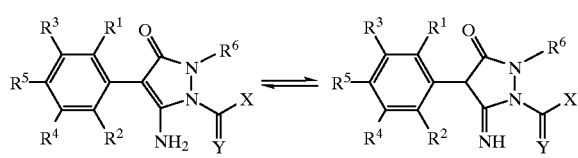

The intermediate A may take the form of stereoisomers originating in the presence of double bonds and asymmetric carbon atoms, and these stereoisomers and their mixtures also fall within the ambit of the present compound.

The intermediate B can exist in the form of various tautomeric structures represented by the following formula [IX], and all of these tautomers are comprehended in the intermediate B of the present invention.

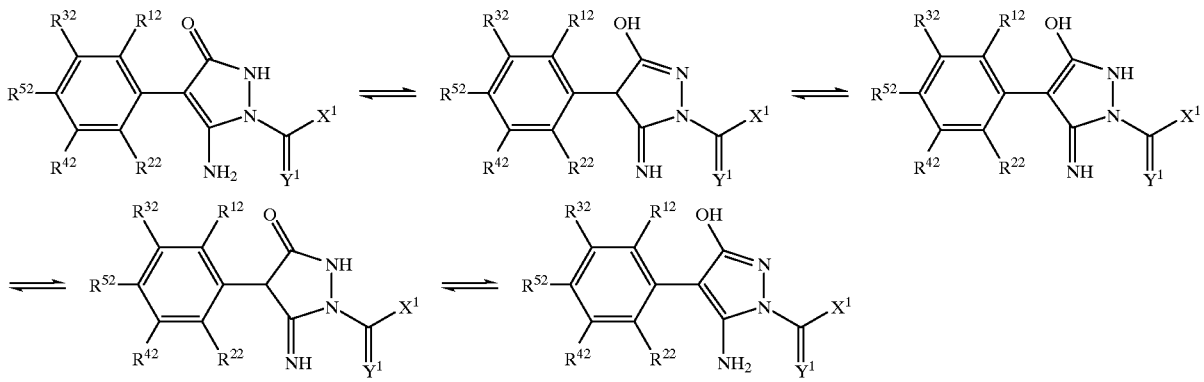

Further, in the intermediate B, there may exist the stereoisomers originating in the presence of double bonds and asymmetric carbon atoms, and these stereoisomers and their mixtures are also embraced in the concept of intermediate B according to the present invention.

The present compounds can be produced from the following processes.

(Process 1)

An alkaline metal salt of an intermediate A is reacted with a compound represented by the formula [X]:

[wherein X and Y are as defined previously, and Z represents a halogen atom (such as chlorine atom or bromine atom)] in an organic solvent.

The reaction is carried out at a temperature in the range of usually 80 to 140° C. for a period of usually 0.1 to 5 hours, using a compound of the formula [X] usually in a ratio of 1 to 3 moles, preferably 1.1 to 2 moles to one mole of an alkaline metal salt of an intermediate A.

As the organic solvent in the above reaction, aromatic hydrocarbons such as toluene, xylene and chlorobenzene, ethers such as diethyl ether, 1,4-dioxane, tetrahydrofuran, tetrahydropyran, diisopropyl ether and dimethoxyethane, dimethylformamide, and mixtures thereof can be used. 1,4-dioxane or dimethoxyethane is preferably used.

After the completion of the reaction, the reaction solution is poured into water and subjected to the ordinary after-treatments such as extraction with an organic solvent and concentration to give the present compound. The obtained compound can be purified by suitable means such as washing with an organic solvent, recrystallization and column chromatography.

An alkaline metal salt of an intermediate A can be produced by reacting an intermediate A with sodium hydroxide, anhydrous lithium hydroxide or a lithium hydroxide monohydrate under an azeotropic dehydrating condition, or by reacting an intermediate A with sodium hydride or lithium hydride.

In case of reacting an intermediate A with sodium hydroxide, anhydrous lithium hydroxide or a lithium hydroxide monohydrate under an azeotropic dehydrating condition, the reaction is carried out usually at 80 to 140° C. for usually 0.5 to 12 hours by supplying usually 1 to 5 moles, preferably 1.1 to 2 moles of sodium hydroxide, anhydrous lithium hydroxide or a lithium hydroxide monohydrate to one mole of an intermediate A, using, for example, an aromatic hydrocarbon such as toluene, xylene or chlorobenzene as the reaction solvent.

In case of reacting an intermediate A with sodium hydride or lithium hydride, the reaction is conducted usually at 60 to 120° C. for a period of usually 1 to 12 hours by supplying 1 to 2 moles of sodium hydride or lithium hydride to one mole of an intermediate A, using, for example, an aromatic hydrocarbon such as toluene, xylene or chlorobenzene, an ether such as diethyl ether, 1,4-dioxane, tetrahydrofuran, tetrahydropyran, diisopropyl ether or dimethoxyethane, or dimethylformamlde, preferably 1,4-dioxane or dimethoxyethane as the reaction solvent.

After the completion of the reaction, the solvent in the reaction solution is distilled off under reduced pressure to form an alkaline metal salt of an intermediate A.

The compounds represented by the formula [X] can be produced, for instance, according to the methods described in Org. Syn. 1, 147; J. Am. Chem. Soc. 73, 3796 (1951); J. Am. Chem. Soc. 81, 714 (1959); Angew. Chem. Int. Ed. Engl., 26, 894 (1987); and Synthesis, 760 (1986).

The intermediates A can be produced by acting an acid catalyst to the pyrazolinone derivatives represented by the formula [XI]:

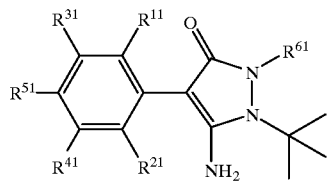

[wherein $R^{11}$, $R^{21}$, $R^{31}$, $R^{41}$, $R^{51}$ and $R^{61}$ are as defined previously].

The reaction is carried out usually at a temperature in the range of 80 to 120° C. for a period of usually 1 to 12 hours by supplying usually 0.1 mole to an excess amount of an acid to one mole of a pyrazolinone derivative of the formula [XI].

As the acid in the above reaction, there can be used, for example, mineral acids such as hydrochloric acid and sulfuric acid in the form of an aqueous solution.

As the solvent, the above-mentioned acids, alcohols such as methanol and ethanol, their mixtures, etc., can be used.

After the completion of the reaction, the reaction solution may be neutralized with a basic aqueous solution such as a sodium hydroxide solution or a sodium hydrogencarbonate solution, then concentrated and washed with water to produce an intermediate A. The obtained compound can be purified by suitable means such as washing with an organic solvent, recrystallization, column chromatography, etc.

The pyrazolinone derivatives represented by the formula [XI] can be produced according to the method described in JP-A-8-208621.

(Process 2)

An alkaline metal salt of an intermediate B is reacted with a compound represented by the formula [XII]:

R$^6$—L

[wherein R$^6$ is as defined above, and L represents a chlorine atom, a bromine atom, an iodine atom, a C1–C10 alkanesulfonyloxy group or an optionally substituted benzenesulfonyloxy group] in an organic solvent.

The reaction is carried out usually at a temperature in the range of 60 to 150° C., preferably 80° to 120° C. for a period of usually 0.1 to 12 hours by supplying usually 1 to 5 moles, preferably 1 to 2.5 moles of a compound of the formula [XI] to one mole of an alkaline metal salt of an intermediate B.

The organic solvents usable for the above reaction include aromatic hydrocarbons such as benzene, toluene, xylene and chlorobenzene, aliphatic hydrocarbons such as normal hexane and normal heptane, ethers such as tetrahydrofuran, 1,4-dioxane and tetrahydropyran, and their mixtures.

After the completion of the reaction, the reaction solution is poured into acidic water and then subjected to the ordinary after-treatments such as extraction with an organic solvent, concentration, etc., to produce the present compound. The obtained compound can be purified by suitable means such as washing with an organic solvent, recrystallization, column chromatography, etc.

An alkaline metal salt of an intermediate B can be produced by reacting an intermediate B with sodium hydroxide, anhydrous lithium hydroxide or a lithium hydroxide monohydrate under an azeotropic dehydrating condition, or by reacting an intermediate B with sodium hydride or lithium hydride.

In case of reacting an intermediate B with sodium hydroxide, anhydrous lithium hydroxide or a lithium hydroxide monohydrate under an azeotropic dehydrating condition, the reaction is carried out usually at 80 to 140° C. for usually 0.5 to 12 hours by supplying usually 1 to 5 moles, preferably 1.1 to 2 moles of sodium hydroxide, anhydrous lithium hydroxide or a lithium hydroxide monohydrate to one mole of an intermediate B using, for instance, an aromatic hydrocarbon such as toluene, xylene or chlorobenzene as the reaction solvent.

In case of reacting an intermediate B with sodium hydride or lithium hydride, the reaction is carried out usually at 60 to 120° C. for usually 1 to 12 hours by supplying 1 to 2 moles of sodium hydride or lithium hydride to one mole of an intermediate B, using an aromatic hydrocarbon such as toluene, xylene or chlorobenzene, an ether such as diethyl ether, 1,4-dioxane, tetrahydrofuran, tetrahydropyran, diisopropyl ether or dimethoxyethane, dimethylformamide or the like, preferably 1,4-dioxane or dimethoxyethane as the reaction solvent.

The intermediates B can be produced, for example, by the following processes.

{Preparation Process 1 of the Intermediate}

A pyrazolinone compound represented by the formula [V']:

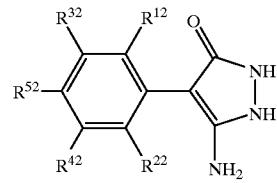

[wherein R$^{12}$, R$^{22}$, R$^{32}$, R$^{42}$ and R$^{52}$ are as defined above] is reacted with a compound represented by the formula [XIII]:

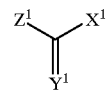

[wherein X$^1$ and Y$^1$ are as defined above, and Z$^1$ represents a halogen atom (such as chlorine atom or bromine atom)] in an organic solvent in the presence of a base.

The reaction is carried out usually at a temperature in the range of 0 to 100° C., preferably 10 to 50° C., for a period of usually 1 to 12 hours by supplying usually 0.8 to 1.2 mole, preferably 1 to 1.1 mole of a compound of the formula [XIII] to one mole of a pyrazolinone compound of the formula [V']. A base is used in a ratio of usually 1 to 5 moles, preferably 1 to 1.5 mole.

As the base, there can be used inorganic bases, for example, alkaline metal hydroxides such as lithium hydroxide, sodium hydroxide and potassium hydroxide, alkaline earth metal hydroxides such as magnesium hydroxide and calcium hydroxide, alkaline metal or alkaline earth metal carbonates such as sodium carbonate, potassium carbonate, magnesium carbonate and calcium carbonate, and alkaline metal bicarbonates such as sodium bicarbonate and potassium bicarbonate, and organic bases such as pyridine, N,N-dimethylpyridine and triethylamine. In case of using an inorganic base, it may be applied as an aqueous solution.

As the solvent, aromatic hydrocarbons such as benzene, toluene, xylene and chlorobenzene, aliphatic hydrocarbons such as normal hexane and normal heptane, ketones such as methyl ethyl ketone and methyl isobutyl ketone, ethers such as tetrahydrofuran, 1,4-dioxane and tetrahydropyran, and their mixtures can be used. Water may be allowed to co-exist with an organic solvent, in which case water and the organic solvent may stay homogeneous or heterogeneous.

After the completion of the reaction, the reaction solution is poured into acidic water and subjected to the ordinary after-treatments such as extraction with an organic solvent, concentration of the organic layer, etc., to obtain an intermediate B. The obtained compound may be purified by suitable means such as washing with an organic solvent, recrystallization, column chromatography, etc.

The pyrazolinone derivatives represented by the formula [V'] can be produced, for example, according to the method described in J. Chem. Soc. Chem. Commum., 23, 1755–1757 (1993).

The compounds represented by the formula [XIII] can be produced according to the methods described in Org. Syn. 1, 147; J. Am. Chem. Soc. 73, 3796 (1951); J. Am. Chem. Soc., 81, 714 (1959); Angew. Chem. Int. Ed. Engl., 26, 984 (1987); Synthesis, 760 (1986), etc.

{Preparation Process 2 of the Intermediate}

A pyrazolinone compound represented by the formula [V'] is reacted with a compound represented by the formula [XIV]:

$$Z^2\text{—G}$$

[wherein G represents a C1–C5 trialkylsilyl group such as trimethylsilyl, treithylsilyl, dimethylethylsilyl, dimethylisopropyl or tert-butyldimethylsilyl, and $Z^2$ represents a halogen atom such as chlorine, bromine or iodine] in an organic solvent in the presence of a base, then further reacted with a compound represented by the formula [XIII], and subjected to the after-treatments in acidic water.

The reaction is carried out usually at a temperature in the range of 0 to 100° C., preferably 0 to 30° C. for a period of usually 1 to 12 hours by supplying usually 1 to 1.5 mole, preferably 1 to 1.2 mole of a compound of the formula [XIV] and a compound of the formula [XIII] to one mole of a pyrazolinone compound of the formula [V']. The ratio of the base used in the reaction is usually 2 to 10 moles, preferably 2 to 5 moles.

As the base, organic bases such as pyridine and triethylamine can be used.

As the solvent, aromatic hydrocarbons such as benzene, toluene, xylene and chlorobenzene, aliphatic hydrocarbons such as normal hexane and normal heptane, ketones such as methyl ethyl ketone and methyl isobutyl ketone, ethers such as tetrahydrofuran, 1,4-dioxane and tetrahydropyran, and their mixtures can be used.

After the completion of the reaction, the reaction solution is poured into acidic water, or if necessary the reaction solution is filtered to remove the precipitate and the filtrate is poured into acidic water, then stirred under reflux for 0.5 to 5 hours, preferably 0.5 to 2 hours, extracted with an organic solvent, and subjected to the after-treatments such as concentration of the organic layer to give a pyrazolinone compound of the formula [VI]. The obtained compound can be purified by suitable means such as washing with an organic solvent, recrystallization, column chromatography, etc.

(Process 3)

An intermediate B and a compound represented by the formula [XII] are reacted in an organic solvent in the presence of a base.

The reaction is carried out at a temperature in the range of usually 60 to 180° C., preferably 80 to 120° C. for a period of usually 1 to 12 hours by supplying usually 1 to 5 moles, preferably 1 to 2.5 moles of a compound of the formula [XI] to one mole of an alkaline metal salt of an intermediate B and allowing a base to exist in a ratio of usually 1 to 5 moles, preferably 1 to 2.5 moles.

As the base in the above reaction, organic bases, for example, alkaline metal hydroxides such as lithium hydroxide, sodium hydroxide and potassium hydroxide, alkaline earth metal hydroxides such as magnesium hydroxide and calcium hydroxide, alkaline metal or alkaline earth metal carbonates such as sodium carbonate, potassium carbonate, magnesium carbonate and calcium carbonate, alkaline metal bicarbonates such as sodium bicarbonate and potassium bicarbonate, pyridine, N-N-dimethylpyridine, triethylamine, etc., can be used.

As the organic solvent for the above reaction, aromatic hydrocarbons such as benzene, toluene, xylene and chlorobenzene, aliphatic hydrocarbons such as normal hexane and normal heptane, ethers such as tetrahydrofuran, 1,4-dioxane and tetrahydropyran, and their mixtures are usable.

If necessary, molecular sieves (synthetic zeolite) may be allowed to exist in the reaction system.

After the completion of the reaction, the reaction solution is poured into acidic water and subjected to the ordinary after-treatments such as extraction with an organic solvent, concentration, etc., to obtain the present compound. The obtained compound may be purified by suitable means such as washing with an organic solvent, recrystallization, column chromatography, etc.

When the present compound is used as an active ingredient of the plant diseases controlling agent, the compounds may be used as they are without adding any other components, but usually they are mixed with proper adjuvants such as solid carrier, liquid carrier, surfactant, etc., and formulated into a desired form of preparation such as emulsifiable concentrate, wettable powder, flowable, dust, granule, etc. In these formulations, the content of the present compound as an active ingredient is usually 0.1 to 99%, preferably 1 to 90% in ratio by weight.

Examples of the solid carriers usable in the formulations include fine powders or granules of kaolin clay, attapulgite clay, bentonite, acid clay, pyrophyllite, talc, diatomaceous earth, calcite, corncob, walnut shell, urea, ammonium sulfate, synthetic hydrous silicon oxide and the like. Examples of the liquid carriers include aromatic hydrocarbons such as xylene and methyl naphthalene, alcohols such as isopropanol, ethylene glycol and cellosolve, ketones such as acetone, cyclohexanone and isophorone, plant oils such as soybean oil and cottonseed oil, dimethyl sulfoxide, acetonitrile and water.

Examples of the surfactants usable for the above formulations include anionic surfactants such as alkylsulfate ester salts, alkyl(aryl)sulfonates, dialkyl sulfosuccinate, polyoxyethylene alkylaryl ether phosphoric ester salts, naphthalenesulfonic acid-formalin condensate, etc., and nonionic surfactants such as polyoxyethylene alkyl ether, polyoxyethylene-alkylpolyoxypropene block copolymer, sorbitan fatty acid esters, etc.

Examples of the adjuvants usable for the above formulations include lignin sulfonate, alginates, polyvinyl alcohol, gum arabic, carboxymethyl cellulose (CMC), acidic isopropyl phosphate (PAP) and the like.

The present compound may be applied in folian application, soil treatment, seed disinfection and the like, and usually any application method which one skilled in the art employs may also be used.

When the present compound is used as an active ingredient for the plant disease controlling agent, the quantity of the compound (active ingredient) to be applied is usually 0.01 to 5 g/are, preferably 0.05 to 10 g/are, though it is variable depending on the type of the plant (crop, etc.) to be treated, type of the plant disease to be controlled, degree of affection by the disease, dosing form way of application, time of application, weather conditions, etc.

In case the compound is used in the form of an emulsifiable concentrate, wettable powder, flowable etc. by diluting it with water, the concentration of the compound in such aqueous formulations should be 0.0001 to 0.5%, preferably 0.0005 to 0.2%. When the compound is used as a dust or granule, it may be applied as it is without dilution.

The present compound can be used as a controlling agent against plant diseases in the plowed fields, paddy fields, orchards, tea plantations, pastures, lawns and the like. Also, an increased germicidal effect can be expected by using the compounds in admixture with other known plant disease controlling agents. Examples of such admixable other controlling agent include azole type germicidal compounds such as Propiconazole, Triadimenol, Prochloraz Penconazole, Tebuconazole, Flusilazole, Diniconazole, Bromconazole, Epoxyconazole, Diphenoconazole, Ciproconazole, Metoconaznole, Triflumizole, Tetraconazole, Microbutanil, Fenbuconal, Hexaconazole, Fluquinconazole, Triticonazole (RPA4007), Bitertanol, Imazalil, and Flutriafol, cyclic amine type germicidal compounds such as Fenpropimorph, Tridemorph and Fenpropidin, benzimidazole type germicidal compounds such as Carbendazim, Benonyl, Tiabendazole and Thiophanate-methyl, procymidone, Cyprodinil, Pyrimethanil, Diethofencarb, Thiuram, Fluazinam, Mancozeb, Iprodione, Vinclozolin, Chlorothalonil, Captan, Mapanipyrim, Fenpiclonil, Kresoximmethyl, Fludioxonil, Dichlofluanide, Folpet, Azoxystrobin, and N-methyl-α-methoxyimino-2-[(2,5-dimethylphenoxy)methyl]-phenylacetamide. Further, the compounds of the present invention can be used in admixture or combination with the known insecticides, miticides, nemacides, herbicides, plant growth regulators and fertilizers.

The present compound are effective for controlling a variety of plant diseases, for example, those mentioned below:

*Pyricularia oryzae, Cochliobolus miyabeanus, Rhizoctonia solani, Erysiphe graminis, Gibberella zeae, Puccinia striiformis, P. graminis, P. recondita, P. hordei*, Typhula sp., *Micronectriella nivalis, Ustilago tritici, U. nuda, Tilletia caries, Pseudocercosporella herpotrichoides, Rhynchosporium secalis, Septoria tritici, Leptosphaeria nodorum, Diaporthe citri, Elsinoe fawcetti, Penicillium digitatum, P. italicum, Sclerotinia mali, Valsa mali, Pososphaera leucotricha, Alternaria mali, Venturia inaeqaulis, Venturia nashicola, V. pirina, Alternaria kikuchiana, Gymnosporangium haraeanum, Sclerotinia cinerea, Cladosporium carpophilum*, Phomopsis sp., *Elsinoe ampelina, Glomerella cingulata, Uncinula necator, Phakopsora ampelopsidis, Guignardia bidwellii, Plasmopara viticola, Gloeosporium kaki, Cercospora kaki, Mycosphaerella nawae, Colletotrichum lagenarium, Sphaerotheca fuliginea, Mycosphaerella melonis, Fusarium oxysporum, Pseudoperonospora cubensis*, Phytophthora sp., Pythium sp., *Alternaria solani, Cladosporium fulvum, Phytophthora inlestans, Phomopsis vexans, Erysiphe cichoracearum, Alternaria japonica, Cercosporella brassicae, Puccinia allii, Cercospora kikuchii, Elsinoe glycines, Diaporthe phaseolorum* var. sojae, *Colletotrichum lindemthianum, Cercospora personata, Cercospora arachidicola, Erysiphe pisi, Alternaria solani, Phytophthora infestans, Sphaerotheca humuli, Exobasidium reticulatum, Elsinoe leucospila, Alternaria longipes, Erysiphe cichoracearum, Colletorichum tabacum, Peronospora tabacina, Phytophthora nicotianae, Cercospora beticola, Diplocarpon rosae, Sphaerotheca pannosa, Septoria chrysanthemi indici, Puccinia horiana, Botrytis cinerea* of various farm products, and *Sclerotinia sclerotiorum*.

EXAMPLES

The present invention is explained in more detail in the following Production Examples, Formulation Examples and Test Examples, but it should be understood that the scope of the present invention is not restricted to these Examples.

First, the production examples of the present compound, their intermediate A and intermediate B are described. In the following descriptions of the Examples, the compound numbers correspond to those shown in Tables 1 to 64 given below. The symbol "(+)-" or "(−)-" put in front of the compound number indicates that the compound is a single body of an optically active substance or a mixture of optically active substances and has a plus (+) or minus (−) specific rotation.

For the purity assay of the obtained objective products, liquid chromatographic analysis (hereinafter referred to as LC) was conducted under the following conditions.

<LC Conditions>

Analyzer: low pressure gradient type (Hitachi L-6000 Series)

Column: L-column ODS (4.6 mmφ×150 mm; mfd. by Kagakuhin Kensa Kyokai (Chemical Substances Testing Association)

Column temperature: 40° C.

Detector: UV (254 nm)

Mobile phase condition: gradient method (solution A & solution B)

Time (min): 0, 10, 35, 45

Solution B conc. (%): 50, 50, 100, 100

Flow rate (ml/min): 1.0 ml/min (Solution A: 0.1% phosphoric acid/water; solution B: 0.1% phosphoric acid/acetonitrile)

Production Example 1

1.57 (5.5 mmol) of an intermediate A (Compound 1007) was suspended in 20 ml of dioxane, to which 0.30 g (7.5 mmol) of 60% oily sodium hydride was added, and the mixture was heated to 90° C. Then 0.72 g (7.6 mmol) of methyl chloroformate was added dropwise. After stirring at the same temperature for one hour, the reaction solution was poured into water and extracted with ethyl acetate. The organic layer was washed with water and the solvent was distilled off under reduced pressure. The residue was subjected to silica gel column chromatography, and the obtained white solid was washed with a mixed solvent of ethyl acetate and hexane to obtain 0.13 mg (0.38 mmol) of the present compound (Compound 138).

$^1$H-NMR (CDCl$_3$, TMS) δ (ppm): 7.33 (1H), 7.15–7.21 (2H), 5.74 (2H), 4.02 (1H), 3.96 (3H), 1.37 (6H).

Production Example 2

50 ml of toluene was added to a mixture of 5.00 g (17.5 mmol) of an intermediate A (Compound 1007) and 1.47 g (35.0 mmol) of lithium hydroxide monohydrate, and the mixture was refluxed for 30 minutes while removing water by azeotropic dehydration. Toluene was distilled off under reduced pressure, then 35 ml of 1,4-dioxane was added and further 4.22 g (35.0 mmol) of aryl chloroformate was added dropwise under reflux. After stirring for 15 minutes under the refluxing condition, 1,4-dioxane was distilled off under reduced pressure. Water was added to the residue and the solution was extracted with ethyl acetate. The organic layer was washed twice with water and the solvent was distilled off under reduced pressure. A small quantity of a hexane/ethyl acetate mixed solvent was added to the residue, and the precipitated solids were filtered out and washed with a hexane/ethyl acetate mixed solvent to obtain 2.67 g (7.22 mmol) of the present compound (Compound 203) having a melting point of 173.8° C.

Production Example 3

20 ml of toluene was added to a mixture of 2.45 g (10.0 mmol) of an intermediate A (Compound 1017) and 0.84 g (20.0 mmol) of lithium hydroxide monohydrate, and the mixture was refluxed for 30 minutes while removing water by azeotropic dehydration. Toluene was distilled off under reduced pressure, then 20 ml of 1,4-dioxane was added and further 2.41 g (20.0 mmol) of allyl chloroformate was added dropwise under reflux. After stirring for 10 minutes under the refluxing condition, 1,4-dioxane was distilled off under reduced pressure. Water was added to the residue and the solution was extracted with ethyl acetate. The organic layer was washed twice with water, then the solvent was distilled off under reduced pressure and the residue was subjected to silica gel column chromatography to obtain 0.53 g (1.88 mmol) of the present compound (Compound 330) having a melting point of 102.1° C.

Production Example 4

1.57 g (5.5 mmol) of an intermediate A (Compound 1007) was dissolved in 5 ml of dimethylformamide, to which 0.30 g (7.5 mmol)of 60% oily sodium hydride was added under cooling with water, followed by dropwise addition of 0.65 g (5.99 mmol) of ethyl chloroformate under cooling with water. After stirring at room temperature for 30 minutes, the reaction solution was poured into water and extracted with ethyl acetate, and the organic layer was washed with water. The solvent was distilled off under reduced pressure, and the residue was washed with an ethyl acetate/hexane mixed solvent to obtain 0.61 g (1.76 mmol) of the present compound (Compound 151).

$^1$H-NMR (CDCl$_3$, TMS) δ (ppm): 7.37 (1H), 7.18–7.23 (2H), 5.71 (2H), 4.42 (2H), 4.05 (1H), 1.40–1.47 (9H).

Production Example 5

0.98 g (3.44 mmol) of an intermediate A (Compound 1007) was dissolved in 5 ml of dimethylformamide, to which 0.15 g (3.75 mmol) of 60% oily sodium hydride was added under cooling with water and stirred for 30 minutes. Then 0.54 g (3.78 mmol) of 2-chloroethyl chloroformate was added dropwise under cooling with water. After stirring at room temperature for one hour, the reaction solution was poured into water and extracted with ethyl acetate, and the organic layer was washed with water. The solvent was distilled off under reduced pressure and the residue was washed with an ethyl acetate/hexane mixed solvent to provide 0.68 g (1.72 mmol) of the present compound (Compound 582).

$^1$H-NMR (CDCl$_3$, TMS) δ (ppm): 7.37 (1H), 7.19–7.24 (2H), 5.69 (2H), 4.60 (2H), 4.09 (1H), 3.84 (2H), 1.44 (6H).

Production Example 6

15 ml of toluene was added to a mixture of 2.00 g (6.99 mmol) of an intermediate A (Compound 1007) and 0.59 g (14 mmol) of lithium hydroxide monohydrate, and the mixture was refluxed for 30 minutes while removing water by azeotropic dehydration. Toluene was distilled off under reduced pressure, then 20 ml of 1,4-dioxane was added and further 1.91 g (14 mmol) of isobutyl chloroformate was added dropwise under reflux. After stirring for 10 minutes under the refluxing condition, 1,4-dioxane was distilled off under reduced pressure. Water was added to the residue and the solution was washed with an ethyl acetate/hexane mixed solvent to obtain 1.0 g (2.59 mmol) of the present compound (Compound 190) having a melting point of 153.7° C.

Production Example 7

1.41 g (4.73 mmol) of bis(trichloromethyl)carbonate was dissolved in 10 mml of 1,4-dioxane, to which 1.12 g (14.2 mmol) of pyridine was added dropwise under cooling with water. After stirring at room temperature for 15 minutes, 0.79 g (14.1 mmol) of 2-propyne-1-ol was added dropwise, and after additional 35-minute stirring at room temperature, the reaction solution was filtered to obtain a filtrate. This filtrate is called "filtrate A".

20 ml of toluene was added to a mixture of 2.02 g (7.06 mmol) of an intermediate A (Compound 1007) and 0.59 g (14.0 mmol) of lithium hydroxide monohydrate, and the mixture was refluxed for 30 minutes while removing water by azeotropic dehydration. Toluene was distilled off under reduced pressure, then 15 ml of 1,4-dioxane was added and the previously obtained "filtrate A" was further added dropwise under reflux. After stirring for 5 minutes under the refluxing condition, 1,4-dioxane was distilled off under reduced pressure. Water was added to the residue and the solution was extracted with ethyl acetate, and the organic layer was washed twice with water. The solvent was distilled off under reduced pressure, and the residue was subjected to silica gel column chromatography to obtain 0.53 g (1.44 mmol) of the present compound (Compound 229) having a melting point of 137.4° C.

Production Example 8

0.98 g (3.29 mmol) of bis(trichloromethyl)carbonate was dissolved in 10 mml of 1,4-dioxane, to which 0.79 g (10.0 mmol) of pyridine was added dropwise under cooling with water. After stirring at room temperature for 15 minutes, 0.56 g (10.0 mmol) of 2-propyne-1-ol was added dropwise, and after additional 15-minute stirring at room temperature, the reaction solution was filtered to obtain a filtrate. This filtrate is called "filtrate B".

20 ml of toluene was added to a mixture of 1.50 g (5.00 mmol) of an intermediate A (Compound 1020) and 0.42 g (10.0 mmol) of lithium hydroxide monohydrate, and the mixture was refluxed for 30 minutes while removing water by azeotropic dehydration. After toluene was distilled off under reduced pressure, 10 ml of 1,4-dioxane was added and the previously prepared "filtrate B" was added dropwise under reflux. After stirring for one hour under the refluxing condition, 1,4-dioxane was distilled off under reduced pressure. Water was added to the residue, and the solution was extracted with ethyl acetate, and the organic layer was washed twice with water. The solvent was distilled off under reduced pressure and the residue was subjected to silica gel column chromatography to obtain 0.33 g (0.86 mmol) of the present compound (Compound 359) having a melting point of 132.7° C.

Production Example 9

1.40 g (4.67 mmol) of bis(trichloromethyl)carbonate was dissolved in 10 mml of 1,4-dioxane, to which 1.11 g (14 mmol) of pyridine was added dropwise under cooling with water. After stirring at room temperature for one hour, 1.03 g (14 mmol) of cyclopropane methanol was added dropwise, and after additional 15-minute stirring at room temperature, the reaction solution was filtered to obtain a filtrate. This filtrate is called "filtrate C".

20 ml of toluene was added to a mixture of 2.0 g (7.00 mmol) of an intermediate A (Compound 1007) and 0.59 g (14.0 mmol) of lithium hydroxide monohydrate, and the mixture was refluxed for one hour while removing water by azeotropic dehydration. Toluene was distilled off under reduced pressure, and 10 ml of 1,4-dioxane was added. Then the previously prepared filtrate C was added dropwise under reflux, and after stirring for 10 minutes under the refluxing condition, 1,4-dioxane was distilled off under reduced pressure. Water was added to the residue and the solution was extracted with ethyl acetate, and the organic layer was washed twice with water. The solvent was distilled off under reduced pressure, and the residue was washed with an ether/hexane mixed solvent to obtain 0.80 g (2.08 mmol) of the present compound (Compound 578) having a melting point of 178.2° C.

Production Example 10

1.40 g (4.67 mmol) of bis(trichloromethyl)carbonate was dissolved in 10 mml of 1,4-dioxane, to which 1.1 g (14 mmol) of pyridine was added dropwise under cooling with water. After stirring at room temperature for 15 minutes, 1.03 g (14 mmol) of 3-butene-1-ol was added dropwise, and after additional 15-minute stirring at room temperature, the reaction solution was filtered to obtain a filtrate. This filtrate is called "filtrate D".

20 ml of toluene was added to a mixture of 2.0 g (7.00 mmol) of an intermediate A (Compound 1007) and 0.59 g (14.0 mmol) of lithium hydroxide monohydrate, and the mixture was refluxed for one hour while removing water by azeotropic dehydration. With toluene distilled off under reduced pressure, 10 ml of 1,4-dioxane was added and the filtrate D was added dropwise under reflux. After stirring for 10 minutes under the refluxing condition, 1,4-dioxane was distilled off under reduced pressure. Water was added to the residue and the solution was extracted with ethyl acetate, and the organic layer was washed twice with water. The solvent was distilled off under reduced pressure and the residue was washed with an ethyl acetate/hexane mixed solvent to obtain 0.65 g (1.84 mmol) of the present compound (Compound 216) having a melting point of 133.1° C.

Production Example 11

1.40 g (4.67 mmol) of bis(trichloromethyl)carbonate was dissolved in 10 mml of 1,4-dioxane, to which 1.1 g (14 mmol) of pyridine was added dropwise under cooling with water. After stirring at room temperature for 30 minutes, 0.98 g (14 mmol) of 1-butyne-1-ol was added dropwise, and after additional 15-minute stirring at room temperature, the reaction solution was filtered to obtain a filtrate. This filtrate is called "filtrate E".

20 ml of toluene was added to a mixture of 2.0 g (7.00 mmol) of an intermediate A (Compound 1007) and 0.59 g (14.0 mmol) of lithium hydroxide monohydrate, and the mixture was refluxed for one hour while removing water by azeotropic dehydration. After distilling off toluene under reduced pressure, 10 ml of 1,4-dioxane was added and the filtrate E was further added dropwise under reflux. After further stirring for 10 minutes under the refluxing condition, 1,4-dioxane was distilled off under reduced pressure. Water was added to the residue and the solution was extracted with ethyl acetate, and the organic layer was washed twice with water. The solvent was distilled off under reduced pressure, and the residue was subjected to silica gel column chromatography to obtain 1.0 g (2.84 mmol) of the present compound (Compound 255) having a melting point of 152.0° C.

Production Example 12

1.41 g (4.67 mmol) of bis(trichloromethyl)carbonate was dissolved in 10 mml of 1,4-dioxane, to which 1.1 g (14 mmol) of pyridine was added dropwise under cooling with water. After stirring at room temperature for 15 minutes, 0.98 g (14 mmol) of 3-butyne-1-ol was added dropwise, and after additional one-hour stirring at room temperature, the reaction solution was filtered to obtain a filtrate. This filtrate is called "filtrate F".

20 ml of toluene was added to a mixture of 2.0 g (7.00 mmol) of an intermediate A (Compound 1007) and 0.59 g (14.0 mmol) of lithium hydroxide monohydrate, and the mixture was refluxed for one hour while removing water by azeotropic dehydration. Toluene was distilled off under reduced pressure, 10 ml of 1,4-dioxane was added, and the filtrate F was added dropwise under reflux. After stirring for 10 minutes under the refluxing condition, 1,4-dioxane was distilled off under reduced pressure. Water was added to the residue, the solution was extracted with ethyl acetate, and the organic layer was washed twice with water. The solvent was distilled off under reduced pressure, and the residue was subjected to silica gel column chromatography to obtain 0.58 g (1.65 mmol) of the present compound (Compound 242) having a melting point of 160.3° C.

Production Example 13

0.98 g (3.29 mmol) of bis(trichloromethyl)carbonate was dissolved in 10 mml of 1,4-dioxane, to which 0.79 g (10 mmol) of pyridine was added dropwise under cooling with water. After stirring at room temperature for 25 minutes, 0.72 g (10 mmol) of 2-butene-1-ol was added dropwise, and after additional 15-minute stirring at room temperature, the reaction solution was filtered to obtain a filtrate. This filtrate is called "filtrate G".

10 ml of toluene was added to a mixture of 1.5 g (5.0 mmol) of an intermediate A (Compound 1020) and 0.42 g (10.0 mmol) of lithium hydroxide monohydrate, and the mixture was refluxed for one hour while removing water by azeotropic dehydration. Toluene was distilled off under reduced pressure, then 10 ml of 1,4-dioxane was added, and the filtrate G was added dropwise under reflux. After further stirring for 10 minutes under the refluxing condition, 1,4-dioxane was distilled off under reduced pressure. Water was added to the residue, the resulting solution was extracted with ethyl acetate, and the organic layer was washed twice with water. The solvent was distilled off under reduced pressure, and the residue was subjected to silica gel column chromatography to obtain 0.47 g (1.18 mmol) of the present compound (Compound 346) having a melting point of 127.7° C.

Production Example 14

20 ml of toluene was added to a mixture of 1.43 g (5.0 mmol) of an intermediate A (Compound 1007) and 0.42 g (10.0 mmol) of lithium hydroxide monohydrate, and the mixture was refluxed for 30 minutes while removing water by azeotropic dehydration. Toluene was distilled off under reduced pressure, 20 ml of 1,4-dioxane was added, and further 1.1 ml (9.1 mmol) of S-ethyl chlorothioformate was added dropwise under reflux. After stirring for 10 minutes under the refluxing condition, 1,4-dioxane was distilled off under reduced pressure. Water was added to the residue, the solution was extracted with ethyl acetate, and the organic layer was washed twice with water. The solvent was distilled off under reduced pressure and the residue was collected and subjected to thin layer chromatography to obtain 0.24 g (0.64 mmol) of the present compound (Compound 411) having a melting point of 177.5° C.

Production Example 15

0.98 g (3.29 mmol) of bis(trichloromethyl)carbonate was dissolved in 10 mml of 1,4-dioxane, to which 0.79 g (10.0 mmmol) of pyridine was added dropwise under cooling with water. After stirring at room temperature for 30 minutes, 1.35 g (10.0 mmol) of 55% 2-propene-1-thiol was added dropwise, and after additional 30-minute stirring at room temperature, the reaction solution was filtered to obtain a filtrate. This filtrate is called "filtrate H".

20 ml of toluene was added to a mixture of 1.41 g (4.93 mmol) of an intermediate A (Compound 1007) and 0.42 g (10.0 mmol) of lithium hydroxide monohydrate, and the mixture was refluxed for 30 minutes while removing water by azeotropic dehydration. Toluene was distilled off under reduced pressure and 10 ml of 1,4-dioxane was added. Then the filtrate H was added dropwise under reflux, and after additional 10-minute stirring under the refluxing condition, 1,4-dioxane was distilled off under reduced pressure. Water was added to the residue, the solution was extracted with ethyl acetate, and the organic layer was washed twice with water. Then the solvent was distilled off under reduced pressure and the residue was subjected to silica gel column chromatography to obtain 0.14 g (0.36 mmol) of the present compound (Compound 463) of m.p. 170.8° C.

Production Example 16

10 ml of toluene was added to a mixture of 1.22 g (5.0 mmol) of an intermediate A (Compound 1017) and 0.42 g (10.0 mmol) of lithium hydroxide monohydrate, and the mixture was refluxed for 30 minutes while removing water by azeotropic dehydration. Toluene was distilled off under reduced pressure, 10 ml of 1,4-dioxane was added and then 1.25 g (10.0 mol) of S-ethyl chlorothioformate was further added dropwise under reflux. After stirring for 30 minutes under the refluxing condition, 1,4-dioxane was distilled off under reduced pressure. Water was added to the residue, this solution was extracted with ethyl acetate, and the organic layer was washed with water. The solvent was distilled off under reduced pressure and the residue was subjected to silica gel column chromatography to obtain 0.14 g (0.42 mmol) of the present compound (Compound 499) of m.p. 137.8° C.

Production Example 17

10 ml of toluene was added to a mixture of 1.20 g (4.9 mmol) of an intermediate A (Compound 1017) and 0.41 g (9.8 mmol) of lithium hydroxide monohydrate, and the mixture was refluxed for 30 minutes while removing water by azeotropic dehydration. Toluene was distilled off under reduced pressure, 10 ml of 1,4-dioxane was added, and then 1.0 g (7.3 mmol) of S-allyl chlorothioformate was added dropwise under reflux. After stirring for 15 minutes under the refluxing condition, 1,4-dioxane was distilled off under reduced pressure and water was added to the residue. The solution was extracted with ethyl acetate and the organic layer was washed with a saline solution. The solvent was distilled off under reduced pressure and the residue was subjected to silica gel column chromatography to obtain 0.09 g (0.26 mmol) of the present compound (Compound 551) of m.p. 146.6° C.

Production Example 18

20 ml of toluene was added to a mixture of 2.2 g (7.7 mmol) of an intermediate A (Compound 1007) and 0.48 g (11.4 mmol) of lithium hydroxide monohydrate, and the mixture was refluxed for one hour while removing water by azeotropic dehydration. Toluene was distilled off under reduced pressure, 20 ml of 1,4-dioxane was added and then 1.46 g (11.7 mmol) of O-ethyl chlorothioformate was added dropwise under reflux. After stirring for 5 minutes under the refluxing condition, 1,4-dioxane was distilled off under reduced pressure and water was added to the residue. The solution was extracted with ethyl acetate and the organic layer was washed with water. The solvent was distilled off under reduced pressure and the residue was subjected to silica gel column chromatography to obtain 0.11 g (0.29 mmol) of the present compound (Compound 621).

$^1$H-NMR (CDCl$_3$, TMS) δ (ppm): 7.38 (1H), 7.20–7.26 (2H), 6.45 (2H), 4.66 (2H). 3.94 (1H), 1.53 (3H), 1.43 (6H).

Production Example 19

60 mg (7.5 mmol) of lithium hydride was added to a solution of an intermediate B (Compound 2147) in a 1.39 g (5 mmol) of a dioxane and the mixture was refluxed for 10 minutes. Then 1.0 g (7.2 mmol) of isopropyl methanesulfonate was added and the mixture was further refluxed for 30 minutes. 1,4-dioxane was distilled off under reduced pressure and water was added to the residue. The solution was extracted with ethyl acetate and the organic layer was washed with water. The solvent was distilled off under reduced pressure and the residue was subjected to silica gel column chromatography to obtain 1.14 g (3.57 mmol) of the present compound (Compound 408).

$^1$H-NMR (CDCl$_3$, TMS) δ (ppm): 7.17–7.24 (4H), 5.5 (2H), 3.91 (1H), 2.95 (2H), 2.26 (3H), 1.43 (6H), 1.36 (3H).

Production Example 20

32 mg (4 mmol) of lithium hydride was added to a dioxane solution of 852 mg (3.08 mmol) of an intermediate B (Compound 2147) and the mixture was refluxed for 10 minutes. Then 570 mg (4.6 mmol) of ethyl methanesulfonate was added and the mixture was refluxed for one hour. 1,4-dioxane was distilled off under reduced pressure and water was added to the residue. The solution was extracted with ethyl acetate and the organic layer was washed with water. The solvent was distilled off under reduced pressure and the residue was washed with an ethyl acetate/hexane mixed solvent to obtain 230 mg (0.75 mmol) of the present compound (Compound 595).

$^1$H-NMR (CDCl$_3$, TMS) δ (ppm): 7.21–7.26 (4H), 5.7 (2H), 3.8 (2H), 2.98 (2H), 2.28 (3H), 1.38 (3H), 1.05 (3H).

Production Example 21

85 mg (10.6 mmol) of lithium hydride was added to a dioxane solution of 2.07 g (6.23 mmol) of an intermediate B (Compound 2150) and the mixture was refluxed for 10 minutes. Then 1.6 g (10.5 mmol) of secondary butyl methanesulfonate was added and the mixture was further refluxed for one hour. 1,4-dioxane was distilled off under reduced pressure and water was added to the residue. The solution was extracted with ethyl acetate and the organic layer was washed with water. The solvent was distilled off under reduced pressure and the residue was washed with an ethyl acetate/hexane mixed solvent to obtain 1.25 g (3.22 mmol) of the present compound (Compound 502).

$^1$H-NMR (CDCl$_3$, TMS) δ (ppm): 7.37 (1H), 7.18–7.26 (2H), 5.63 (2H), 3.63 (1H), 2.97 (2H), 1.88–2.09 (2H), 1.35–1.41 (6H), 1.00 (3H).

Production Example 22

95 mg (12 mmol) of lithium hydride was added to a dioxane solution of 2.0 g (7.2 mmol) of an intermediate B (Compound 2147) and the mixture was refluxed for 10 minutes. Then 1.8 g (11.8 mmol) of (−)-secondary butyl methanesulfonate $\{[\alpha]^{18}_D=-1.42$ (c=7, CHCl$_3$)$\}$ was added and the mixture was further refluxed for one hour. 1,4-dioxane was distilled off under reduced pressure and water was added to the residue. The solution was extracted with ethyl acetate and the organic layer was washed with water. The solvent was distilled off under reduced pressure and the residue was washed with an ethyl acetate/hexane mixed solvent to obtain 1.3 g (3.9 mmol) of the present compound (Compound (+)-499).

$[\alpha]^{18}_D=+0.422$ (c=5.5, CHCl$_3$)

Production Example 23

90 mg (11.3 mmol) of lithium hydride was added to a dioxane solution of 1.93 g (7.0 mmol) of an intermediate B (Compound 2147) and the mixture was refluxed for 10 minutes. Then 1.7 g (11.1 mmol) of (+)-secondary butyl methanesulfonate $\{[\alpha]^{18}_D=+1.49$ (c=7, CHCl$_3$)$\}$ was added and the mixture was further refluxed for one hour. 1,4-dioxane was distilled off under reduced pressure and water was added to the residue. The solution was extracted with ethyl acetate, and the organic layer was washed with water. The solvent was distilled off under reduced pressure and the residue was washed with an ethyl acetate/hexane mixed solvent to obtain 1.0 g (3.0 mmol) of the present compound (Compound (−)-499).

$[\alpha]^{18}_D=-0.389$ (c=5.4, CHCl$_3$)

Production Example 24

77 mg (9.6 mmol) of lithium hydride was added to a dioxane solution of 2.0 g (6.0 mmol) of an intermediate B (Compound 2150) and the mixture was refluxed for 10 minutes. Then 1.5 g (10.0 mmol) of (+)-secondary butyl methanesulfonate $\{[\alpha]^{18}_D=+1.49$ (c=7, CHCl$_3$)$\}$ was added and the mixture was further refluxed for one hour. 1,4-dioxane was distilled off under reduced pressure and water was added to the residue. The solution was extracted with ethyl acetate and the organic layer was washed with water. The solvent was distilled off under reduced pressure and the residue was washed with an ethyl acetate/hexane mixed solvent to obtain 1.1 g (2.8 mmol) of the present compound (Compound (−)-502).

$[\alpha]^{18}_D=-0.98$ (c=8.5, CHCl$_3$)

Production Example 25

70 mg (8.8 mmol) of lithium hydride was added to a dioxane solution of 1.9 g (5.8 mmol) of an intermediate B (Compound 2150) and the mixture was refluxed for 10 minutes. Then 1.4 g (9.2 mmol) of (−)-secondary butyl methanesulfonate $\{[\alpha]^{18}_D=-1.43$ (c=7, CHCl$_3$)$\}$ was added and the mixture was further refluxed for one hour. 1,4-dioxane was distilled off under reduced pressure and water was added to the residue. The solution was extracted with ethyl acetate and the organic layer was washed with water. The solvent was distilled off under reduced pressure and the residue was washed with an ethyl acetate/hexane mixed solvent to obtain 1.1 g (2.8 mmol) of the present compound (Compound (+)-502).

$[\alpha]^{18}_D=+0.90$ (c=8.3, CHCl$_3$)

Example 26

0.50 g (1.52 mmol) of an intermediate B (Compound 2072) was added to a mixture of 0.0242 g (3.04 mmol) of lithium hydride and 10.00 g of dioxane and the mixture was stirred at the same temperature for 30 minutes. Then 0.42 g (3.04 mmol) of isopropyl mesylate was slowly added dropwise, and after the completion of this dropwise addition, the mixture was heated to 100° C. and reacted at the same temperature for 2 hours. After cooling, 10.00 g of a 5% hydrochloric acid solution was added and the mixture was extracted twice with 20.00 g of toluene. The organic layers were joined and dried over magnesium sulfate, and then the solvent was distilled away. The residue was crystallized by adding n-hexane, then filtered, washed with n-hexane and dried to give 0.59 g (LC area metric percentage value: 77.4%) of the present compound (Compound No. 203).

Example 27

0.50 g (1.52 mmol) of an intermediate B (Compound 2072) was added to a mixture of 0.128 g (3.04 mmol) of lithium hydroxide monohydrate and 20.00 g of toluene at room temperature, and the mixture was subjected to azeotropic dehydration by heating under reflux for 2 hours. After cooling, toluene was perfectly distilled away and the residue was dried. To the resulting solid, 10.00 g of dioxane was added, followed by slow dropwise addition of 0.42 g (3.04 mmol) of isopropyl mesylate at room temperature. After the completion of this dropwise addition, the mixture was heated to 100° C. and stirred at the same temperature for 2 hours. Thereafter, the mixture was cooled and, after adding 10.00 g of a 5% hydrochloric acid solution, extracted twice with 20.00 g of toluene. The organic layers were combined and dried over magnesium sulfate, and then the solvent was distilled off. The residue was crystallized by adding n-hexane, then filtered, washed with n-hexane and dried to obtain 0.45 g (LC area metric percentage value: 64.6%) of the present compound (Compound 203).

Example 28

0.50 g (1.51 mmol) of an intermediate B (Compound 2150) was added to a mixture of 0.0239 g (3.02 mmol) of lithium hydride and 10.00 g of dioxane at room temperature and stirred at the same temperature for 30 minutes. Then 0.42 g (3.02 mmol) of isopropyl mesylate was slowly added dropwise, after which the mixture was heated to 100° C. and stirred at the same temperature for 2 hours. Then the mixture was cooled and, after adding 10.00 g of a 5% hydrochloric acid solution, extracted twice with 20.00 g of toluene. The organic layers were combined and dried over magnesium sulfate. The solvent was distilled off and the residue was subjected to silica gel column chromatography to obtain 0.42 g (LC areametric percentage value: 95.9%) of the present compound (Compound 411).

Example 29

0.50 g (1.80 mmol) of an intermediate B (Compound 2147) was added to a mixture of 0.0287 g (3.60 mmol) of lithium hydride and 10.00 g of dioxane, and the mixture was stirred at the same temperature for 30 minutes. Then 0.55 g (3.60 mmol) of sec-butyl mesylate was slowly added dropwise, which was followed by heating to 100° C. and stirring at the same temperature for 2 hours. The mixture was then cooled and, after adding 10.00 g of a 5% hydrochloric acid solution, extracted twice with 20.00 g of toluene. The organic layers were combined and dried over magnesium sulfate, after which the solvent was distilled off and the residue was subjected to silica gel column chromatography to obtain 0.42 g (LC areametric percentage value: 99.2%) of the present compound (Compound 499).

Example 30

0.50 g (1.80 mmol) of an intermediate B (Compound 2147) was added to a mixture of 0.0871 g (2.07 mmol) of lithium hydroxide monohydrate and 20.00 g of toluene at a room temperature and the mixture was subjected to azeotropic dehydration by heating under reflux for 2 hours. After cooling, toluene was perfectly distilled off and the residue was dried. To the resulting solid, 2.50 g of dioxane was added and then 0.38 g (2.43 mmol) of sec-butyl mesylate was slowly added dropwise at room temperature, after which the mixture was heated to 100° C. and stirred at the same temperature for 3 hours. The solution was cooled and, after adding 10.00 g of a 5% hydrochloric acid solution, extracted twice with 20.00 g of toluene. The organic layers were combined and dried over magnesium sulfate, and the solvent was distilled off. The residue was crystallized by adding n-hexane, then filtered, washed with n-hexane and dried to obtain 0.44 g (LC areametric percentage value: 93.5%) of the present compound (Compound 499).

Example 31

A mixture of 0.0871 g (2.07 mmol) of lithium hydroxide monohydrate, 0.50 g (1.80 mmol) of an intermediate B (Compound 2147) and 2.50 g of dioxane was heated to 100° C. Then 0.37 g (2.43 mmol) of sec-butyl mesylate was slowly added dropwise at the same temperature, after which the mixture was stirred at the same temperature for 4 hours. The solution was cooled and, after adding 10.00 g of a 5% hydrochloric acid solution, extracted twice with 20.00 g of toluene. The organic layers were combined and dried over magnesium sulfate, and the solvent was distilled off. The residue was crystallized by adding n-hexane, then filtered, washed with n-hexane and dried to obtain 0.42 g (LC areametric percentage value: 98.4%) of the present compound (Compound 499).

Example 32

A mixture of 0.0871 g (2.07 mmol) of lithium hydroxide monohydrate, 0.50 g (1.80 mmol) of an intermediate B (Compound 2147), 0.50 g of molecular sieves 3A and 2.50 g of dioxane was heated to 100° C., to which 0.37 g (2.43 mmol) of sec-butyl mesylate was slowly added dropwise at the same temperature. After the completion of dropwise addition, the mixture was stirred at the same temperature for 4 hours, then cooled and, after adding 10.00 g of a 5% hydrochloric acid solution, extracted twice with 20.00 g of toluene. The organic layers were combined and dried over magnesium sulfate, and then the solvent was distilled off. The residue was crystallized by adding n-hexane, then filtered, washed with n-hexane and dried to obtain 0.45 g (LC areametric percentage value: 99.1%) of the present compound (Compound 499).

Example 33

A mixture of 1.00 g (3.60 mmol) of an intermediate B (Compound 2147), 0.50 g of molecular sieves 3A, 0.74 g (4.86 mmol) of sec-butyl mesylate and 5.00 g of dioxane was heated to 90° C., to which 0.174 g (4.14 mmol) of lithium hydroxide monohydrate was added in three portions over a period of 2 hours. Thereafter, the mixture was stirred at the same temperature for 5 hours, then cooled and, after adding 20.00 g of a 5% hydrochloric acid solution, extracted twice with 40.00 g of toluene. The organic layers were combined and dried over magnesium sulfate, and the solvent was distilled off. The residue was crystallized by adding n-hexane, then filtered, washed with n-hexane and dried to obtain 0.95 g (LC areameetric percentage value: 97.8%) of the present compound (Compound 499).

Example 34

0.50 g (1.90 mmol) of an intermediate B (Compound 2017) was added to a mixture of 0.0305 g (3.80 mmol) of lithium hydride and 10.00 g of dioxane at room temperature, and the mixture was stirred at the same temperature for 30 minutes. Then 0.58 g (3.80 mmol) of sec-butyl mesylate was slowly added dropwise, followed by heating to 100° C. and stirring at the same temperature for 4 hours. The solution was cooled and, after adding 10.00 g of a 5% hydrochloric acid solution, extracted twice with 20.00 g of toluene. The formed organic layers were combined and dried over magnesium sulfate, and the solvent was distilled off. The residue was crystallized by adding n-hexane, filtered, washed with n-hexane and dried to give 0.25 g (LC areametric percentage value: 95.2%) of the present compound (Compound 278) of m.p. 70.0° C.

Production Example 35

300 ml of 3N hydrochloric acid and 100 ml of ethanol were added to 107 g (313 mmol) of 3-amino-2-tert-butyl-1-isopropyl-4-(2,6-dichlorophenyl)-3-pyrazoline-5-one and stirred under the refluxing condition for 4 hours. Then ethanol was distilled off under reduced pressure and the aqueous layer was neutralized with a dilute sodium oxide solution. The precipitated solid was filtered out, washed with water and ethyl acetate, and dried in vacuo to obtain 88.4 g (309 mmol) of an intermediate A (Compound 1007).

$^1$H-NMR (CD$_3$OD, TMS) δ (ppm): 7.47 (1H), 7.33–7.36 (2H), 4.93 (2H), 4.41 (1H), 1.30 (6H).

Production Example 36

300 ml of 3N hydrochloric acid and 100 ml of ethanol were added to 54.6 g (181 mmol) of 3-amino-2-tert-butyl-1-sec-butyl-4-(2-methylphenyl)-3-pyrazoline-5-one and stirred under the refluxing condition for 4 hours. Then ethanol was distilled off under reduced pressure and the aqueous layer was neutralized with a sodium bicarbonate solution, and the precipitated solid was filtered out, washed with water and ethyl acetate, and dried in vacuo to obtain 35.3 g (144 mmol) of an intermediate A (Compound 1017).

$^1$H-NMR (CD$_3$OD, TMS) δ (ppm): 7.17 (4H), 4.83 (2H), 4.1 (1H), 2.25 (3H), 1.5–1.9 (2H), 1.21 (3H), 0.94 (3H).

Production Example 37

5.19 g (27.5 mmol) of 3-amino-4-(2-methylphenyl)-3-pyrazoline-5-one and 11.1 g (110 mmol) of triethylamine were suspended in tetrahydrofuran, to which 2.5 g (30.7 mmol) of chlorotrimethylsilane was added dropwise under cooling with ice-water. Then 3.7 g (30.7 mmol) of allyl chloroformate was added dropwise under cooling with ice-water. The mixture was stirred at room temperature for one hour and the formed precipitate was filtered out. 8 ml of water and 8 ml (140 mmol) of acetic acid were added to the filtrate and refluxed for 30 minutes. The reaction solution was cooled to room temperature and, after adding water, extracted with ethyl acetate, and the organic layer was washed with water. The solvent was distilled off under reduced pressure, and the residue was subjected to silica gel column chromatography to obtain 1.4 g (5.1 mmol) of an intermediate B (compound 2069). M.p. 187.4° C.

Example 38

59.02 g (0.148 mol) of a 10% sodium hydroxide solution was slowly added dropwise to a mixture of 30.00 g (0.123 mol) of 3-amino-4-(2,6-dichlorophenyl)-3-pyrazoline-5-one, 15.56 g (0.129 mol) of allyl chloroformate and 150.00 g of toluene at 25° C., after which the mixture was stirred at the same temperature for 2 hours. Then the mixture was made acid by adding a 5% hydrochloric acid solution and the precipitated crystals were filtered out, washed with 30.00 g of toluene and dried to obtain 36.84 g (LC areametric percentage value: 99.1%) of an intermediate B (Compound 2072) of m.p. 169.0° C.

Example 39

39.34 g (98.36 mmol) of a 10% sodium hydroxide solution was slowly added dropwise to a mixture of 20.00 g (81.97 mmol) of 3-amino-4-(2,6-dichlorophenyl)-3-pyrazoline-5-one, 10.72 g (86.07 mmol) of S-ethyl chlorothioformate and 100.00 g of toluene at 25° C. After the completion of dropwise addition, the mixture was stirred at the same temperature for 2 hours. Then the reaction mixture was made acid by adding a 5% hydrochloric acid solution and extracted with toluene and methyl tert-butyl ether. The organic layer was concentrated and the residue was subjected to silica gel column chromatography to obtain 19.16 g (LC areametric percentage value: 98.4%) of an intermediate B (Compound 2150) of m.p. 198.5° C.

Example 40

1.27 g (3.18 mmol) of a 10% sodium hydroxide solution was slowly added dropwise to a mixture of 0.50 g (2.65 mmol) of 3-amino-4-(2-methylphenyl)-3-pyrazoline-5-one, 0.33 g (2.78 mmol) of allyl chloroformate and 2.50 g of toluene at 25° C., after which the mixture was stirred at the same temperature for one hour. Then the reaction mixture was made acid by adding a 5% hydrochloric acid solution and extracted with toluene and methyl tert-butyl ether. The solvent was concentrated and the residue was subjected to silica gel column chromatography to obtain 0.56 g (LC areametric percentage value: 99.6%) of an intermediate B (Compound 2069).

Example 41

50.79 g (0.127 mol) of a 10% sodium hydroxide solution was slowly added dropwise to a mixture of 20.00 g (0.106 mol) of 3-amino-4-(2-methylphenyl)-3-pyrazoline-5-one, 13.84 g (0.111 mol) of S-ethyl chlorothioformate and 100.00 g of toluene at 25° C., after which the mixture was stirred at the same temperature for one hour. Then the reaction mixture was made acid by adding a 5% hydrochloric acid solution and extracted twice with 40.00 g of ethyl acetate. The organic layers were combined and dried over magnesium sulfate. The solvent was concentrated and the residue was subjected to silica gel column chromatography. After additional concentration, the residue was washed with 200 ml of a 1/9 ethyl acetate/n-hexane mixed solution and dried to obtain 24.39 g (LC areametric percentage value: 98.5%) of an intermediate B (Compound 2147) of m.p. 172.5° C.

Example 42

5.08 g (12.7 mmol) of a 10% sodium hydroxide solution was slowly added dropwise to a mixture of 2.00 g (10.6 mmol) of 3-amino-4-(2-methylphenyl)-3-pyrazoline-5-one, 1.21 g (11.1 mmol) of ethyl chloroformate and 10.00 g of toluene at 25° C., after which the mixture was stirred at the same temperature for one hour. Then the reaction mixture was made acid by adding a 5% hydrochloric acid solution and extracted twice with 10.00 g of ethyl acetate. The organic layers were combined and dried over magnesium sulfate, the solvent was concentrated and the residue was subjected to silica gel column chromatography to obtain 2.10 g (LC areametric percentage value: 98.9%) of an intermediate B (Compound 2017) of m.p. 161.5° C.

Examples of the present compounds are shown with Compound No. in Tables 1 to 41.

The compounds represented by the formula:

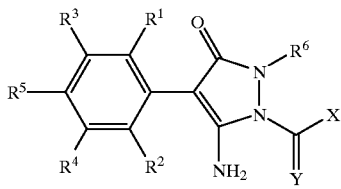

TABLE 1

| Compound No. | $R^1, R^2, R^3, R^4, R^5$ | $R^6$ | X |
|---|---|---|---|
| 1 | 2-F | iPr | Me |
| 2 | 2-Cl | iPr | Me |
| 3 | 2-Br | iPr | Me |
| 4 | 2,6-F$_2$ | iPr | Me |
| 5 | 2,6-Cl$_2$ | iPr | Me |
| 6 | 2-F, 6-Cl | iPr | Me |
| 7 | 2,3,5-Cl$_3$ | iPr | Me |
| 8 | 2-CF$_3$ | iPr | Me |
| 9 | 2-CH$_3$ | iPr | Me |
| 10 | 2-OCH$_3$ | iPr | Me |
| 11 | 2,6-(CH$_3$)$_2$ | iPr | Me |
| 12 | 2-Cl, 6-CH$_3$ | iPr | Me |
| 13 | 2-F, 6-CH$_3$ | iPr | Me |
| 14 | 2-F | iPr | Et |
| 15 | 2-Cl | iPr | Et |
| 16 | 2-Br | iPr | Et |
| 17 | 2,6-F$_2$ | iPr | Et |
| 18 | 2,6-Cl$_2$ | iPr | Et |
| 19 | 2-F, 6-Cl | iPr | Et |
| 20 | 2,3,5-Cl$_3$ | iPr | Et |
| 21 | 2-CF$_3$ | iPr | Et |
| 22 | 2-CH$_3$ | iPr | Et |
| 23 | 2-OCH$_3$ | iPr | Et |
| 24 | 2,6-(CH$_3$)$_2$ | iPr | Et |
| 25 | 2-Cl, 6-CH$_3$ | iPr | Et |

TABLE 2

| Compound No. | $R^1, R^2, R^3, R^4, R^5$ | $R^6$ | X |
|---|---|---|---|
| 26 | 2-F, 6-CH$_3$ | iPr | Et |
| 27 | 2-F | iPr | nPr |
| 28 | 2-Cl | iPr | nPr |
| 29 | 2-Br | iPr | nPr |
| 30 | 2,6-F$_2$ | iPr | nPr |
| 31 | 2,6-Cl$_2$ | iPr | nPr |
| 32 | 2-F, 6-Cl | iPr | nPr |
| 33 | 2,3,5-Cl$_3$ | iPr | nPr |
| 34 | 2-CF$_3$ | iPr | nPr |
| 35 | 2-CH$_3$ | iPr | nPr |
| 36 | 2-OCH$_3$ | iPr | nPr |
| 37 | 2,6-(CH$_3$)$_2$ | iPr | nPr |
| 38 | 2-Cl, 6-CH$_3$ | iPr | nPr |
| 39 | 2-F, 6-CH$_3$ | iPr | nPr |
| 40 | 2-F | iPr | nBu |
| 41 | 2-Cl | iPr | nBu |
| 42 | 2-Br | iPr | nBu |
| 43 | 2,6-F$_2$ | iPr | nBu |
| 44 | 2,6-Cl$_2$ | iPr | nBu |
| 45 | 2-F, 6-Cl | iPr | nBu |
| 46 | 2,3,5-Cl$_3$ | iPr | nBu |
| 47 | 2-CF$_3$ | iPr | nBu |
| 48 | 2-CH$_3$ | iPr | nBu |
| 49 | 2-OCH$_3$ | iPr | nBu |
| 50 | 2,6-(CH$_3$)$_2$ | iPr | nBu |

TABLE 3

| Compound No. | $R^1, R^2, R^3, R^4, R^5$ | $R^6$ | X |
|---|---|---|---|
| 51 | 2-Cl, 6-CH$_3$ | iPr | nBu |
| 52 | 2-F, 6-CH$_3$ | iPr | nBu |
| 53 | 2-F | iPr | nPen |
| 54 | 2-Cl | iPr | nPen |
| 55 | 2-Br | iPr | nPen |
| 56 | 2,6-F$_2$ | iPr | nPen |
| 57 | 2,6-Cl$_2$ | iPr | nPen |
| 58 | 2-F, 6-Cl | iPr | nPen |
| 59 | 2,3,5-Cl$_3$ | iPr | nPen |
| 60 | 2-CF$_3$ | iPr | nPen |
| 61 | 2-CH$_3$ | iPr | nPen |
| 62 | 2-OCH$_3$ | iPr | nPen |
| 63 | 2,6-(CH$_3$)$_2$ | iPr | nPen |
| 64 | 2-Cl, 6-CH$_3$ | iPr | nPen |
| 65 | 2-F, 6-CH$_3$ | iPr | nPen |
| 66 | 2-F | sBu | Me |
| 67 | 2-Cl | sBu | Me |
| 68 | 2-Br | sBu | Me |
| 69 | 2,6-F$_2$ | sBu | Me |
| 70 | 2,6-Cl$_2$ | sBu | Me |
| 71 | 2-F, 6-Cl | sBu | Me |
| 72 | 2,3,5-Cl$_3$ | sBu | Me |
| 73 | 2-CF$_3$ | sBu | Me |
| 74 | 2-CH$_3$ | sBu | Me |
| 75 | 2-OCH$_3$ | sBu | Me |

TABLE 4

| Compound No. | $R^1, R^2, R^3, R^4, R^5$ | $R^6$ | X |
|---|---|---|---|
| 76 | 2,6-(CH$_3$)$_2$ | sBu | Me |
| 77 | 2-Cl, 6-CH$_3$ | sBu | Me |
| 78 | 2-F, 6-CH$_3$ | sBu | Me |
| 79 | 2-F | sBu | Et |
| 80 | 2-Cl | sBu | Et |
| 81 | 2-Br | sBu | Et |
| 82 | 2,6-F$_2$ | sBu | Et |
| 83 | 2,6-Cl$_2$ | sBu | Et |
| 84 | 2-F, 6-Cl | sBu | Et |
| 85 | 2,3,5-Cl$_3$ | sBu | Et |
| 86 | 2-CF$_3$ | sBu | Et |
| 87 | 2-CH$_3$ | sBu | Et |
| 88 | 2-OCH$_3$ | sBu | Et |
| 89 | 2,6-(CH$_3$)$_2$ | sBu | Et |
| 90 | 2-Cl, 6-CH$_3$ | sBu | Et |
| 91 | 2-F, 6-CH$_3$ | sBu | Et |
| 92 | 2-F | sBu | nPr |
| 93 | 2-Cl | sBu | nPr |
| 94 | 2-Br | sBu | nPr |
| 95 | 2-CF$_3$ | sBu | nPr |
| 96 | 2-CH$_3$ | sBu | nPr |
| 97 | 2-OCH$_3$ | sBu | nPr |
| 98 | 2,6-F$_2$ | sBu | nPr |
| 99 | 2,6-Cl$_2$ | sBu | nPr |
| 100 | 2,6-(CH$_3$)$_2$ | sBu | nPr |

TABLE 5

| Compound No. | $R^1, R^2, R^3, R^4, R^5$ | $R^6$ | X |
|---|---|---|---|
| 101 | 2-F, 6-Cl | sBu | nPr |
| 102 | 2,3,5-Cl$_3$ | sBu | nPr |
| 103 | 2-Cl, 6-CH$_3$ | sBu | nPr |
| 104 | 2-F, 6-CH$_3$ | sBu | nPr |
| 105 | 2-F | sBu | nBu |
| 106 | 2-Cl | sBu | nBu |
| 207 | 2-Br | sBu | nBu |
| 108 | 2-CF$_3$ | sBu | nBu |
| 109 | 2-CH$_3$ | sBu | nBu |

TABLE 5-continued

| Compound No. | $R^1, R^2, R^3, R^4, R^5$ | $R^6$ | X |
|---|---|---|---|
| 110 | 2-OCH$_3$ | sBu | nBu |
| 111 | 2,6-F$_2$ | sBu | nBu |
| 112 | 2,6-Cl$_2$ | sBu | nBu |
| 113 | 2,6-(CH$_3$)$_2$ | sBu | nBu |
| 114 | 2-F, 6-Cl | sBu | nBu |
| 115 | 2,3,5-Cl$_3$ | sBu | nBu |
| 116 | 2-Cl, 6-CH$_3$ | sBu | nBu |
| 117 | 2-F, 6-CH$_3$ | sBu | nBu |
| 118 | 2-F | sBu | nPen |
| 119 | 2-Cl | sBu | nPen |
| 120 | 2-Br | sBu | nPen |
| 121 | 2-CF$_3$ | sBu | nPen |
| 122 | 2-CH$_3$ | sBu | nPen |
| 123 | 2-OCH$_3$ | sBu | nPen |
| 124 | 2,6-F$_2$ | sBu | nPen |
| 125 | 2,6-Cl$_2$ | sBu | nPen |

TABLE 6

| Compound No. | $R^1, R^2, R^3, R^4, R^5$ | $R^6$ | X |
|---|---|---|---|
| 126 | 2,6-(CH$_3$)$_2$ | sBu | nPen |
| 127 | 2-F, 6-Cl | sBu | nPen |
| 128 | 2,3,5-Cl$_3$ | sBu | nPen |
| 129 | 2-Cl, 6-CH$_3$ | sBu | nPen |
| 130 | 2-F, 6-CH$_3$ | sBu | nPen |
| 131 | 2-F | iPr | O-Me |
| 132 | 2-Cl | iPr | O-Me |
| 133 | 2-Br | iPr | O-Me |
| 134 | 2-CF$_3$ | iPr | O-Me |
| 135 | 2-CH$_3$ | iPr | O-Me |
| 136 | 2-OCH$_3$ | iPr | O-Me |
| 137 | 2,6-F$_2$ | iPr | O-Me |
| 138 | 2,6-Cl$_2$ | iPr | O-Me |
| 139 | 2,6-(CH$_3$)$_2$ | iPr | O-Me |
| 140 | 2-F, 6-Cl | iPr | O-Me |
| 141 | 2,3,5-Cl$_3$ | iPr | O-Me |
| 142 | 2-Cl, 6-CH$_3$ | iPr | O-Ne |
| 143 | 2-F, 6-CH$_3$ | iPr | O-Me |
| 144 | 2-F | iPr | O-Et |
| 145 | 2-Cl | iPr | O-Et |
| 146 | 2-Br | iPr | O-Et |
| 147 | 2-CF$_3$ | iPr | O-Et |
| 148 | 2-CH$_3$ | iPr | O-Et |
| 149 | 2-OCH$_3$ | iPr | O-Et |
| 150 | 2,6-F$_2$ | iPr | O-Et |

TABLE 7

| Compound No. | $R^1, R^2, R^3, R^4, R^5$ | $R^6$ | X |
|---|---|---|---|
| 151 | 2,6-Cl$_2$ | iPr | O-Et |
| 152 | 2,6-(CH$_3$)$_2$ | iPr | O-Et |
| 153 | 2-F, 6-Cl | iPr | O-Et |
| 154 | 2,3,5-Cl$_3$ | iPr | O-Et |
| 155 | 2-Cl, 6-CH$_3$ | iPr | O-Et |
| 156 | 2-F, 6-CH$_3$ | iPr | O-Et |
| 157 | 2-F | iPr | O-nPr |
| 158 | 2-Cl | iPr | O-nPr |
| 159 | 2-Br | iPr | O-nPr |
| 160 | 2-CF$_3$ | iPr | O-nPr |
| 161 | 2-CH$_3$ | iPr | O-nPr |
| 162 | 2-OCH$_3$ | iPr | O-nPr |
| 163 | 2,6-F$_2$ | iPr | O-nPr |
| 164 | 2,6-Cl$_2$ | iPr | O-nPr |
| 165 | 2,6-(CH$_3$)$_2$ | iPr | O-nPr |
| 166 | 2-F, 6-Cl | iPr | O-nPr |
| 167 | 2,3,5-Cl$_3$ | iPr | O-nPr |
| 168 | 2-Cl, 6-CH$_3$ | iPr | O-nPr |

TABLE 7-continued

| Compound No. | R¹, R², R³, R⁴, R⁵ | R⁶ | X |
|---|---|---|---|
| 169 | 2-F, 6-CH₃ | iPr | O-nPr |
| 170 | 2-F | iPr | O-nBu |
| 171 | 2-Cl | iPr | O-nBu |
| 172 | 2-Br | iPr | O-nBu |
| 173 | 2-CF₃ | iPr | O-nBu |
| 174 | 2-CH₃ | iPr | O-nBu |
| 175 | 2-OCH₃ | iPr | O-nBu |

TABLE 8

| Compound No. | R¹, R², R³, R⁴, R⁵ | R⁶ | X |
|---|---|---|---|
| 176 | 2,6-F₂ | iPr | O-nBu |
| 177 | 2,6-Cl₂ | iPr | O-nBu |
| 178 | 2,6-(CH₃)₂ | iPr | O-nBu |
| 179 | 2-F, 6-Cl | iPr | O-nBu |
| 180 | 2,3,5-Cl₃ | iPr | O-nBu |
| 181 | 2-Cl, 6-CH₃ | iPr | O-nBu |
| 182 | 2-F, 6-CH₃ | iPr | O-nBu |
| 183 | 2-F | iPr | O-iBu |
| 184 | 2-Cl | iPr | O-iBu |
| 185 | 2-Br | iPr | O-iBu |
| 186 | 2-CF₃ | iPr | O-iBu |
| 187 | 2-CH₃ | iPr | O-iBu |
| 188 | 2-OCH₃ | iPr | O-iBu |
| 189 | 2,6-F₂ | iPr | O-iBu |
| 190 | 2,6-Cl₂ | iPr | O-iBu |
| 191 | 2,6-(CH₃)₂ | iPr | O-iBu |
| 192 | 2-F, 6-Cl | iPr | O-iBu |
| 193 | 2,3,5-Cl₃ | iPr | O-iBu |
| 194 | 2-Cl, 6-CH₃ | iPr | O-iBu |
| 195 | 2-F, 6-CH₃ | iPr | O-iBu |
| 196 | 2-F | iPr | O-Allyl |
| 197 | 2-Cl | iPr | O-Allyl |
| 198 | 2-Br | iPr | O-Allyl |
| 199 | 2-CF₃ | iPr | O-Allyl |
| 200 | 2-CH₃ | iPr | O-Allyl |

TABLE 9

| Compound No. | R¹, R², R³, R⁴, R⁵ | R⁶ | X |
|---|---|---|---|
| 201 | 2-OCH₃ | iPr | O-Allyl |
| 202 | 2,6-F | iPr | O-Allyl |
| 203 | 2,6-Cl₂ | iPr | O-Allyl |
| 204 | 2,6-(CH₃)₂ | iPr | O-Allyl |
| 205 | 2-F, 6-Cl | iPr | O-Allyl |
| 206 | 2,3,5-Cl₃ | iPr | O-Allyl |
| 207 | 2-Cl, 6-CH₃ | iPr | O-Allyl |
| 208 | 2-F, 6-CH₃ | iPr | O-Allyl |
| 209 | 2-F | iPr | OCH₂-Allyl |
| 210 | 2-Cl | iPr | OCH₂-Allyl |
| 211 | 2-Br | iPr | OCH₂-Allyl |
| 212 | 2-CF₃ | iPr | OCH₂-Allyl |
| 213 | 2-CH₃ | iPr | OCH₂-Allyl |
| 214 | 2-OCH₃ | iPr | OCH₂-Allyl |
| 215 | 2,6-F₂ | iPr | OCH₂-Allyl |
| 216 | 2,6-Cl₂ | iPr | OCH₂-Allyl |
| 217 | 2,6-(CH₃)₂ | iPr | OCH₂-Allyl |
| 218 | 2-F, 6-Cl | iPr | OCH₂-Allyl |
| 219 | 2,3,5-Cl₃ | iPr | OCH₂-Allyl |
| 220 | 2-Cl, 6-CH₃ | iPr | OCH₂-Allyl |
| 221 | 2-F, 6-CH₃ | iPr | OCH₂-Allyl |
| 222 | 2-F | iPr | OCH₂C≡CH |
| 223 | 2-Cl | iPr | OCH₂C≡CH |
| 224 | 2-Br | iPr | OCH₂C≡CH |
| 225 | 2-CF₃ | iPr | OCH₂C≡CH |

TABLE 10

| Compound No. | R¹, R², R³, R⁴, R⁵ | R⁶ | X |
|---|---|---|---|
| 226 | 2-CH₃ | iPr | OCH₂C≡CH |
| 227 | 2-OCH₃ | iPr | OCH₂C≡CH |
| 228 | 2,6-F₂ | iPr | OCH₂C≡CH |
| 229 | 2,6-Cl₂ | iPr | OCH₂C≡CH |
| 230 | 2,6-(CH₃)₂ | iPr | OCH₂C≡CH |
| 231 | 2-F, 6-Cl | iPr | OCH₂C≡CH |
| 232 | 2,3,5-Cl₃ | iPr | OCH₂C≡CH |
| 233 | 2-Cl, 6-CH₃ | iPr | OCH₂C≡CH |
| 234 | 2-F, 6-CH₃ | iPr | OCH₂C≡CH |
| 235 | 2-F | iPr | OCH₂CH₂C≡CH |
| 236 | 2-Cl | iPr | OCH₂CH₂C≡CH |
| 237 | 2-Br | iPr | OCH₂CH₂C≡CH |
| 238 | 2-CF₃ | iPr | OCH₂CH₂C≡CH |
| 239 | 2-CH₃ | iPr | OCH₂CH₂C≡CH |
| 240 | 2-OCH₃ | iPr | OCH₂CH₂C≡CH |
| 241 | 2,6-F₂ | iPr | OCH₂CH₂C≡CH |
| 242 | 2,6-Cl₂ | iPr | OCH₂CH₂C≡CH |
| 243 | 2,6-(CH₃)₂ | iPr | OCH₂CH₂C≡CH |
| 244 | 2-F, 6-Cl | iPr | OCH₂CH₂C≡CH |
| 245 | 2,3,5-Cl₃ | iPr | OCH₂CH₂C≡CH |
| 246 | 2-Cl, 6-CH₃ | iPr | OCH₂CH₂C≡CH |
| 247 | 2-F, 6-CH₃ | iPr | OCH₂CH₂C≡CH |
| 248 | 2-F | iPr | OCH₂C≡CCH₃ |
| 249 | 2-Cl | iPr | OCH₂C≡CCH₃ |
| 250 | 2-Br | iPr | OCH₂C≡CCH₃ |

TABLE 11

| Compound No. | R¹, R², R³, R⁴, R⁵ | R⁶ | X |
|---|---|---|---|
| 251 | 2-CF₃ | iPr | OCH₂C≡CCH₃ |
| 252 | 2-CH₃ | iPr | OCH₂C≡CCH₃ |
| 253 | 2-OCH₃ | iPr | OCH₂C≡CCH₃ |
| 254 | 2,6-F₂ | iPr | OCH₂C≡CCH₃ |
| 255 | 2,6-Cl₂ | iPr | OCH₂C≡CCH₃ |
| 256 | 2-F, 6-Cl | iPr | OCH₂C≡CCH₃ |
| 257 | 2,3,5-Cl₃ | iPr | OCH₂C≡CCH₃ |
| 258 | 2-Cl, 6-CH₃ | iPr | OCH₂C≡CCH₃ |
| 259 | 2-F, 6-CH₃ | iPr | OCH₂C≡CCH₃ |
| 260 | 2,6-(CH₃)₂ | iPr | OCH₂C≡CCH₃ |
| 261 | 2-F | sBu | O-Me |
| 262 | 2-Cl | sBu | O-Me |
| 263 | 2-Br | sBu | O-Me |
| 264 | 2-CF₃ | sBu | O-Me |
| 265 | 2-CH₃ | sBu | O-Me |
| 266 | 2-OCH₃ | sBu | O-Ne |
| 267 | 2,6-F₂ | sBu | O-Me |
| 268 | 2,6-Cl₂ | sBu | O-Me |
| 269 | 2,6-(CH₃)₂ | sBu | O-Me |
| 270 | 2-F, 6-Cl | sBu | O-Me |
| 271 | 2,3,5-Cl₃ | sBu | O-Me |
| 272 | 2-Cl, 6-CH₃ | sBu | O-Me |
| 273 | 2-F, 6-CH₃ | sBu | O-Me |
| 274 | 2-F | sBu | O-Et |
| 275 | 2-Cl | sBu | O-Et |

TABLE 12

| Compound No. | R¹, R², R³, R⁴, R⁵ | R⁶ | X |
|---|---|---|---|
| 276 | 2-Br | sBu | O-Et |
| 277 | 2-CF₃ | sBu | O-Et |
| 278 | 2-CH₃ | sBu | O-Et |
| 279 | 2-OCH₃ | sBu | O-Et |
| 280 | 2,6-F₂ | sBu | O-Et |
| 281 | 2,6-Cl₂ | sBu | O-Et |
| 282 | 2,6-(CH₃)₂ | sBu | O-Et |
| 283 | 2-F, 6-Cl | sBu | O-Et |
| 284 | 2,3,5-Cl₃ | sBu | O-Et |

TABLE 12-continued

| Compound No. | $R^1, R^2, R^3, R^4, R^5$ | $R^6$ | X |
|---|---|---|---|
| 285 | 2-Cl, 6-CH$_3$ | sBu | O-Et |
| 286 | 2-F, 6-CH$_3$ | sBu | O-Et |
| 287 | 2-F | sBu | O-nPr |
| 288 | 2-Cl | sBu | O-nPr |
| 289 | 2-Br | sBu | O-nPr |
| 290 | 2-CF$_3$ | sBu | O-nPr |
| 291 | 2-CH$_3$ | sBu | O-nPr |
| 292 | 2-OCH$_3$ | sBu | O-nPr |
| 293 | 2,6-F$_2$ | sBu | O-nPr |
| 294 | 2,6-Cl$_2$ | sBu | O-nPr |
| 295 | 2,6-(CH$_3$)$_2$ | sBu | O-nPr |
| 296 | 2-F, 6-Cl | sBu | O-nPr |
| 297 | 2,3,5-Cl$_3$ | sBu | O-nPr |
| 298 | 2-Cl, 6-CH$_3$ | sBu | O-nPr |
| 299 | 2-F, 6-CH$_3$ | sBu | O-nPr |
| 300 | 2-F | sBu | O-nBu |

TABLE 13

| Compound No. | $R^1, R^2, R^3, R^4, R^5$ | $R^6$ | X |
|---|---|---|---|
| 301 | 2-Cl | sBu | O-nBu |
| 302 | 2-Br | sBu | O-nBu |
| 303 | 2-CF$_3$ | sBu | O-nBu |
| 304 | 2-CH$_3$ | sBu | O-nBu |
| 305 | 2-OCH$_3$ | sBu | O-nBu |
| 306 | 2,6-F$_2$ | sBu | O-nBu |
| 307 | 2,6-Cl$_2$ | sBu | O-nBu |
| 308 | 2,6-(CH$_3$)$_2$ | sBu | O-nBu |
| 309 | 2-F, 6-Cl | sBu | O-nBu |
| 310 | 2,3,5-Cl$_3$ | sBu | O-nBu |
| 311 | 2-Cl, 6-CH$_3$ | sBu | O-nBu |
| 312 | 2-F, 6-CH$_3$ | sBu | O-nBu |
| 313 | 2-F | sBu | O-iBu |
| 314 | 2-Cl | sBu | O-iBu |
| 315 | 2-Br | sBu | O-iBu |
| 316 | 2-CF$_3$ | sBu | O-iBu |
| 317 | 2-CH$_3$ | sBu | O-iBu |
| 318 | 2-OCH$_3$ | sBu | O-iBu |
| 319 | 2,6-F$_2$ | sBu | O-iBu |
| 320 | 2,6-Cl$_2$ | sBu | O-iBu |
| 321 | 2,6-(CH$_3$)$_2$ | sBu | O-iBu |
| 322 | 2-F, 6-Cl | sBu | O-iBu |
| 323 | 2,3,5-Cl$_3$ | sBu | O-iBu |
| 324 | 2-Cl, 6-CH$_3$ | sBu | O-iBu |
| 325 | 2-F, 6-CH$_3$ | sBu | O-iBu |

TABLE 14

| Compound No. | $R^1, R^2, R^3, R^4, R^5$ | $R^6$ | X |
|---|---|---|---|
| 326 | 2-F | sBu | O-Allyl |
| 327 | 2-Cl | sBu | O-Allyl |
| 328 | 2-Br | sBu | O-Allyl |
| 329 | 2-CF$_3$ | sBu | O-Allyl |
| 330 | 2-CH$_3$ | sBu | O-Allyl |
| 331 | 2-OCH$_3$ | sBu | O-Allyl |
| 332 | 2,6-F$_2$ | sBu | O-Allyl |
| 333 | 2,6-Cl$_2$ | sBu | O-Allyl |
| 334 | 2,6-(CH$_3$)$_2$ | sBu | O-Allyl |
| 335 | 2-F, 6-Cl | sBu | O-Allyl |
| 336 | 2,3,5-Cl$_3$ | sBu | O-Allyl |
| 337 | 2-Cl, 6-CH$_3$ | sBu | O-Allyl |
| 338 | 2-F, 6-CH$_3$ | sBu | O-Allyl |
| 339 | 2-F | sBu | OCH$_2$-Allyl |
| 340 | 2-Cl | sBu | OCH$_2$-Allyl |
| 341 | 2-Br | sBu | OCH$_2$-Allyl |
| 342 | 2-CF$_3$ | sBu | OCH$_2$-Allyl |
| 343 | 2-CH$_3$ | sBu | OCH$_2$-Allyl |

TABLE 14-continued

| Compound No. | $R^1, R^2, R^3, R^4, R^5$ | $R^6$ | X |
|---|---|---|---|
| 344 | 2-OCH$_3$ | sBu | OCH$_2$-Allyl |
| 345 | 2,6-F$_2$ | sBu | OCH$_2$-Allyl |
| 346 | 2,6-Cl$_2$ | sBu | OCH$_2$-Allyl |
| 347 | 2,6-(CH$_3$)$_2$ | sBu | OCH$_2$-Allyl |
| 348 | 2-F, 6-Cl | sBu | OCH$_2$-Allyl |
| 349 | 2,3,5-Cl$_3$ | sBu | OCH$_2$-Allyl |
| 350 | 2-Cl, 6-CH$_3$ | sBu | OCH$_2$-Allyl |

TABLE 15

| Compound No. | $R^1, R^2, R^3, R^4, R^5$ | $R^6$ | X |
|---|---|---|---|
| 351 | 2-F, 6-CH$_3$ | sBu | OCH$_2$-Allyl |
| 352 | 2-F | sBu | OCH$_2$C≡CH |
| 353 | 2-Cl | sBu | OCH$_2$C≡CH |
| 354 | 2-Br | sBu | OCH$_2$C≡CH |
| 355 | 2-CF$_3$ | sBu | OCH$_2$C≡CH |
| 356 | 2-CH$_3$ | sBu | OCH$_2$C≡CH |
| 357 | 2-OCH$_3$ | sBu | OCH$_2$C≡CH |
| 358 | 2,6-F$_2$ | sBu | OCH$_2$C≡CH |
| 359 | 2,6-Cl$_2$ | sBu | OCH$_2$C≡CH |
| 360 | 2,6-(CH$_3$)$_2$ | sBu | OCH$_2$C≡CH |
| 361 | 2-F, 6-Cl | sBu | OCH$_2$C≡CH |
| 362 | 2,3,5-Cl$_3$ | sBu | OCH$_2$C≡CH |
| 363 | 2-Cl, 6-CH$_3$ | sBu | OCH$_2$C≡CH |
| 364 | 2-F, 6-CH$_3$ | sBu | OCH$_2$C≡CH |
| 365 | 2-F | sBu | OCH$_2$CH$_2$C≡CH |
| 366 | 2-Cl | sBu | OCH$_2$CH$_2$C≡CH |
| 367 | 2-Br | sBu | OCH$_2$CH$_2$C≡CH |
| 368 | 2-CF$_3$ | sBu | OCH$_2$CH$_2$C≡CH |
| 369 | 2-CH$_3$ | sBu | OCH$_2$CH$_2$C≡CH |
| 370 | 2-OCH$_3$ | sBu | OCH$_2$CH$_2$C≡CH |
| 371 | 2,6-F$_2$ | sBu | OCH$_2$CH$_2$C≡CH |
| 372 | 2,6-Cl$_2$ | sBu | OCH$_2$CH$_2$C≡CH |
| 373 | 2,6-(CH$_3$)$_2$ | sBu | OCH$_2$CH$_2$C≡CH |
| 374 | 2-F, 6-Cl | sBu | OCH$_2$CH$_2$C≡CH |
| 375 | 2,3,5-Cl$_3$ | sBu | OCH$_2$CH$_2$C≡CH |

TABLE 16

| Compound No. | $R^1, R^2, R^3, R^4, R^5$ | $R^6$ | X |
|---|---|---|---|
| 376 | 2-Cl, 6-CH$_3$ | sBu | OCH$_2$CH$_2$C≡CH |
| 377 | 2-F, 6-CH$_3$ | sBu | OCH$_2$CH$_2$C≡CH |
| 378 | 2-F | sBu | OCH$_2$=CCH$_3$ |
| 379 | 2-Cl | sBu | OCH$_2$=CCH$_3$ |
| 380 | 2-Br | sBu | OCH$_2$=CCH$_3$ |
| 381 | 2-CF$_3$ | sBu | OCH$_2$=CCH$_3$ |
| 382 | 2-CH$_3$ | sBu | OCH$_2$=CCH$_3$ |
| 383 | 2-OCH$_3$ | sBu | OCH$_2$=CCH$_3$ |
| 384 | 2,6-F$_2$ | sBu | OCH$_2$=CCH$_3$ |
| 385 | 2,6-Cl$_2$ | sBu | OCH$_2$=CCH$_3$ |
| 386 | 2,6-(CH$_3$)$_2$ | sBu | OCH$_2$=CCH$_3$ |
| 387 | 2-F, 6-Cl | sBu | OCH$_2$=CCH$_3$ |
| 388 | 2,3,5-Cl$_3$ | sBu | OCH$_2$=CCH$_3$ |
| 389 | 2-Cl, 6-CH$_3$ | sBu | OCH$_2$=CCH$_3$ |
| 390 | 2-F, 6-CH$_3$ | sBu | OCH$_2$=CCH$_3$ |
| 391 | 2-F | iPr | S-Me |
| 392 | 2-Cl | iPr | S-Me |
| 393 | 2-Br | iPr | S-Me |
| 394 | 2-CF$_3$ | iPr | S-Me |
| 395 | 2-CH$_3$ | iPr | S-Me |
| 396 | 2-OCH$_3$ | iPr | S-Me |
| 397 | 2,6-F$_2$ | iPr | S-Me |
| 398 | 2,6-Cl$_2$ | iPr | S-Me |
| 399 | 2,6-(CH$_3$)$_2$ | iPr | S-Me |
| 400 | 2-F, 6-Cl | iPr | S-Me |

TABLE 17

| Compound No. | R¹, R², R³, R⁴, R⁵ | R⁶ | X |
|---|---|---|---|
| 401 | 2,3,5-Cl$_3$ | iPr | S-Me |
| 402 | 2-Cl, 6-CH$_3$ | iPr | S-Me |
| 403 | 2-F, 6-CH$_3$ | iPr | S-Me |
| 404 | 2-F | iPr | S-Et |
| 405 | 2-Cl | iPr | S-Et |
| 406 | 2-Br | iPr | S-Et |
| 407 | 2-CF$_3$ | iPr | S-Et |
| 408 | 2-CH$_3$ | iPr | S-Et |
| 409 | 2-OCH$_3$ | iPr | S-Et |
| 410 | 2,6-F$_2$ | iPr | S-Et |
| 411 | 2,6-Cl$_2$ | iPr | S-Et |
| 412 | 2,6-(CH$_3$)$_2$ | iPr | S-Et |
| 413 | 2-F, 6-Cl | iPr | S-Et |
| 414 | 2,3,5-Cl$_3$ | iPr | S-Et |
| 415 | 2-Cl, 6-CH$_3$ | iPr | S-Et |
| 416 | 2-F, 6-CH$_3$ | iPr | S-Et |
| 417 | 2-F | iPr | S-nPr |
| 418 | 2-Cl | iPr | S-nPr |
| 419 | 2-Br | iPr | S-nPr |
| 420 | 2-CF$_3$ | iPr | S-nPr |
| 421 | 2-CH$_3$ | iPr | S-nPr |
| 422 | 2-OCH$_3$ | iPr | S-nPr |
| 423 | 2,6-F$_2$ | iPr | S-nPr |
| 424 | 2,6-Cl$_2$ | iPr | S-nPr |
| 425 | 2,6-(CH$_3$)$_2$ | iPr | S-nPr |

TABLE 18

| Compound No. | R¹, R², R³, R⁴, R⁵ | R⁶ | X |
|---|---|---|---|
| 426 | 2-F, 6-Cl | iPr | S-nPr |
| 427 | 2,3,5-Cl$_3$ | iPr | S-nPr |
| 428 | 2-Cl, 6-CH$_3$ | iPr | S-nPr |
| 429 | 2-F, 6-CH$_3$ | iPr | S-nPr |
| 430 | 2-F | iPr | S-nBu |
| 431 | 2-Cl | iPr | S-nBu |
| 432 | 2-Br | iPr | S-nBu |
| 433 | 2-CF$_3$ | iPr | S-nBu |
| 434 | 2-CH$_3$ | iPr | S-nBu |
| 435 | 2-OCH$_3$ | iPr | S-nBu |
| 436 | 2,6-F$_2$ | iPr | S-nBu |
| 437 | 2,6-Cl$_2$ | iPr | S-nBu |
| 438 | 2,6-(CH$_3$)$_2$ | iPr | S-nBu |
| 439 | 2-F, 6-Cl | iPr | S-nBu |
| 440 | 2,3,5-Cl$_3$ | iPr | S-nBu |
| 441 | 2-Cl, 6-CH$_3$ | iPr | S-nBu |
| 442 | 2-F, 6-CH$_3$ | iPr | S-nBu |
| 443 | 2-F | iPr | S-iBu |
| 444 | 2-Cl | iPr | S-iBu |
| 445 | 2-Br | iPr | S-iBu |
| 446 | 2-CF$_3$ | iPr | S-iBu |
| 447 | 2-CH$_3$ | iPr | S-iBu |
| 448 | 2-OCH$_3$ | iPr | S-iBu |
| 449 | 2,6-F$_2$ | iPr | S-iBu |
| 450 | 2,6-Cl$_2$ | iPr | S-iBu |

TABLE 19

| Compound No. | R¹, R², R³, R⁴, R⁵ | R⁶ | X |
|---|---|---|---|
| 451 | 2,6-(CH$_3$)$_2$ | iPr | S-iBu |
| 452 | 2-F, 6-Cl | iPr | S-iBu |
| 453 | 2,3,5-Cl$_3$ | iPr | S-iBu |
| 454 | 2-Cl, 6-CH$_3$ | iPr | S-iBu |
| 455 | 2-F, 6-CH$_3$ | iPr | S-iBu |
| 456 | 2-F | iPr | S-Allyl |
| 457 | 2-Cl | iPr | S-Allyl |
| 458 | 2-Br | iPr | S-Allyl |
| 459 | 2-CF$_3$ | iPr | S-Allyl |
| 460 | 2-CH$_3$ | iPr | S-Allyl |
| 461 | 2-OCH$_3$ | iPr | S-Allyl |
| 462 | 2,6-F$_2$ | iPr | S-Allyl |
| 463 | 2,6-Cl$_2$ | iPr | S-Allyl |
| 464 | 2,6-(CH$_3$)$_2$ | iPr | S-Allyl |
| 465 | 2-F, 6-Cl | iPr | S-Allyl |
| 466 | 2,3,5-Cl$_3$ | iPr | S-Allyl |
| 467 | 2-Cl, 6-CH$_3$ | iPr | S-Allyl |
| 468 | 2-F, 6-CH$_3$ | iPr | S-Allyl |
| 469 | 2-F | iPr | SCH$_2$-Allyl |
| 470 | 2-Cl | iPr | SCH$_2$-Allyl |
| 471 | 2-Br | iPr | SCH$_2$-Allyl |
| 472 | 2-CF$_3$ | iPr | SCH$_2$-Allyl |
| 473 | 2-CH$_3$ | iPr | SCH$_2$-Allyl |
| 474 | 2-OCH$_3$ | iPr | SCH$_2$-Allyl |
| 475 | 2,6-F$_2$ | iPr | SCH$_2$-Allyl |

TABLE 20

| Compound No. | R¹, R², R³, R⁴, R⁵ | R⁶ | X |
|---|---|---|---|
| 476 | 2,6-Cl$_2$ | iPr | SCH$_2$-Allyl |
| 477 | 2,6-(CH$_3$)$_2$ | iPr | SCH$_2$-Allyl |
| 478 | 2-F, 6-Cl | iPr | SCH$_2$-Allyl |
| 479 | 2,3,5-Cl$_3$ | iPr | SCH$_2$-Allyl |
| 480 | 2-Cl, 6-CH$_3$ | iPr | SCH$_2$-Allyl |
| 481 | 2-F, 6-CH$_3$ | iPr | SCH$_2$-Allyl |
| 482 | 2-F | sBu | S-Me |
| 483 | 2-Cl | sBu | S-Me |
| 484 | 2-Br | sBu | S-Me |
| 485 | 2-CF$_3$ | sBu | S-Me |
| 486 | 2-CH$_3$ | sBu | S-Me |
| 487 | 2-OCH$_3$ | sBu | S-Me |
| 488 | 2,6-F$_2$ | sBu | S-Me |
| 489 | 2,6-Cl$_2$ | sBu | S-Me |
| 490 | 2,6-(CH$_3$)$_2$ | sBu | S-Me |
| 491 | 2-F, 6-Cl | sBu | S-Me |
| 492 | 2,3,5-Cl$_3$ | sBu | S-Me |
| 493 | 2-Cl, 6-CH$_3$ | sBu | S-Me |
| 494 | 2-F, 6-CH$_3$ | sBu | S-Me |
| 495 | 2-F | sBu | S-Et |
| 496 | 2-Cl | sBu | S-Et |
| 497 | 2-Br | sBu | S-Et |
| 498 | 2-CF$_3$ | sBu | S-Et |
| 499 | 2-CH$_3$ | sBu | S-Et |
| 500 | 2-OCH$_3$ | sBu | S-Et |

TABLE 21

| Compound No. | R¹, R², R³, R⁴, R⁵ | R⁶ | X |
|---|---|---|---|
| 501 | 2,6-F$_2$ | sBu | S-Et |
| 502 | 2,6-Cl$_2$ | sBu | S-Et |
| 503 | 2,6-(CH$_3$)$_2$ | sBu | S-Et |
| 504 | 2-F, 6-Cl | sBu | S-Et |
| 505 | 2,3,5-Cl$_3$ | sBu | S-Et |
| 506 | 2-Cl, 6-CH$_3$ | sBu | S-Et |
| 507 | 2-F, 6-CH$_3$ | sBu | S-Et |
| 508 | 2-F | sBu | S-nPr |
| 509 | 2-Cl | sBu | S-nPr |
| 510 | 2-Br | sBu | S-nPr |
| 511 | 2-CF$_3$ | sBu | S-nPr |
| 512 | 2-CH$_3$ | sBu | S-nPr |
| 513 | 2-OCH$_3$ | sBu | S-nPr |
| 514 | 2,6-F$_2$ | sBu | S-nPr |
| 515 | 2,6-Cl$_2$ | sBu | S-nPr |
| 516 | 2,6-(CH$_3$)$_2$ | sBu | S-nPr |
| 517 | 2-F, 6-Cl | sBu | S-nPr |
| 518 | 2,3,5-Cl$_3$ | sBu | S-nPr |

TABLE 21-continued

| Compound No. | $R^1, R^2, R^3, R^4, R^5$ | $R^6$ | X |
|---|---|---|---|
| 519 | 2-Cl, 6-CH$_3$ | sBu | S-nPr |
| 520 | 2-F, 6-CH$_3$ | sBu | S-nPr |
| 521 | 2-F | sBu | S-nBu |
| 522 | 2-Cl | sBu | S-nBu |
| 523 | 2-Br | sBu | S-nBu |
| 524 | 2-CF$_3$ | sBu | S-nBu |
| 525 | 2-CH$_3$ | sBu | S-nBu |

TABLE 22

| Compound No. | $R^1, R^2, R^3, R^4, R^5$ | $R^6$ | X |
|---|---|---|---|
| 526 | 2-OCH$_3$ | sBu | S-nBu |
| 527 | 2,6-F$_2$ | sBu | S-nBu |
| 528 | 2,6-Cl$_2$ | sBu | S-nBu |
| 529 | 2,6-(CH$_3$)$_2$ | sBu | S-nBu |
| 530 | 2-F, 6-Cl | sBu | S-nBu |
| 531 | 2,3,5-Cl$_3$ | sBu | S-nBu |
| 532 | 2-Cl, 6-CH$_3$ | sBu | S-nBu |
| 533 | 2-F, 6-CH$_3$ | sBu | S-nBu |
| 534 | 2-F | sBu | S-iBu |
| 535 | 2-Cl | sBu | S-iBu |
| 536 | 2-Br | sBu | S-iBu |
| 537 | 2-CF$_3$ | sBu | S-iBu |
| 538 | 2-CH$_3$ | sBu | S-iBu |
| 539 | 2-OCH$_3$ | sBu | S-iBu |
| 540 | 2,6-F$_2$ | sBu | S-iBu |
| 541 | 2,6-Cl$_2$ | sBu | S-iBu |
| 542 | 2,6-(CH$_3$)$_2$ | sBu | S-iBu |
| 543 | 2-F, 6-Cl | sBu | S-iBu |
| 544 | 2,3,5-Cl$_3$ | sBu | S-iBu |
| 545 | 2-Cl, 6-CH$_3$ | sBu | S-iBu |
| 546 | 2-F, 6-CH$_3$ | sBu | S-iBu |
| 547 | 2-F | sBu | S-Allyl |
| 548 | 2-Cl | sBu | S-Allyl |
| 549 | 2-Br | sBu | S-Allyl |
| 550 | 2-CF$_3$ | sBu | S-Allyl |

TABLE 23

| Compound No. | $R^1, R^2, R^3, R^4, R^5$ | $R^6$ | X |
|---|---|---|---|
| 551 | 2-CH$_3$ | sBu | S-Allyl |
| 552 | 2-OCH$_3$ | sBu | S-Allyl |
| 553 | 2,6-F$_2$ | sBu | S-Allyl |
| 554 | 2,6-Cl$_2$ | sBu | S-Allyl |
| 555 | 2,6-(CH$_3$)$_2$ | sBu | S-Allyl |
| 556 | 2-F, 6-Cl | sBu | S-Allyl |
| 557 | 2,3,5-Cl$_3$ | sBu | S-Allyl |
| 558 | 2-Cl, 6-CH$_3$ | sBu | S-Allyl |
| 559 | 2-F, 6-CH$_3$ | sBu | S-Allyl |
| 560 | 2-F | sBu | SCH$_2$-Allyl |
| 561 | 2-Cl | sBu | SCH$_2$-Allyl |
| 562 | 2-Br | sBu | SCH$_2$-Allyl |
| 563 | 2-CF$_3$ | sBu | SCH$_2$-Allyl |
| 564 | 2-CH$_3$ | sBu | SCH$_2$-Allyl |
| 565 | 2-OCH$_3$ | sBu | SCH$_2$-Allyl |
| 566 | 2,6-F$_2$ | sBu | SCH$_2$-Allyl |
| 567 | 2,6-Cl$_2$ | sBu | SCH$_2$-Allyl |
| 568 | 2,6-(CH$_3$)$_2$ | sBu | SCH$_2$-Allyl |
| 569 | 2-F, 6-Cl | sBu | SCH$_2$-Allyl |
| 570 | 2,3,5-Cl$_3$ | sBu | SCH$_2$-Allyl |
| 571 | 2-Cl, 6-CH$_3$ | sBu | SCH$_2$-Allyl |
| 572 | 2-F, 6-CH$_3$ | sBu | SCH$_2$-Allyl |
| 573 | 2-Me | iPr | cPr |
| 574 | 2,6-Cl$_2$ | iPr | cPr |
| 575 | 2-Me | sBu | cPr |

TABLE 24

| Compound No. | $R^1, R^2, R^3, R^4, R^5$ | $R^6$ | X |
|---|---|---|---|
| 576 | 2,6-Cl$_2$ | sBu | cPr |
| 577 | 2-Me | iPr | OCH$_2$-cPr |
| 578 | 2,6-Cl$_2$ | iPr | OCH$_2$-cPr |
| 579 | 2-Me | sBu | OCH$_2$-cPr |
| 580 | 2,6-Cl$_2$ | sBu | OCH$_2$-cPr |
| 581 | 2-Me | iPr | OCH$_2$CH$_2$Cl |
| 582 | 2,6-Cl$_2$ | iPr | OCH$_2$CH$_2$Cl |
| 583 | 2-Me | sBu | OCH$_2$CH$_2$Cl |
| 584 | 2,6-Cl$_2$ | sBu | OCH$_2$CH$_2$Cl |
| 585 | 2-Me | iPr | OCH$_2$Ph |
| 586 | 2,6-Cl$_2$ | iPr | OCH$_2$Ph |
| 587 | 2-Me | sBu | OCH$_2$Ph |
| 588 | 2,6-Cl$_2$ | sBu | OCH$_2$Ph |
| 589 | 2-Me | iPr | OCH$_2$C(Me)=CH$_2$ |
| 590 | 2,6-Cl$_2$ | iPr | OCH$_2$C(Me)=CH$_2$ |
| 591 | 2-Me | sBu | OCH$_2$C(Me)=CH$_2$ |
| 592 | 2,6-Cl$_2$ | sBu | OCH$_2$C(Me)=CH$_2$ |
| 593 | 2-Me | Et | O-Allyl |
| 594 | 2-Me | Et | OCH$_2$C≡CH |
| 595 | 2-Me | Et | SEt |
| 596 | 2-Me | Et | S-Allyl |
| 597 | 2,6-Cl$_2$ | Et | O-Allyl |
| 598 | 2,6-Cl$_2$ | Et | OCH$_2$C≡CH |
| 599 | 2,6-Cl$_2$ | Et | SEt |
| 600 | 2,6-Cl$_2$ | Et | S-Allyl |

TABLE 25

| Compound No. | $R^1, R^2, R^3, R^4, R^5$ | $R^6$ | X |
|---|---|---|---|
| (−)-499 | 2-Me | sBu | SEt |
| (+)-499 | 2-Me | sBu | SEt |
| (−)-502 | 2,6-Cl$_2$ | sBu | SEt |
| (+)-502 | 2,6-Cl$_2$ | sBu | SEt |

The compounds represented by the formula:

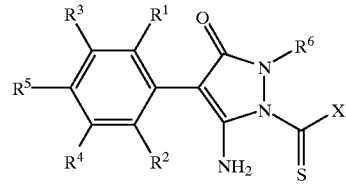

TABLE 26

| Compound No. | $R^1, R^2, R^3, R^4, R^5$ | $R^6$ | X |
|---|---|---|---|
| 601 | 2-F | iPr | O-Me |
| 602 | 2-Cl | iPr | O-Me |
| 603 | 2-Br | iPr | O-Me |
| 604 | 2-CF$_3$ | iPr | O-Me |
| 605 | 2-CH$_3$ | iPr | O-Me |
| 606 | 2-OCH$_3$ | iPr | O-Me |
| 607 | 2,6-F$_2$ | iPr | O-Me |
| 608 | 2,6-Cl$_2$ | iPr | O-Me |
| 609 | 2,6-(CH$_3$)$_2$ | iPr | O-Me |
| 610 | 2-F, 6-Cl | iPr | O-Me |
| 611 | 2,3,5-Cl$_3$ | iPr | O-Me |
| 612 | 2-Cl, 6-CH$_3$ | iPr | O-Me |
| 613 | 2-F, 6-CH$_3$ | iPr | O-Me |
| 614 | 2-F | iPr | O-Et |
| 615 | 2-Cl | iPr | O-Et |
| 616 | 2-Br | iPr | O-Et |

TABLE 26-continued

| Compound No. | $R^1, R^2, R^3, R^4, R^5$ | $R^6$ | X |
|---|---|---|---|
| 617 | 2-CF$_3$ | iPr | O-Et |
| 618 | 2-CH$_3$ | iPr | O-Et |
| 619 | 2-OCH$_3$ | iPr | O-Et |
| 620 | 2,6-F$_2$ | iPr | O-Et |
| 621 | 2,6-Cl$_2$ | iPr | O-Et |
| 622 | 2,6-(CH$_3$)$_2$ | iPr | O-Et |
| 623 | 2-F, 6-Cl | iPr | O-Et |
| 624 | 2,3,5-Cl$_3$ | iPr | O-Et |
| 625 | 2-Cl, 6-CH$_3$ | iPr | O-Et |

TABLE 27

| Compound No. | $R^1, R^2, R^3, R^4, R^5$ | $R^6$ | X |
|---|---|---|---|
| 626 | 2-F, 6-CH$_3$ | iPr | O-Et |
| 627 | 2-F | iPr | O-nPr |
| 628 | 2-Cl | iPr | O-nPr |
| 629 | 2-Br | iPr | O-nPr |
| 630 | 2-CF$_3$ | iPr | O-nPr |
| 631 | 2-CH$_3$ | iPr | O-nPr |
| 632 | 2-OCH$_3$ | iPr | O-nPr |
| 633 | 2,6-F$_2$ | iPr | O-nPr |
| 634 | 2,6-Cl$_2$ | iPr | O-nPr |
| 635 | 2,6-(CH$_3$)$_2$ | iPr | O-nPr |
| 636 | 2-F, 6-Cl | iPr | O-nPr |
| 637 | 2,3,5-Cl$_3$ | iPr | O-nPr |
| 638 | 2-Cl, 6-CH$_3$ | iPr | O-nPr |
| 639 | 2-F, 6-CH$_3$ | iPr | O-nPr |
| 640 | 2-F | iPr | O-nBu |
| 641 | 2-Cl | iPr | O-nBu |
| 642 | 2-Br | iPr | O-nBu |
| 643 | 2-CF$_3$ | iPr | O-nBu |
| 644 | 2-CH$_3$ | iPr | O-nBu |
| 645 | 2-OCH$_3$ | iPr | O-nBu |
| 646 | 2,6-F$_2$ | iPr | O-nBu |
| 647 | 2,6-Cl$_2$ | iPr | O-nBu |
| 648 | 2,6-(CH$_3$)$_2$ | iPr | O-nBu |
| 649 | 2-F, 6-Cl | iPr | O-nBu |
| 650 | 2,3,5-Cl$_3$ | iPr | O-nBu |

TABLE 28

| Compound No. | $R^1, R^2, R^3, R^4, R^5$ | $R^6$ | X |
|---|---|---|---|
| 651 | 2-Cl, 6-CH$_3$ | iPr | O-nBu |
| 652 | 2-F, 6-CH$_3$ | iPr | O-nBu |
| 653 | 2-F | iPr | O-iBu |
| 654 | 2-Cl | iPr | O-iBu |
| 655 | 2-Br | iPr | O-iBu |
| 656 | 2-CF$_3$ | iPr | O-iBu |
| 657 | 2-CH$_3$ | iPr | O-iBu |
| 658 | 2-OCH$_3$ | iPr | O-iBu |
| 659 | 2,6-F$_2$ | iPr | O-iBu |
| 660 | 2,6-Cl$_2$ | iPr | O-iBu |
| 661 | 2,6-(CH$_3$)$_2$ | iPr | O-iBu |
| 662 | 2-F, 6-Cl | iPr | O-iBu |
| 663 | 2,3,5-Cl$_3$ | iPr | O-iBu |
| 664 | 2-Cl, 6-CH$_3$ | iPr | O-iBu |
| 665 | 2-F, 6-CH$_3$ | iPr | O-iBu |
| 666 | 2-F | iPr | O-Allyl |
| 667 | 2-Cl | iPr | O-Allyl |
| 668 | 2-Br | iPr | O-Allyl |
| 669 | 2-CF$_3$ | iPr | O-Allyl |
| 670 | 2-CH$_3$ | iPr | O-Allyl |
| 671 | 2-OCH$_3$ | iPr | O-Allyl |
| 672 | 2,6-F$_2$ | iPr | O-Allyl |
| 673 | 2,6-Cl$_2$ | iPr | O-Allyl |

TABLE 28-continued

| Compound No. | $R^1, R^2, R^3, R^4, R^5$ | $R^6$ | X |
|---|---|---|---|
| 674 | 2,6-(CH$_3$)$_2$ | iPr | O-Allyl |
| 675 | 2-F, 6-Cl | iPr | O-Allyl |

TABLE 29

| Compound No. | $R^1, R^2, R^3, R^4, R^5$ | $R^6$ | X |
|---|---|---|---|
| 676 | 2,3,5-Cl$_3$ | iPr | O-Allyl |
| 677 | 2-Cl, 6-CH$_3$ | iPr | O-Allyl |
| 678 | 2-F, 6-CH$_3$ | iPr | O-Allyl |
| 679 | 2-F | iPr | OCH$_2$-Allyl |
| 680 | 2-Cl | iPr | OCH$_2$-Allyl |
| 681 | 2-Br | iPr | OCH$_2$-Allyl |
| 682 | 2-CF$_3$ | iPr | OCH$_2$-Allyl |
| 683 | 2-CH$_3$ | iPr | OCH$_2$-Allyl |
| 684 | 2-OCH$_3$ | iPr | OCH$_2$-Allyl |
| 685 | 2,6-F$_2$ | iPr | OCH$_2$-Allyl |
| 686 | 2,6-Cl$_2$ | iPr | OCH$_2$-Allyl |
| 687 | 2,6-(CH$_3$)$_2$ | iPr | OCH$_2$-Allyl |
| 688 | 2-F, 6-Cl | iPr | OCH$_2$-Allyl |
| 689 | 2,3,5-Cl$_3$ | iPr | OCH$_2$-Allyl |
| 690 | 2-Cl, 6-CH$_3$ | iPr | OCH$_2$-Allyl |
| 691 | 2-F, 6-CH$_3$ | iPr | OCH$_2$-Allyl |
| 692 | 2-F | iPr | OCH$_2$C≡CH |
| 693 | 2-Cl | iPr | OCH$_2$C≡CH |
| 694 | 2-Br | iPr | OCH$_2$C≡CH |
| 695 | 2-CF$_3$ | iPr | OCH$_2$C≡CH |
| 696 | 2-CH$_3$ | iPr | OCH$_2$C≡CH |
| 697 | 2-OCH$_3$ | iPr | OCH$_2$C≡CH |
| 698 | 2,6-F$_2$ | iPr | OCH$_2$C≡CH |
| 699 | 2,6-Cl$_2$ | iPr | OCH$_2$C≡CH |
| 700 | 2,6-(CH$_3$)$_2$ | iPr | OCH$_2$C≡CH |

TABLE 30

| Compound No. | $R^1, R^2, R^3, R^4, R^5$ | $R^6$ | X |
|---|---|---|---|
| 701 | 2-F, 6-Cl | iPr | OCH$_2$C≡CH |
| 702 | 2,3,5-Cl$_3$ | iPr | OCH$_2$C≡CH |
| 703 | 2-Cl, 6-CH$_3$ | iPr | OCH$_2$C≡CH |
| 704 | 2-F, 6-CH$_3$ | iPr | OCH$_2$C≡CH |
| 705 | 2-F | iPr | OCH$_2$CH$_2$C≡CH |
| 706 | 2-Cl | iPr | OCH$_2$CH$_2$C≡CH |
| 707 | 2-Br | iPr | OCH$_2$CH$_2$C≡CH |
| 708 | 2-CF$_3$ | iPr | OCH$_2$CH$_2$C≡CH |
| 709 | 2-CH$_3$ | iPr | OCH$_2$CH$_2$C≡CH |
| 710 | 2-OCH$_3$ | iPr | OCH$_2$CH$_2$C≡CH |
| 711 | 2,6-F$_2$ | iPr | OCH$_2$CH$_2$C≡CH |
| 712 | 2,6-Cl$_2$ | iPr | OCH$_2$CH$_2$C≡CH |
| 713 | 2,6-(CH$_3$)$_2$ | iPr | OCH$_2$CH$_2$C≡CH |
| 714 | 2-F, 6-Cl | iPr | OCH$_2$CH$_2$C≡CH |
| 715 | 2,3,5-Cl$_3$ | iPr | OCH$_2$CH$_2$C≡CH |
| 716 | 2-Cl, 6-CH$_3$ | iPr | OCH$_2$CH$_2$C≡CH |
| 717 | 2-F, 6-CH$_3$ | iPr | OCH$_2$CH$_2$C≡CH |
| 718 | 2-F | iPr | OCH$_2$C≡CCH$_3$ |
| 719 | 2-Cl | iPr | OCH$_2$C≡CCH$_3$ |
| 720 | 2-Br | iPr | OCH$_2$C≡CCH$_3$ |
| 721 | 2-CF$_3$ | iPr | OCH$_2$C≡CCH$_3$ |
| 722 | 2-CH$_3$ | iPr | OCH$_2$C≡CCH$_3$ |
| 723 | 2-OCH$_3$ | iPr | OCH$_2$C≡CCH$_3$ |
| 724 | 2,6-F$_2$ | iPr | OCH$_2$C≡CCH$_3$ |
| 725 | 2,6-Cl$_2$ | iPr | OCH$_2$C≡CCH$_3$ |

TABLE 31

| Compound No. | R¹, R², R³, R⁴, R⁵ | R⁶ | X |
|---|---|---|---|
| 726 | 2,6-(CH₃)₂ | iPr | OCH₂C≡CCH₃ |
| 727 | 2-F, 6-Cl | iPr | OCH₂C≡CCH₃ |
| 728 | 2,3,5-Cl₃ | iPr | OCH₂C≡CCH₃ |
| 729 | 2-Cl, 6-CH₃ | iPr | OCH₂C≡CCH₃ |
| 730 | 2-F, 6-CH₃ | iPr | OCH₂C≡CCH₃ |
| 731 | 2-F | sBu | O-Me |
| 732 | 2-Cl | sBu | O-Me |
| 733 | 2-Br | sBu | O-Me |
| 734 | 2-CF₃ | sBu | O-Me |
| 735 | 2-CH₃ | sBu | O-Me |
| 736 | 2-OCH₃ | sBu | O-Me |
| 737 | 2,6-F₂ | sBu | O-Me |
| 738 | 2,6-Cl₂ | sBu | O-Me |
| 739 | 2,6-(CH₃)₂ | sBu | O-Me |
| 740 | 2-F, 6-Cl | sBu | O-Me |
| 741 | 2,3,5-Cl₃ | sBu | O-Me |
| 742 | 2-Cl, 6-CH₃ | sBu | O-Me |
| 743 | 2-F, 6-CH₃ | sBu | O-Me |
| 744 | 2-F | sBu | O-Et |
| 745 | 2-Cl | sBu | O-Et |
| 746 | 2-Br | sBu | O-Et |
| 747 | 2-CF₃ | sBu | O-Et |
| 748 | 2-CH₃ | sBu | O-Et |
| 749 | 2-OCH₃ | sBu | O-Et |
| 750 | 2,6-F₂ | sBu | O-Et |

TABLE 32

| Compound No. | R¹, R², R³, R⁴, R⁵ | R⁶ | X |
|---|---|---|---|
| 751 | 2,6-Cl₂ | sBu | O-Et |
| 752 | 2,6-(CH₃)₂ | sBu | O-Et |
| 753 | 2-F, 6-Cl | sBu | O-Et |
| 754 | 2,3,5-Cl₃ | sBu | O-Et |
| 755 | 2-Cl, 6-CH₃ | sBu | O-Et |
| 756 | 2-F, 6-CH₃ | sBu | O-Et |
| 757 | 2-F | sBu | O-nPr |
| 758 | 2-Cl | sBu | O-nPr |
| 759 | 2-Br | sBu | O-nPr |
| 760 | 2-CF₃ | sBu | O-nPr |
| 761 | 2-CH₃ | sBu | O-nPr |
| 762 | 2-OCH₃ | sBu | O-nPr |
| 763 | 2,6-F₂ | sBu | O-nPr |
| 764 | 2,6-Cl₂ | sBu | O-nPr |
| 765 | 2,6-(CH₃)₂ | sBu | O-nPr |
| 766 | 2-F, 6-Cl | sBu | O-nPr |
| 767 | 2,3,5-Cl₃ | sBu | O-nPr |
| 768 | 2-Cl, 6-CH₃ | sBu | O-nPr |
| 769 | 2-F, 6-CH₃ | sBu | O-nPr |
| 770 | 2-F | sBu | O-nBu |
| 771 | 2-Cl | sBu | O-nBu |
| 772 | 2-Br | sBu | O-nBu |
| 773 | 2-CF₃ | sBu | O-nBu |
| 774 | 2-CH₃ | sBu | O-nBu |
| 775 | 2-OCH₃ | sBu | O-nBu |

TABLE 33

| Compound No. | R¹, R², R³, R⁴, R⁵ | R⁶ | X |
|---|---|---|---|
| 776 | 2,6-F₂ | sBu | O-nBu |
| 777 | 2,6-Cl₂ | sBu | O-nBu |
| 778 | 2,6-(CH₃)₂ | sBu | O-nBu |
| 779 | 2-F, 6-Cl | sBu | O-nBu |
| 780 | 2,3,5-Cl₃ | sBu | O-nBu |
| 781 | 2-Cl, 6-CH₃ | sBu | O-nBu |
| 782 | 2-F, 6-CH₃ | sBu | O-nBu |
| 783 | 2-F | sBu | O-iBu |
| 784 | 2-Cl | sBu | O-iBu |
| 785 | 2-Br | sBu | O-iBu |
| 786 | 2-CF₃ | sBu | O-iBu |
| 787 | 2-CH₃ | sBu | O-iBu |
| 788 | 2-OCH₃ | sBu | O-iBu |
| 789 | 2,6-F₂ | sBu | O-iBu |
| 790 | 2,6-Cl₂ | sBu | O-iBu |
| 791 | 2,6-(CH₃)₂ | sBu | O-iBu |
| 792 | 2-F, 6-Cl | sBu | O-iBu |
| 793 | 2,3,5-Cl₃ | sBu | O-iBu |
| 794 | 2-Cl, 6-CH₃ | sBu | O-iBu |
| 795 | 2-F, 6-CH₃ | sBu | O-iBu |
| 796 | 2-F | sBu | O-Allyl |
| 797 | 2-Cl | sBu | O-Allyl |
| 798 | 2-Br | sBu | O-Allyl |
| 799 | 2-CF₃ | sBu | O-Allyl |
| 800 | 2-CH₃ | sBu | O-Allyl |

TABLE 34

| Compound No. | R¹, R², R³, R⁴, R⁵ | R⁶ | X |
|---|---|---|---|
| 801 | 2-OCH₃ | sBu | O-Allyl |
| 802 | 2,6-F₂ | sBu | O-Allyl |
| 803 | 2,6-Cl₂ | sBu | O-Allyl |
| 804 | 2,6-(CH₃)₂ | sBu | O-Allyl |
| 805 | 2-F, 6-Cl | sBu | O-Allyl |
| 806 | 2,3,5-Cl₃ | sBu | O-Allyl |
| 807 | 2-Cl, 6-CH₃ | sBu | O-Allyl |
| 808 | 2-F, 6-CH₃ | sBu | O-Allyl |
| 809 | 2-F | sBu | OCH₂-Allyl |
| 810 | 2-Cl | sBu | OCH₂-Allyl |
| 811 | 2-Br | sBu | OCH₂-Allyl |
| 812 | 2-CF₃ | sBu | OCH₂-Allyl |
| 813 | 2-CH₃ | sBu | OCH₂-Allyl |
| 814 | 2-OCH₃ | sBu | OCH₂-Allyl |
| 815 | 2,6-F₂ | sBu | OCH₂-Allyl |
| 816 | 2,6-Cl₂ | sBu | OCH₂-Allyl |
| 817 | 2,6-(CH₃)₂ | sBu | OCH₂-Allyl |
| 818 | 2-F, 6-Cl | sBu | OCH₂-Allyl |
| 819 | 2,3,5-Cl₃ | sBu | OCH₂-Allyl |
| 820 | 2-Cl, 6-CH₃ | sBu | OCH₂-Allyl |
| 821 | 2-F, 6-CH₃ | sBu | OCH₂-Allyl |
| 822 | 2-F | sBu | OCH₂C≡CH |
| 823 | 2-Cl | sBu | OCH₂C≡CH |
| 824 | 2-Br | sBu | OCH₂C≡CH |
| 825 | 2-CF₃ | sBu | OCH₂C≡CH |

TABLE 35

| Compound No. | R¹, R², R³, R⁴, R⁵ | R⁶ | X |
|---|---|---|---|
| 826 | 2-CH₃ | sBu | OCH₂C≡CH |
| 827 | 2-OCH₃ | sBu | OCH₂C≡CH |
| 828 | 2,6-F₂ | sBu | OCH₂C≡CH |
| 829 | 2,6-Cl₂ | sBu | OCH₂C≡CH |
| 830 | 2,6-(CH₃)₂ | sBu | OCH₂C≡CH |
| 831 | 2-F, 6-Cl | sBu | OCH₂C≡CH |
| 832 | 2,3,5-Cl₃ | sBu | OCH₂C≡CH |
| 833 | 2-Cl, 6-CH₃ | sBu | OCH₂C≡CH |
| 834 | 2-F, 6-CH₃ | sBu | OCH₂C≡CH |
| 835 | 2-F | sBu | OCH₂CH₂C≡CH |
| 836 | 2-Cl | sBu | OCH₂CH₂C≡CH |
| 837 | 2-Br | sBu | OCH₂CH₂C≡CH |
| 838 | 2-CF₃ | sBu | OCH₂CH₂C≡CH |
| 839 | 2-CH₃ | sBu | OCH₂CH₂C≡CH |
| 840 | 2-OCH₃ | sBu | OCH₂CH₂C≡CH |
| 841 | 2,6-F₂ | sBu | OCH₂CH₂C≡CH |
| 842 | 2,6-Cl₂ | sBu | OCH₂CH₂C≡CH |
| 843 | 2,6-(CH₃)₂ | sBu | OCH₂CH₂C≡CH |

TABLE 35-continued

| Compound No. | $R^1, R^2, R^3, R^4, R^5$ | $R^6$ | X |
|---|---|---|---|
| 844 | 2-F, 6-Cl | sBu | OCH$_2$CH$_2$C≡CH |
| 845 | 2,3,5-Cl$_3$ | sBu | OCH$_2$CH$_2$C≡CH |
| 846 | 2-Cl, 6-CH$_3$ | sBu | OCH$_2$CH$_2$C≡CCH |
| 847 | 2-F, 6-CH$_3$ | sBu | OCH$_2$CH$_2$C≡CCH |
| 848 | 2-F | sBu | OCH$_2$C≡CCH$_3$ |
| 849 | 2-Cl | sBu | OCH$_2$C≡CCH$_3$ |
| 850 | 2-Br | sBu | OCH$_2$C≡CCH$_3$ |

TABLE 36

| Compound No. | $R^1, R^2, R^3, R^4, R^5$ | $R^6$ | X |
|---|---|---|---|
| 851 | 2-CF$_3$ | sBu | OCH$_2$C≡CCH$_3$ |
| 852 | 2-CH$_3$ | sBu | OCH$_2$C≡CCH$_3$ |
| 853 | 2-OCH$_3$ | sBu | OCH$_2$C≡CCH$_3$ |
| 854 | 2,6-F$_2$ | sBu | OCH$_2$C≡CCH$_3$ |
| 855 | 2,6-Cl$_2$ | sBu | OCH$_2$C≡CCH$_3$ |
| 856 | 2,6-(CH$_3$)$_2$ | sBu | OCH$_2$C≡CCH$_3$ |
| 857 | 2-F, 6-Cl | sBu | OCH$_2$C≡CCH$_3$ |
| 858 | 2,3,5-Cl$_3$ | sBu | OCH$_2$C≡CCH$_3$ |
| 859 | 2-Cl, 6-CH$_3$ | sBu | OCH$_2$C≡CCH$_3$ |
| 860 | 2-F, 6-CH$_3$ | sBu | OCH$_2$C≡CCH$_3$ |
| 861 | 2,6-Cl$_2$ | iPr | OCH$_2$-cPr |
| 862 | 2,6-Cl$_2$ | sBu | OCH$_2$-cPr |
| 863 | 2-CH$_3$ | iPr | OCH$_2$-cPr |
| 864 | 2-CH$_3$ | sBu | OCH$_2$-cPr |

TABLE 37

| Compound No. | $R^1, R^2, R^3, R^4, R^5$ | $R^6$ | X |
|---|---|---|---|
| 865 | 2,6-Cl$_2$ | iPr | OCH$_2$CH$_2$Cl |
| 866 | 2,6-Cl$_2$ | sBu | OCH$_2$CH$_2$Cl |
| 867 | 2-CH$_3$ | iPr | OCH$_2$CH$_2$Cl |
| 868 | 2-CH$_3$ | sBu | OCH$_2$CH$_2$Cl |
| 869 | 2,6-Cl$_2$ | iPr | OCH$_2$Ph |
| 870 | 2,6-Cl$_2$ | sBu | OCH$_2$Ph |
| 871 | 2-CH$_3$ | iPr | OCH$_2$Ph |
| 872 | 2-CH$_3$ | sBu | OCH$_2$Ph |
| 873 | 2,6-Cl$_2$ | iPr | OCH$_2$C(Me)=CH$_2$ |
| 874 | 2,6-Cl$_2$ | sBu | OCH$_2$C(Me)=CH$_2$ |
| 875 | 2-CH$_3$ | iPr | OCH$_2$C(Me)=CH$_2$ |
| 876 | 2-CH$_3$ | sBu | OCH$_2$C(Me)=CH$_2$ |

The compounds represented by the formula:

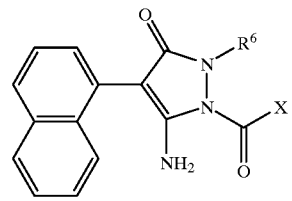

TABLE 38

| Compound No. | $R^6$ | X |
|---|---|---|
| 877 | iPr | O-Me |
| 878 | iPr | O-Et |
| 879 | iPr | O-nPr |

TABLE 38-continued

| Compound No. | $R^6$ | X |
|---|---|---|
| 880 | iPr | O-nBu |
| 881 | iPr | O-iBu |
| 882 | iPr | O-Allyl |
| 883 | iPr | OCH$_2$-Allyl |
| 884 | iPr | OCH$_2$C≡CH |
| 885 | iPr | OCH$_2$CH$_2$C≡CH |
| 886 | iPr | OCH$_2$C≡CCH$_3$ |
| 887 | sBu | O-Me |
| 888 | sBu | O-Et |
| 889 | sBu | O-nPr |
| 890 | sBu | O-nBu |
| 891 | sBu | O-iBu |
| 892 | sBu | O-Allyl |
| 893 | sBu | OCH$_2$-Allyl |
| 894 | sBu | OCH$_2$C≡CH |
| 895 | sBu | OCH$_2$CH$_2$C≡CH |
| 896 | sBu | OCH$_2$C≡CCH$_3$ |
| 897 | iPr | Me |
| 898 | iPr | Et |
| 899 | iPr | nPr |
| 900 | sBu | Me |
| 901 | sBu | Et |

TABLE 39

| Compound No. | $R^6$ | X |
|---|---|---|
| 902 | sBu | nPr |
| 903 | iPr | S-Me |
| 904 | iPr | S-Et |
| 905 | iPr | S-nPr |
| 906 | iPr | S-nBu |
| 907 | iPr | S-Allyl |
| 908 | iPr | SCH$_2$-Allyl |
| 909 | sBu | S-Me |
| 910 | sBu | S-Et |
| 911 | sBu | S-nPr |
| 912 | sBu | S-nBu |
| 913 | sBu | S-Allyl |
| 914 | sBu | SCH$_2$-Allyl |

The compounds represented by the formula:

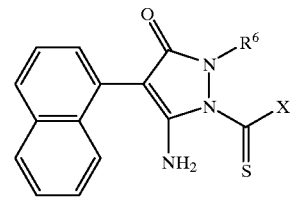

TABLE 40

| Compound No. | $R^6$ | X |
|---|---|---|
| 915 | iPr | O-Me |
| 916 | iPr | O-Et |
| 917 | iPr | O-nPr |
| 918 | iPr | O-nBu |
| 919 | iPr | O-iBu |
| 920 | iPr | O-Allyl |
| 921 | iPr | OCH$_2$-Allyl |
| 922 | iPr | OCH$_2$C≡CH |
| 923 | iPr | OCH$_2$CH$_2$C≡CH |
| 924 | iPr | OCH$_2$C≡CCH$_3$ |

TABLE 40-continued

| Compound No. | $R^6$ | X |
| --- | --- | --- |
| 925 | sBu | O-Me |
| 926 | sBu | O-Et |
| 927 | sBu | O-nPr |
| 928 | sBu | O-nBu |
| 929 | sBu | O-iBu |
| 930 | sBu | O-Allyl |
| 931 | sBu | OCH$_2$-Allyl |
| 932 | sBu | OCH$_2$C≡CH |
| 933 | sBu | OCH$_2$CH$_2$C≡CH |
| 934 | sBu | OCH$_2$C≡CCH$_3$ |

TABLE 41

| Compound No. | $R^6$ | X |
| --- | --- | --- |
| 935 | iPr | Me |
| 936 | iPr | Et |
| 937 | iPr | nPr |
| 938 | sBu | Me |
| 939 | sBu | Et |
| 940 | sBu | nPr |

Examples of the intermediates A are shown with compound No. in Tables 42 to 44.

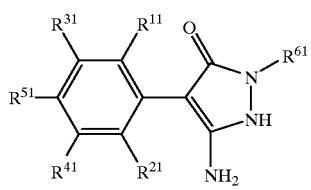

TABLE 42

| Compound No. | $R^{11}R^{21}, R^{31}, R^{41}, R^{51}$ | $R^{61}$ |
| --- | --- | --- |
| 1000 | 2-F | iPr |
| 1001 | 2-Cl | iPr |
| 1002 | 2-Br | iPr |
| 1003 | 2-CF$_3$ | iPr |
| 1004 | 2-CH$_3$ | iPr |
| 1005 | 2-OCH$_3$ | iPr |
| 1006 | 2,6-F$_2$ | iPr |
| 1007 | 2,6-Cl$_2$ | iPr |
| 1008 | 2,6-(CH$_3$)$_2$ | iPr |
| 1009 | 2-F, 6-Cl | iPr |
| 1010 | 2,3,5-Cl$_3$ | iPr |
| 1011 | 2-Cl, 6-CH$_3$ | iPr |
| 1012 | 2-F, 6-CH$_3$ | iPr |
| 1013 | 2-F | sBu |
| 1014 | 2-Cl | sBu |
| 1015 | 2-Br | sBu |
| 1016 | 2-CF$_3$ | sBu |
| 1017 | 2-CH$_3$ | sBu |
| 1018 | 2-OCH$_3$ | sBu |
| 1019 | 2,6-F$_2$ | sBu |
| 1020 | 2,6-Cl$_2$ | sBu |
| 1021 | 2,6(CH$_3$)$_2$ | sBu |
| 1022 | 2-F, 6-Cl | sBu |

TABLE 43

| Compound No. | $R^{11}R^{21}, R^{31}, R^{41}, R^{51}$ | $R^{61}$ |
| --- | --- | --- |
| 1023 | 2,3,5-Cl$_3$ | sBu |
| 1024 | 2-Cl, 6-CH$_3$ | sBu |
| 1025 | 2-F, 6-CH$_3$ | sBu |

The compounds represented by the formula:

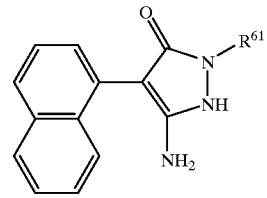

TABLE 44

| Compound No. | $R^{61}$ |
| --- | --- |
| 1026 | iPr |
| 1027 | sBu |

Examples of the intermediates B are shown with No. in Tables 45 to 64.

The compounds represented by the formula:

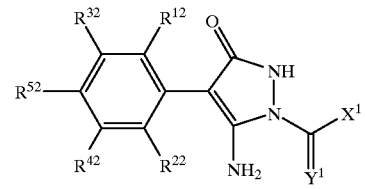

TABLE 45

| Compound No. | $R^{12}, R^{22}, R^{32}, R^{42}, R^{52}$ | $Y^1$ | $X^1$ |
| --- | --- | --- | --- |
| 2000 | 2-F | O | O-Me |
| 2001 | 2-Cl | O | O-Me |
| 2002 | 2-Br | O | O-Me |
| 2003 | 2-CF$_3$ | O | O-Me |
| 2004 | 2-CH$_3$ | O | O-Me |
| 2005 | 2-OCH$_3$ | O | O-Ne |
| 2006 | 2,6-F$_2$ | O | O-Me |
| 2007 | 2,6-Cl$_2$ | O | O-Me |
| 2008 | 2,6-(CH$_3$)$_2$ | O | O-Me |
| 2009 | 2-F, 6-Cl | O | O-Me |
| 2010 | 2,3,5-Cl$_3$ | O | O-Me |
| 2011 | 2-Cl, 6-CH$_3$ | O | O-Me |
| 2012 | 2-F, 6-CH$_3$ | O | O-Me |
| 2013 | 2-F | O | O-Et |
| 2014 | 2-Cl | O | O-Et |
| 2015 | 2-Br | O | O-Et |
| 2016 | 2-CF$_3$ | O | O-Et |
| 2017 | 2-CH$_3$ | O | O-Et |
| 2018 | 2-OCH$_3$ | O | O-Et |
| 2019 | 2,6-F$_2$ | O | O-Et |
| 2020 | 2,6-Cl$_2$ | O | O-Et |
| 2021 | 2,6-(CH$_3$)$_2$ | O | O-Et |
| 2022 | 2-F, 6-Cl | O | O-Et |

TABLE 45-continued

| Compound No. | $R^{12}, R^{22}, R^{32}, R^{42}, R^{52}$ | $Y^1$ | $X^1$ |
|---|---|---|---|
| 2023 | 2,3,5-Cl$_3$ | O | O-Et |
| 2024 | 2-Cl, 6-CH$_3$ | O | O-Et |

TABLE 46

| Compound No. | $R^{12}, R^{22}, R^{32}, R^{42}, R^{52}$ | $Y^1$ | $X^1$ |
|---|---|---|---|
| 2025 | 2-F, 6-CH$_3$ | O | O-Et |
| 2026 | 2-F | O | nPr |
| 2027 | 2-Cl | O | nPr |
| 2028 | 2-Br | O | nPr |
| 2029 | 2-CF$_3$ | O | nPr |
| 2030 | 2-CH$_3$ | O | nPr |
| 2031 | 2-OCH$_3$ | O | nPr |
| 2032 | 2,6-F$_2$ | O | nPr |
| 2033 | 2,6-Cl$_2$ | O | nPr |
| 2034 | 2,6-(CH$_3$)$_2$ | O | nPr |
| 2035 | 2-F, 6-Cl | O | nPr |
| 2036 | 2,3,5-Cl$_3$ | O | nPr |
| 2037 | 2-Cl, 6-CH$_3$ | O | nPr |
| 2038 | 2-F, 6-CH$_3$ | O | nPr |
| 2039 | 2-F | O | O-nBu |
| 2040 | 2-Cl | O | O-nBu |
| 2041 | 2-Br | O | O-nBu |
| 2042 | 2-CF$_3$ | O | O-nBu |
| 2043 | 2-CH$_3$ | O | O-nBu |
| 2044 | 2-OCH$_3$ | O | O-nBu |
| 2045 | 2,6-F$_2$ | O | O-nBu |
| 2046 | 2,6-Cl$_2$ | O | O-nBu |
| 2047 | 2,6-(CH$_3$)$_2$ | O | O-nBu |
| 2048 | 2-F, 6-Cl | O | O-nBu |
| 2049 | 2,3,5-Cl$_3$ | O | O-nBu |

TABLE 47

| Compound No. | $R^{12}, R^{22}, R^{32}, R^{42}, R^{52}$ | $Y^1$ | $X^1$ |
|---|---|---|---|
| 2050 | 2-Cl, 6-CH$_3$ | O | O-nBu |
| 2051 | 2-F, 6-CH$_3$ | O | O-nBu |
| 2052 | 2-F | O | O-iBu |
| 2053 | 2-Cl | O | O-iBu |
| 2054 | 2-Br | O | O-iBu |
| 2055 | 2-CF$_3$ | O | O-iBu |
| 2056 | 2-CH$_3$ | O | O-iBu |
| 2057 | 2-OCH$_3$ | O | O-iBu |
| 2058 | 2,6-F$_2$ | O | O-iBu |
| 2059 | 2,6-Cl$_2$ | O | O-iBu |
| 2060 | 2,6-(CH$_3$)$_2$ | O | O-iBu |
| 2061 | 2-F, 6-Cl | O | O-iBu |
| 2062 | 2,3,5-Cl$_3$ | O | O-iBu |
| 2063 | 2-Cl, 6-CH$_3$ | O | O-iBu |
| 2064 | 2-F, 6-CH$_3$ | O | O-iBu |
| 2065 | 2-F | O | O-Allyl |
| 2066 | 2-Cl | O | O-Allyl |
| 2067 | 2-Br | O | O-Allyl |
| 2068 | 2-CF$_3$ | O | O-Allyl |
| 2069 | 2-CH$_3$ | O | O-Allyl |
| 2070 | 2-OCH$_3$ | O | O-Allyl |
| 2071 | 2,6-F$_2$ | O | O-Allyl |
| 2072 | 2,6-Cl$_2$ | O | O-Allyl |
| 2073 | 2,6-(CH$_3$)$_2$ | O | O-Allyl |
| 2074 | 2-F, 6-Cl | O | O-Allyl |

TABLE 48

| Compound No. | $R^{12}, R^{22}, R^{32}, R^{42}, R^{52}$ | $Y^1$ | $X^1$ |
|---|---|---|---|
| 2075 | 2,3,5-Cl$_3$ | O | O-Allyl |
| 2076 | 2-Cl, 6-CH$_3$ | O | O-Allyl |
| 2077 | 2-F, 6-CH$_3$ | O | O-Allyl |
| 2078 | 2-F | O | OCH$_2$-Allyl |
| 2079 | 2-Cl | O | OCH$_2$-Allyl |
| 2080 | 2-Br | O | OCH$_2$-Allyl |
| 2081 | 2-CF$_3$ | O | OCH$_2$-Allyl |
| 2082 | 2-CH$_3$ | O | OCH$_2$-Allyl |
| 2083 | 2-OCH$_3$ | O | OCH$_2$-Allyl |
| 2084 | 2,6-F$_2$ | O | OCH$_2$-Allyl |
| 2085 | 2,6-Cl$_2$ | O | OCH$_2$-Allyl |
| 2086 | 2,6-(CH$_3$)$_2$ | O | OCH$_2$-Allyl |
| 2087 | 2-F, 6-Cl | O | OCH$_2$-Allyl |
| 2088 | 2,3,5-Cl$_3$ | O | OCH$_2$-Allyl |
| 2089 | 2-Cl, 6-CH$_3$ | O | OCH$_2$-Allyl |
| 2090 | 2-F, 6-CH$_3$ | O | OCH$_2$-Allyl |
| 2091 | 2-F | O | OCH$_2$O=CH |
| 2092 | 2-Cl | O | OCH$_2$O=CH |
| 2093 | 2-Br | O | OCH$_2$O=CH |
| 2094 | 2-CF$_3$ | O | OCH$_2$O=CH |
| 2095 | 2-CH$_3$ | O | OCH$_2$C=CH |
| 2096 | 2-OCH$_3$ | O | OCH$_2$C=CH |
| 2097 | 2,6-F$_2$ | O | OCH$_2$C=CH |
| 2098 | 2,6-Cl$_2$ | O | OCH$_2$C=CH |
| 2099 | 2,6-(CH$_3$)$_2$ | O | OCH$_2$C=CH |

TABLE 49

| Compound No. | $R^{12}, R^{22}, R^{32}, R^{42}, R^{52}$ | $Y^1$ | $X^1$ |
|---|---|---|---|
| 2100 | 2-F, 6-Cl | O | OCH$_2$C=CH |
| 2101 | 2,3,5-Cl$_3$ | O | OCH$_2$C=CH |
| 2102 | 2-Cl, 6-CH$_3$ | O | OCH$_2$C=CH |
| 2103 | 2-F, 6-CH$_3$ | O | OCH$_2$C=CH |
| 2104 | 2-F | O | OCH$_2$CH$_2$C=CH |
| 2105 | 2-Cl | O | OCH$_2$CH$_2$C=CH |
| 2106 | 2-Br | O | OCH$_2$CH$_2$C=CH |
| 2107 | 2-CF$_3$ | O | OCH$_2$CH$_2$C=CH |
| 2108 | 2-CH$_3$ | O | OCH$_2$CH$_2$C=CH |
| 2109 | 2-OCH$_3$ | O | OCH$_2$CH$_2$C=CH |
| 2110 | 2,6-F$_2$ | O | OCH$_2$CH$_2$C=CH |
| 2111 | 2,6-Cl$_2$ | O | OCH$_2$CH$_2$C=CH |
| 2112 | 2,6-(CH$_3$)$_2$ | O | OCH$_2$CH$_2$C=CH |
| 2113 | 2-F, 6-Cl | O | OCH$_2$CH$_2$C=CH |
| 2114 | 2,3,5-Cl$_3$ | O | OCH$_2$CH$_2$C=CH |
| 2115 | 2-Cl, 6-CH$_3$ | O | OCH$_2$CH$_2$C=CH |
| 2116 | 2-F, 6-CH$_3$ | O | OCH$_2$CH$_2$C=CH |
| 2117 | 2-F | O | OCH$_2$C=CCH$_3$ |
| 2118 | 2-Cl | O | OCH$_2$C=CCH$_3$ |
| 2119 | 2-Br | O | OCH$_2$C=CCH$_3$ |
| 2120 | 2-CF$_3$ | O | OCH$_2$C=CCH$_3$ |
| 2121 | 2-CH$_3$ | O | OCH$_2$C=CCH$_3$ |
| 2122 | 2-OCH$_3$ | O | OCH$_2$C=CCH$_3$ |
| 2123 | 2,6-F$_2$ | O | OCH$_2$C=CCH$_3$ |
| 2124 | 2,6-Cl$_2$ | O | OCH$_2$C=CCH$_3$ |

TABLE 50

| Compound No. | $R^{12}, R^{22}, R^{32}, R^{42}, R^{52}$ | $Y^1$ | $X^1$ |
|---|---|---|---|
| 2125 | 2,6-(CH$_3$)$_2$ | O | OCH$_2$C=CCH$_3$ |
| 2126 | 2-F, 6-Cl | O | OCH$_2$C=CCH$_3$ |
| 2127 | 2,3,5-Cl$_3$ | O | OCH$_2$C=CCH$_3$ |
| 2128 | 2-Cl, 6-CH$_3$ | O | OCH$_2$C=CCH$_3$ |
| 2129 | 2-F, 6-CH$_3$ | O | OCH$_2$C=CCH$_3$ |
| 2130 | 2-F | O | S-Me |
| 2131 | 2-Cl | O | S-Me |
| 2132 | 2-Br | O | S-Ne |
| 2133 | 2-CF$_3$ | O | S-Ne |

TABLE 50-continued

| Compound No. | $R^{12}$, $R^{22}$, $R^{32}$, $R^{42}$, $R^{52}$ | $Y^1$ | $X^1$ |
|---|---|---|---|
| 2134 | 2-CH$_3$ | O | S-Me |
| 2135 | 2-OCH$_3$ | O | S-Ne |
| 2136 | 2,6-F$_2$ | O | S-Me |
| 2137 | 2,6-Cl$_2$ | O | S-Me |
| 2138 | 2,6-(CH$_3$)$_2$ | O | S-Me |
| 2139 | 2-F, 6-Cl | O | S-Me |
| 2140 | 2,3,5-Cl$_3$ | O | S-Me |
| 2141 | 2-Cl, 6-CH$_3$ | O | S-Me |
| 2142 | 2-F, 6-CH$_3$ | O | S-Me |
| 2143 | 2-F | O | S-Et |
| 2144 | 2-Cl | O | S-Et |
| 2145 | 2-Br | O | S-Et |
| 2146 | 2-CF$_3$ | O | S-Et |
| 2147 | 2-CH$_3$ | O | S-Et |
| 2148 | 2-OCH$_3$ | O | S-Et |
| 2149 | 2,6-F$_2$ | O | S-Et |

TABLE 51

| Compound No. | $R^{12}$, $R^{22}$, $R^{32}$, $R^{42}$, $R^{52}$ | $Y^1$ | $X^1$ |
|---|---|---|---|
| 2150 | 2,6-Cl$_2$ | O | S-Et |
| 2151 | 2,6-(CH$_3$)$_2$ | O | S-Et |
| 2152 | 2-F, 6-Cl | O | S-Et |
| 2153 | 2,3,5-Cl$_3$ | O | S-Et |
| 2154 | 2-Cl, 6-CH$_3$ | O | S-Et |
| 2155 | 2-F, 6-CH$_3$ | O | S-Et |
| 2156 | 2-F | O | S-nPr |
| 2157 | 2-Cl | O | S-nPr |
| 2158 | 2-Br | O | S-nPr |
| 2159 | 2-CF$_3$ | O | S-nPr |
| 2160 | 2-CH$_3$ | O | S-nPr |
| 2161 | 2-OCH$_3$ | O | S-nPr |
| 2162 | 2,6-F$_2$ | O | S-nPr |
| 2163 | 2,6-Cl$_2$ | O | S-nPr |
| 2164 | 2,6-(CH$_3$)$_2$ | O | S-nPr |
| 2165 | 2-F, 6-Cl | O | S-nPr |
| 2166 | 2,3,5-Cl$_3$ | O | S-nPr |
| 2167 | 2-Cl, 6-CH$_3$ | O | S-nPr |
| 2168 | 2-F, 6-CH$_3$ | O | S-nPr |
| 2169 | 2-F | O | S-nBu |
| 2170 | 2-Cl | O | S-nBu |
| 2171 | 2-Br | O | S-nBu |
| 2172 | 2-CF$_3$ | O | S-nBu |
| 2173 | 2-CH$_3$ | O | S-nBu |
| 2174 | 2-OCH$_3$ | O | S-nBu |

TABLE 52

| Compound No. | $R^{12}$, $R^{22}$, $R^{32}$, $R^{42}$, $R^{52}$ | $Y^1$ | $X^1$ |
|---|---|---|---|
| 2175 | 2,6-F$_2$ | O | S-nBu |
| 2176 | 2,6-Cl$_2$ | O | S-nBu |
| 2177 | 2,6-(CH$_3$)$_2$ | O | S-nBu |
| 2178 | 2-F, 6-Cl | O | S-nBu |
| 2179 | 2,3,5-Cl$_3$ | O | S-nBu |
| 2180 | 2-Cl, 6-CH$_3$ | O | S-nBu |
| 2181 | 2-F, 6-CH$_3$ | O | S-nBu |
| 2182 | 2-F | O | S-iBu |
| 2183 | 2-Cl | O | S-iBu |
| 2184 | 2-Br | O | S-iBu |
| 2185 | 2-CF$_3$ | O | S-iBu |
| 2186 | 2-CH$_3$ | O | S-iBu |
| 2187 | 2-OCH$_3$ | O | S-iBu |
| 2188 | 2,6-F$_2$ | O | S-iBu |
| 2189 | 2,6-Cl$_2$ | O | S-iBu |
| 2190 | 2,6-(CH$_3$)$_2$ | O | S-iBu |
| 2191 | 2-F, 6-Cl | O | S-iBu |
| 2192 | 2,3,5-Cl$_3$ | O | S-iBu |

TABLE 52-continued

| Compound No. | $R^{12}$, $R^{22}$, $R^{32}$, $R^{42}$, $R^{52}$ | $Y^1$ | $X^1$ |
|---|---|---|---|
| 2193 | 2-Cl, 6-CH$_3$ | O | S-iBu |
| 2194 | 2-F, 6-CH$_3$ | O | S-iBu |
| 2195 | 2-F | O | S-Allyl |
| 2196 | 2-Cl | O | S-Allyl |
| 2197 | 2-Br | O | S-Allyl |
| 2198 | 2-CF$_3$ | O | S-Allyl |
| 2199 | 2-CH$_3$ | O | S-Allyl |

TABLE 53

| Compound No. | $R^{12}$, $R^{22}$, $R^{32}$, $R^{42}$, $R^{52}$ | $Y^1$ | $X^1$ |
|---|---|---|---|
| 2200 | 2-OCH$_3$ | O | S-Allyl |
| 2201 | 2,6-F$_2$ | O | S-Allyl |
| 2202 | 2,6-Cl$_2$ | O | S-Allyl |
| 2203 | 2,6-(CH$_3$)$_2$ | O | S-Allyl |
| 2204 | 2-F, 6-Cl | O | S-Allyl |
| 2205 | 2,3,5-Cl$_3$ | O | S-Allyl |
| 220 | 2-Cl, 6-CH$_3$ | O | S-Allyl |
| 2207 | 2-F, 6-CH$_3$ | O | S-Allyl |
| 2208 | 2-F | O | SCH$_2$-Allyl |
| 2209 | 2-Cl | O | SCH$_2$-Allyl |
| 2210 | 2-Br | O | SCH$_2$-Allyl |
| 2211 | 2-CF$_3$ | O | SCH$_2$-Allyl |
| 2212 | 2-CH$_3$ | O | SCH$_2$-Allyl |
| 2213 | 2-OCH$_3$ | O | SCH$_2$-Allyl |
| 2214 | 2,6-F$_2$ | O | SCH$_2$-Allyl |
| 2215 | 2,6-Cl$_2$ | O | SCH$_2$-Allyl |
| 2216 | 2,6-(CH$_3$)$_2$ | O | SCH$_2$-Allyl |
| 2217 | 2-F, 6-Cl | O | SCH$_2$-Allyl |
| 2218 | 2,3,5-Cl$_3$ | O | SCH$_2$-Allyl |
| 2219 | 2-Cl, 6-CH$_3$ | O | SCH$_2$-Allyl |
| 2220 | 2-F, 6-CH$_3$ | O | SCH$_2$-Allyl |
| 2221 | 2,6-Cl$_2$ | O | cPr |
| 2222 | 2-CH$_3$ | O | cPr |
| 2223 | 2,6-Cl$_2$ | O | OCH$_2$-cPr |
| 2224 | 2-CH$_3$ | O | OCH$_2$-cPr |

TABLE 54

| Compound No. | $R^{12}$, $R^{22}$, $R^{32}$, $R^{42}$, $R^{52}$ | $Y^1$ | $X^1$ |
|---|---|---|---|
| 2225 | 2,6-Cl$_2$ | O | OCH$_2$CH$_2$Cl |
| 2226 | 2-CH$_3$ | O | OCH$_2$CH$_2$Cl |
| 2227 | 2,6-Cl$_2$ | O | OCH$_2$CH$_2$Ph |
| 2228 | 2-CH$_3$ | O | OCH$_2$CH$_2$Ph |
| 2229 | 2,6-Cl$_2$ | O | OCH$_2$C(Me)=CH$_2$ |
| 2230 | 2-CH$_3$ | O | OCH$_2$C(Me)=CH$_2$ |

TABLE 55

| Compound No. | $R^{12}$, $R^{22}$, $R^{32}$, $R^{42}$, $R^{52}$ | $Y^1$ | $X^1$ |
|---|---|---|---|
| 2231 | 2-F | S | O-Me |
| 2232 | 2-Cl | S | O-Me |
| 2233 | 2-Br | S | O-Me |
| 2234 | 2-CF$_3$ | S | O-Me |
| 2235 | 2-CH$_3$ | S | O-Me |
| 2236 | 2-OCH$_3$ | S | O-Me |
| 2237 | 2,6-F$_2$ | S | O-Me |
| 2238 | 2,6-Cl$_2$ | S | O-Me |
| 2239 | 2,6-(CH$_3$)$_2$ | S | O-Me |
| 2240 | 2-F, 6-Cl | S | O-Me |
| 2241 | 2,3,5-Cl$_3$ | S | O-Me |
| 2242 | 2-Cl, 6-CH$_3$ | S | O-Me |
| 2243 | 2-F, 6-CH$_3$ | S | O-Me |

TABLE 55-continued

| Compound No. | $R^{12}, R^{22}, R^{32}, R^{42}, R^{52}$ | $Y^1$ | $X^1$ |
|---|---|---|---|
| 2244 | 2-F | S | O-Et |
| 2245 | 2-Cl | S | O-Et |
| 2246 | 2-Br | S | O-Et |
| 2247 | 2-CF$_3$ | S | O-Et |
| 2248 | 2-CH$_3$ | S | O-Et |
| 2249 | 2-OCH$_3$ | S | O-Et |
| 2250 | 2,6-F$_2$ | S | O-Et |
| 2251 | 2,6-Cl$_2$ | S | O-Et |
| 2252 | 2,6-(CH$_3$)$_2$ | S | O-Et |
| 2253 | 2-F, 6-Cl | S | O-Et |
| 2254 | 2,3,5-Cl$_3$ | S | O-Et |
| 2255 | 2-Cl, 6-CH$_3$ | S | O-Et |

TABLE 56

| Compound No. | $R^{12}, R^{22}, R^{32}, R^{42}, R^{52}$ | $Y^1$ | $X^1$ |
|---|---|---|---|
| 2256 | 2-F, 6-CH$_3$ | S | O-Et |
| 2257 | 2-F | S | O-nPr |
| 2258 | 2-Cl | S | O-nPr |
| 2259 | 2-Br | S | O-nPr |
| 2260 | 2-CF$_3$ | S | O-nPr |
| 2261 | 2-CH$_3$ | S | O-nPr |
| 2262 | 2-OCH$_3$ | S | O-nPr |
| 2263 | 2,6-F$_2$ | S | O-nPr |
| 2264 | 2,6-Cl$_2$ | S | O-nPr |
| 2265 | 2,6-(CH$_3$)$_2$ | S | O-nPr |
| 2266 | 2-F, 6-Cl | S | O-nPr |
| 2267 | 2,3,5-Cl$_3$ | S | O-nPr |
| 2268 | 2-Cl, 6-CH$_3$ | S | O-nPr |
| 2269 | 2-F, 6-CH$_3$ | S | O-nPr |
| 2270 | 2-F | S | O-nBu |
| 2271 | 2-Cl | S | O-nBu |
| 2272 | 2-Br | S | O-nBu |
| 2273 | 2-CF$_3$ | S | O-nBu |
| 2274 | 2-CH$_3$ | S | O-nBu |
| 2275 | 2-OCH$_3$ | S | O-nBu |
| 2276 | 2,6-F$_2$ | S | O-nBu |
| 2277 | 2,6-Cl$_2$ | S | O-nBu |
| 2278 | 2,6-(CH$_3$)$_2$ | S | O-nBu |
| 2279 | 2-F, 6-Cl | S | O-nBu |
| 2280 | 2,3,5-Cl$_3$ | S | O-nBu |

TABLE 57

| Compound No. | $R^{12}, R^{22}, R^{32}, R^{42}, R^{52}$ | $Y^1$ | $X^1$ |
|---|---|---|---|
| 2281 | 2-Cl, 6-CH$_3$ | S | O-nBu |
| 2282 | 2-F, 6-CH$_3$ | S | O-nBu |
| 2283 | 2-F | S | O-iBu |
| 2284 | 2-Cl | S | O-iBu |
| 2285 | 2-Br | S | O-iBu |
| 2286 | 2-CF$_3$ | S | O-iBu |
| 2287 | 2-CH$_3$ | S | O-iBu |
| 2288 | 2-OCH$_3$ | S | O-iBu |
| 2289 | 2,6-F$_2$ | S | O-iBu |
| 2290 | 2,6-Cl$_2$ | S | O-iBu |
| 2291 | 2,6-(CH$_3$)$_2$ | S | O-iBu |
| 2292 | 2-F, 6-Cl | S | O-iBu |
| 2293 | 2,3,5-Cl$_3$ | S | O-iBu |
| 2294 | 2-Cl, 6-CH$_3$ | S | O-iBu |
| 2295 | 2-F, 6-CH$_3$ | S | O-iBu |
| 2296 | 2-F | S | O-Allyl |
| 2297 | 2-Cl | S | O-Allyl |
| 2298 | 2-Br | S | O-Allyl |
| 2299 | 2-CF$_3$ | S | O-Allyl |
| 2300 | 2-CH$_3$ | S | O-Allyl |
| 2301 | 2-OCH$_3$ | S | O-Allyl |
| 2302 | 2,6-F$_2$ | S | O-Allyl |

TABLE 57-continued

| Compound No. | $R^{12}, R^{22}, R^{32}, R^{42}, R^{52}$ | $Y^1$ | $X^1$ |
|---|---|---|---|
| 2303 | 2,6-Cl$_2$ | S | O-Allyl |
| 2304 | 2,6-(CH$_3$)$_2$ | S | O-Allyl |
| 2305 | 2-F, 6-Cl | S | O-Allyl |

TABLE 58

| Compound No. | $R^{12}, R^{22}, R^{32}, R^{42}, R^{52}$ | $Y^1$ | $X^1$ |
|---|---|---|---|
| 2306 | 2,3,5-Cl$_3$ | S | O-Allyl |
| 2307 | 2-Cl, 6-CH$_3$ | S | O-Allyl |
| 2308 | 2-F, 6-CH$_3$ | S | O-Allyl |
| 2309 | 2-F | S | OCH$_2$-Allyl |
| 2310 | 2-Cl | S | OCH$_2$-Allyl |
| 2311 | 2-Br | S | OCH$_2$-Allyl |
| 2312 | 2-CF$_3$ | S | OCH$_2$-Allyl |
| 2313 | 2-CH$_3$ | S | OCH$_2$-Allyl |
| 2314 | 2-OCH$_3$ | S | OCH$_2$-Allyl |
| 2315 | 2,6-F$_2$ | S | OCH$_2$-Allyl |
| 2316 | 2,6-Cl$_2$ | S | OCH$_2$-Allyl |
| 2317 | 2,6-(CH$_3$)$_2$ | S | OCH$_2$-Allyl |
| 2318 | 2-F, 6-Cl | S | OCH$_2$-Allyl |
| 2319 | 2,3,5-Cl$_3$ | S | OCH$_2$-Allyl |
| 2320 | 2-Cl, 6-CH$_3$ | S | OCH$_2$-Allyl |
| 2321 | 2-F, 6-CH$_3$ | S | OCH$_2$-Allyl |
| 2322 | 2-F | S | OCH$_2$C≡CH |
| 2323 | 2-Cl | S | OCH$_2$C≡CH |
| 2324 | 2-Br | S | OCH$_2$C≡CH |
| 2325 | 2-CF$_3$ | S | OCH$_2$C≡CH |
| 2326 | 2-CH$_3$ | S | OCH$_2$C≡CH |
| 2327 | 2-OCH$_3$ | S | OCH$_2$C≡CH |
| 2328 | 2,6-F$_2$ | S | OCH$_2$C≡CH |
| 2329 | 2,6-Cl$_2$ | S | OCH$_2$C≡CH |
| 2330 | 2,6-(CH$_3$)$_2$ | S | OCH$_2$C≡CH |

TABLE 59

| Compound No. | $R^{12}, R^{22}, R^{32}, R^{42}, R^{52}$ | $Y^1$ | $X^1$ |
|---|---|---|---|
| 2331 | 2-F, 6-Cl | S | OCH$_2$C≡CH |
| 2332 | 2,3,5-Cl$_3$ | S | OCH$_2$C≡CH |
| 2333 | 2-Cl, 6-CH$_3$ | S | OCH$_2$C≡CH |
| 2334 | 2-F, 6-CH$_3$ | S | OCH$_2$C≡CH |
| 2335 | 2-F | S | OCH$_2$CH$_2$C≡CH |
| 2336 | 2-Cl | S | OCH$_2$CH$_2$C≡CH |
| 2337 | 2-Br | S | OCH$_2$CH$_2$C≡CH |
| 2338 | 2-CF$_3$ | S | OCH$_2$CH$_2$C≡CH |
| 2339 | 2-CH$_3$ | S | OCH$_2$CH$_2$C≡CH |
| 2340 | 2-OCH$_3$ | S | OCH$_2$CH$_2$C≡CH |
| 2341 | 2,6-F$_2$ | S | OCH$_2$CH$_2$C≡CH |
| 2342 | 2,6-Cl$_2$ | S | OCH$_2$CH$_2$C≡CH |
| 2343 | 2,6-(CH$_3$)$_2$ | S | OCH$_2$CH$_2$C≡CH |
| 2344 | 2-F, 6-Cl | S | OCH$_2$CH$_2$C≡CH |
| 2345 | 2,3,5-Cl$_3$ | S | OCH$_2$CH$_2$C≡CH |
| 2346 | 2-Cl, 6-CH$_3$ | S | OCH$_2$CH$_2$C≡CH |
| 2347 | 2-F, 6-CH$_3$ | S | OCH$_2$CH$_2$C≡CH |
| 2348 | 2-F | S | OCH$_2$C≡CCH$_3$ |
| 2349 | 2-Cl | S | OCH$_2$C≡CCH$_3$ |
| 2350 | 2-Br | S | OCH$_2$C≡CCH$_3$ |
| 2351 | 2-CF$_3$ | S | OCH$_2$C≡CCH$_3$ |
| 2352 | 2-CH$_3$ | S | OCH$_2$C≡CCH$_3$ |
| 2353 | 2-OCH$_3$ | S | OCH$_2$C≡CCH$_3$ |
| 2354 | 2,6-F$_2$ | S | OCH$_2$C≡CCH$_3$ |
| 2355 | 2,6-Cl$_2$ | S | OCH$_2$C≡CCH$_3$ |

TABLE 60

| Compound No. | $R^{12}, R^{22}, R^{32}, R^{42}, R^{52}$ | $Y^1$ | $X^1$ |
|---|---|---|---|
| 2356 | 2,6-(CH$_3$)$_2$ | S | OCH$_2$C≡CCH$_3$ |
| 2357 | 2-F, 6-Cl | S | OCH$_2$C≡CCH$_3$ |
| 2358 | 2,3,5-Cl$_3$ | S | OCH$_2$C≡CCH$_3$ |
| 2359 | 2-Cl, 6-CH$_3$ | S | OCH$_2$C≡CCH$_3$ |
| 2360 | 2-F, 6-CH$_3$ | S | OCH$_2$C≡CCH$_3$ |
| 2361 | 2,6-Cl$_2$ | S | cPr |
| 2362 | 2-CH$_3$ | S | cPr |
| 2363 | 2,6-Cl$_2$ | S | OCH$_2$-cPr |
| 2364 | 2-CH$_3$ | S | OCH$_2$-cPr |
| 2365 | 2,6-Cl$_2$ | S | OCH$_2$CH$_2$Cl |
| 2366 | 2-CH$_3$ | S | OCH$_2$CH$_2$Cl |
| 2367 | 2,6-Cl$_2$ | S | OCH$_2$CH$_2$Ph |
| 2368 | 2-CH$_3$ | S | OCH$_2$CH$_2$Ph |
| 2369 | 2,6-Cl$_2$ | S | OCH$_2$C(Me)=CH$_2$ |
| 2370 | 2-CH$_3$ | S | OCH$_2$C(Me)=CH$_2$ |
| 2371 | 2-F | O | Me |
| 2372 | 2-Cl | O | Me |
| 2373 | 2-Br | O | Me |
| 2374 | 2-CF$_3$ | O | Me |
| 2375 | 2-CH$_3$ | O | Me |
| 2376 | 2-OCH$_3$ | O | Me |
| 2377 | 2,6-F$_2$ | O | Me |
| 2378 | 2,6-Cl$_2$ | O | Me |
| 2379 | 2,6-(CH$_3$)$_2$ | O | Me |
| 2380 | 2-F, 6-Cl | O | Me |

TABLE 61

| Compound No. | $R^{12}, R^{22}, R^{32}, R^{42}, R^{52}$ | $Y^1$ | $X^1$ |
|---|---|---|---|
| 2381 | 2,3,5-Cl$_3$ | O | Me |
| 2382 | 2-Cl, 6-CH$_3$ | O | Me |
| 2383 | 2-F, 6-CH$_3$ | O | Me |
| 2384 | 2-F | O | Et |
| 2385 | 2-Cl | O | Et |
| 2386 | 2-Br | O | Et |
| 2387 | 2-CF$_3$ | O | Et |
| 2388 | 2-CH$_3$ | O | Et |
| 2389 | 2-OCH$_3$ | O | Et |
| 2390 | 2,6-F$_2$ | O | Et |
| 2391 | 2,6-Cl$_2$ | O | Et |
| 2392 | 2,6-(CH$_3$)$_2$ | O | Et |
| 2393 | 2-F, 6-Cl | O | Et |
| 2394 | 2,3,5-Cl$_3$ | O | Et |
| 2395 | 2-Cl, 6-CH$_3$ | O | Et |
| 2396 | 2-F, 6-CH$_3$ | O | Et |
| 2397 | 2-F | O | nPr |
| 2398 | 2-Cl | O | nPr |
| 2399 | 2-Br | O | nPr |
| 2400 | 2-CF$_3$ | O | nPr |
| 2401 | 2-CH$_3$ | O | nPr |
| 2402 | 2-OCH$_3$ | O | nPr |
| 2403 | 2,6-F$_2$ | O | nPr |
| 2404 | 2,6-Cl$_2$ | O | nPr |
| 2405 | 2,6-(CH$_3$)$_2$ | O | nPr |

TABLE 62

| Compound No. | $R^{12}, R^{22}, R^{32}, R^{42}, R^{52}$ | $Y^1$ | $X^1$ |
|---|---|---|---|
| 2406 | 2-F, 6-Cl | O | nPr |
| 2407 | 2,3,5-Cl$_3$ | O | nPr |
| 2408 | 2-Cl, 6-CH$_3$ | O | nPr |
| 2409 | 2-F, 6-CH$_3$ | O | nPr |
| 2410 | 2-F | O | nBu |
| 2411 | 2-Cl | O | nBu |
| 2412 | 2-Br | O | nBu |
| 2413 | 2-CF$_3$ | O | nBu |
| 2414 | 2-CH$_3$ | O | nBu |
| 2415 | 2-OCH$_3$ | O | nBu |

TABLE 62-continued

| Compound No. | $R^{12}, R^{22}, R^{32}, R^{42}, R^{52}$ | $Y^1$ | $X^1$ |
|---|---|---|---|
| 2416 | 2,6-F$_2$ | O | nBu |
| 2417 | 2,6-Cl$_2$ | O | nBu |
| 2418 | 2,6-(CH$_3$)$_2$ | O | nBu |
| 2419 | 2-F, 6-Cl | O | nBu |
| 2420 | 2,3,5-Cl$_3$ | O | nBu |
| 2421 | 2-Cl, 6-CH$_3$ | O | nBu |
| 2422 | 2-F, 6-CH$_3$ | O | nBu |
| 2423 | 2-F | O | nPen |
| 2424 | 2-Cl | O | nPen |
| 2425 | 2-Br | O | nPen |
| 2426 | 2-CF$_3$ | O | nPen |
| 2427 | 2-CH$_3$ | O | nPen |
| 2428 | 2-OCH$_3$ | O | nPen |
| 2429 | 2,6-F$_2$ | O | nPen |
| 2430 | 2,6-Cl$_2$ | O | nPen |

The compounds represented by the formula:

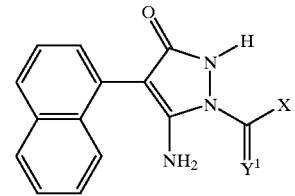

TABLE 63

| Compound No. | $R^{12}, R^{22}, R^{32}, R^{42}, R^{52}$ | $Y^1$ | $X^1$ |
|---|---|---|---|
| 2431 | 2,6-(CH$_3$)$_2$ | O | nPen |
| 2432 | 2-F, 6-Cl | O | nPen |
| 2433 | 2,3,5-Cl$_3$ | O | nPen |
| 2435 | 2-Cl, 6-CH$_3$ | O | nPen |

TABLE 64

| Compound No. | $Y^1$ | $X^1$ |
|---|---|---|
| 2436 | O | Me |
| 2437 | O | Et |
| 2438 | O | nPr |
| 2439 | O | nBu |
| 2440 | O | nPen |
| 2441 | O | cPr |
| 2442 | O | CH$_2$Ph |
| 2443 | O | O-Me |
| 2444 | O | O-Et |
| 2445 | O | O-nPr |
| 2446 | O | O-nBu |
| 2447 | O | O-iBu |
| 2448 | O | O-Allyl |
| 2449 | O | OCH$_2$C≡CH |
| 2450 | O | OCH$_2$CH$_2$C≡CH |
| 2451 | O | OCH$_2$C≡CCH$_3$ |
| 2452 | O | O-Me |
| 2453 | O | O-Et |
| 2454 | O | O-nPr |
| 2455 | O | O-nBu |
| 2456 | O | O-iBu |
| 2457 | O | O-Allyl |
| 2458 | O | OCH$_2$C≡CH |
| 2459 | O | OCH$_2$CH$_2$C≡CH |
| 2560 | O | OCH$_2$C≡CCH$_3$ |

[In the above Tables 1 to 64, Me stands for methyl group, Et for ethyl group, nPr for normal propyl group, iPr for isopropyl group, cPr for cyclopropyl group, nBu for normal butyl group, sBu for secondary butyl group, iBu for isobutyl group, nPen for normal pentyl group, Allyl for 2-propenyl group, and Ph for phenyl group. In case a compound contains an asymmetric carbon atom(s), it includes one of the optical active compounds and their mixtures.]

Melting points of some of the compounds of the present invention are shown below.

Compound 18: 170.3° C.
Compound 31: 160.2° C.
Compound 164: 168.7° C.
Compound 177: 142.3° C.
Compound 281: 150.6° C.
Compound 291: 92.9° C.
Compound 294: 163.3° C.
Compound 327: 111.2° C.
Compound 590: 146.7° C.
Compound 333: 150.9° C.
Compound 359: 132.7° C.
Compound 372: 121.1° C.
Compound 385: 143.7° C.
Compound 586: 148.2° C.
Compound 587: 89.8° C.

$^1$H-NMR (CDCl$_3$, TMS) data of some of the present compound are shown below.

Compound 87: 7.15–7.3 (4H), 5.8 (2H), 3.35 (1H), 2.8 (2H), 2.27 (3H), 1.8–2.2 (2H, 1.36 (3H), 1.24 (3H), 1.01 (3H)

Compound 278: 7.16–7.24 (4H), 5.5 (2H, 4.41 (2H), 3.8 (1H), 2.27 (3H), 2.1 (1H, 1.7 (1H), 1.43 (3H), 1.32 (3H), 1.00 (3H)

Compound 878: 7.8–7.9 (3H), 7.46–7.50 (4H), 5.68 (2H), 4.43 (2H), 4.13 (1H), 1.47 (9H)

$^1$H-NMR (CDCl$_3$, TMS) data of some of the intermediates A are shown below.

Compound 1014: 7.23–7.46 (4H), 4.86 (2H), 4.15 (1H), 1.55–1.8 (2H), 1.22 (3H), 0.91 (3H) Compound 1020: 7.4 (1H), 7.2–7.3 (2H), 4.83 (2H), 4.15 (1H), 1.55–1.8 (2H), 1.23 (3H), 0.92 (3H)

Compound 1026: 7.80–7.86 (3H), 7.42–7.50 (4H), 4.83 (2H), 4.43 (1H), 1.29 (6H)

Formulation examples of the present compounds are shown below. In the following descriptions of Formulation examples, all "parts" are by weight unless otherwise noted, and the present compounds are indicated by the Compound numbers shown in Tables 1 to 40.

Formulation Example 1

50 parts each of the Compounds 1 to 940, 3 parts of calcium lignin sulfonate, 2 parts of sodium lauryl sulfate and 45 parts of synthetic hydrous silicon oxide were ground and mixed well to obtain wettable powders.

Formulation Example 2

25 parts each of the Compounds 1 to 940, 3 parts of polyoxyethylene sorbitan monooleate, 3 parts of CMC and 69 parts of wet were mixed and water-ground until the particle size of the active ingredient became less than 5 microns to obtain flowables.

Formulation Example 3

2 parts each of the Compounds 1 to 940, 88 parts of kaolin clay and 10 parts of talc were ground and mixed well to obtain powders.

Formulation Example 4

2 parts each of the Compounds 1 to 940, one part of synthetic hydrous silicon oxide, 2 parts of calcium lignin sulfonate, 30 parts of bentonite and 65 parts of kaolin clay were ground and mixed well, and the mixture was kneaded well by adding water, then granulated and dried to obtain granules.

Formulation Example 5

20 parts each of the Compounds 1 to 940 and 1.5 part of sorbitan trioleate were mixed with 28.5 parts of an aqueous solution containing 2 parts of polyvinyl alcohol, and the mixture was finely ground (to a particle size of less than 3 microns) by a sand grinder. To this ground mixture was added 40 parts of an aqueous solution containing 0.05 part of xanthane gum and 0.1 part of aluminum magnesium silicate, followed by further addition of 10 parts of propylene glycol and mixing by stirring to obtain 20% water suspensions.

Usefulness of the present compounds as a plant disease controlling agent is illustrated by a Test Example. The present compounds used are indicated by the Compound numbers shown in Tables 1 to 40.

The controlling effect of the present compounds against plant diseases was determined by observing with the naked eye the areal ratio of the morbid spots on the test plants at the time of examination and comparing the total area of spots in the no-treatment (control) section with that in the compound-treated section.

Test Example: Test of Controlling Effect (Prophylactic Effect) Against *Botrytis cinerea* of Cucumber Seeds of cucumber (variety: *Sagami hanpaku*) were sown in the plastic pots packed with sandy loam and let sprout and grow in a hothouse for 12 days. Wettable powders were prepared with the Compounds 18, 31, 87, 151, 164, 177, 190, 203, 216, 229, 242, 255, 278, 281, 294, 327, 330, 333, 346, 356, 359, 372, 385, 408, 411, 463, 499, (+)-499, (−)-499, 502, (+)-502, (−)-502, 551, 574, 578, 582, 595 and 621 according to the method of Formulation Example 1, and each of these wettable powders was diluted with water to a prescribed concentration (200 ppm). Each of the thus prepared solutions was sprayed to the stalks and leaves of cucumber so that the solution would adhere sufficiently to the leave surfaces. The sprayed plants were air-dried, and a PDA medium containing hyphae of the fungi of *Botrytis cinerea* of cucumber was placed on the cucumber leave surfaces. The test plastic pots were placed under a humid environment of 10° C. for 4 days, and then the controlling effect of the compounds against *Botrytis cinerea* of cucumber was examined. The result showed that the morbid spot area on the plants in the compound-treated section was less than 10% of that on the plants in the non-treatment section.

EFFECT OF THE INVENTION

The compounds of the present invention have excellent controlling effect against plant diseases.

What is claimed is:
1. The pyrazolinone derivatives represented by the formula [I]:

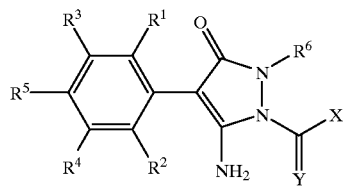

wherein $R^1$, $R^2$, $R^3$, $R^4$ and $R^5$ may be identical or different and represent independently a hydrogen atom, a halogen atom, an alkyl group, a haloalkyl group, an alkoxyl group, an alkoxyalkyl group, an alkoxyalkoxyl group, a haloalkoxyl group, an alkylthio group, a haloalkylthio group, a cyano group, a nitro group, an optionally substituted phenyl group or an optionally substituted phenoxyl group, or adjacent two of $R^1$, $R^2$, $R^3$, $R^4$ and $R^5$ are combined at the ends to represent a group of the formula CH=CH—CH=CH, a methylenedioxy group which may be substituted with a halogen atom or an alkylene group which may contain one oxygen atom and may be substituted with an alkyl group;

$R^6$ represents an optionally substituted alkyl group, an optionally substituted alkenyl group, an optionally substituted alkynyl group, an optionally substituted phenyl group or an optionally substituted alicyclic hydrocarbon group;

X represents an optionally substituted alkyl group, an optionally substituted alkenyl group, an optionally substituted alkynyl group, an optionally substituted phenyl group, an optionally substituted alkoxyl group, an optionally substituted alkenyloxy group, an optionally substituted alkynyloxy group, an optionally substituted phenoxyl group, an optionally substituted alkylthio group, an optionally substituted alkenylthio group, an optionally substituted alkynylthio group, an optionally substituted phenylthio group or an optionally substituted alicyclic hydrocarbon group; and Y represents an oxygen atom or a sulfur atom.

2. The pyrazolinone derivatives according to claim 1, wherein in the formula [I], $R^1$, $R^2$, $R^3$, $R^4$ and $R^5$ are identical or different and represent independently a hydrogen atom, a halogen atom, a C1–C5 alkyl group, a C1–C5 haloalkyl group, a C1–C5 alkoxyl group, a C1–C3 alkoxy C1–C3 alkyl group, a C1–C3 alkoxy C1–C3 alkoxyl group, a C1–C5 haloalkoxyl group, a C1–C5 alkylthio group, a C1–C5 haloalkylthio group, a cyano group, a nitro group, or a phenyl or phenoxyl group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano groups, or adjacent two of $R^1$, $R^2$, $R^3$, $R^4$ and $R^5$ are combined at the ends to represent a group of the formula CH=CH—CH=CH, a methylenedioxy group which may be substituted with a halogen atom, a trimethylene group, a tetramethylene group, a group represented by the formula OCH$_2$CH$_2$ or a group represented by the formula OCH$_2$CH (CH$_3$);

$R^6$ represents a C1–C10 alkyl group, a C3–C10 alkenyl group, a C3–C10 alkynyl group, a C1–C10 haloalkyl group, a C3–C10 haloalkenyl group, a C3–C10 haloalkynyl group, a C1–C5 alkoxy C1–C5 alkyl group, a C1–C5 alkylthio C1–C5 alkyl group, a C1–C5 haloalkoxy C1–C5 alkyl group, a C1–C5 haloalkoxy C1–C5 haloalkyl group, a C1–C5 haloalkylthio C1–C5 alkyl group, a C1–C5 haloalkylthio C1–C5 haloalkyl group, a cyano C1–C5 alkyl group, a cyano C1–C5 haloalkyl group, a C1–C5 alkoxycarbonyl C1–C5 alkyl group, a C3–C8 alicyclic hydrocarbon group which may be substituted with a halogen atom and may contain unsaturated bonds, a C1–C5 alkyl group substituted with a C3–C8 alicyclic hydrocarbon group which may be substituted with a halogen atom and may contain unsaturated bonds, a phenyl or C7–C17 aralkyl group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano groups;

X represents a C1–C10 alkyl group, a C2–C10 alkenyl group, a C2–C10 alkynyl group, a C1–C10 haloalkyl group, a C2–C10 haloalkynyl group, a C2–C10 haloalkenyl group, a C1–C5 alkoxy C1–C5 alkyl group, a C1–C5 alkylthio C1–C5 alkyl group, a C1–C5 haloalkoxy C1–C5 alkyl group, a C1–C5 haloalkoxy C1–C5 haloalkyl group, a C1–C5 haloalkylthio C1–C5 alkyl group, a C1–C5 haloalkylthio C1–C5 haloalkyl group, a cyano C1–C5 alkyl group, a cyano C1–C5 haloalkyl group, a C1–C5 alkyl group substituted with a C1–C5 alkoxycarbonyl group, a C1–C5 alkyl group substituted with a C3–C8 alicyclic hydrocarbon group which may be substituted with a halogen atom and may contain unsaturated bonds, a C1–C10 alkoxyl group, a C2–C10 alkenyloxy group, a C2–C10 alkynyloxy group, a C1–C10 haloalkoxyl group, a C2–C10 haloalkenyloxy group, a C2–C10 haloalkynyloxy group, C1–C5 alkoxy C1–C5 alkoxyl group, a C1–C5 alkylthio C1–C5 alkoxyl group, a C1–C5 haloalkoxy C1–C5 alkoxyl group, a C1–C5 haloalkoxy C1–C5 haloalkoxyl group, a C1–C5 haloalkylthio C1–C5 alkoxyl group, a C1–C5 haloalkylthio C1–C5 haloalkoxyl group, a cyano C1–C5 alkoxyl group, a C1–C5 alkoxycarbonyl C1–C5 alkoxyl group, a C1–C5 alkoxyl group substituted with a C3–C8 alicyclic hydrocarbon group which may be substituted with a halogen atom and may contain unsaturated bonds, a phenyl group, C7–C17 aralkyl group, phenoxyl group, C7–C17 aralkyloxy group, phenylthio group or C7–C17 aralkylthio group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxy C1–C5 haloalkylthio groups and cyano groups, a C1–C10 alkylthio group, a C2–C10 alkenylthio group, a C2–C10 alkynylthio group, a C1–C10 haloalkylthio group, a C2–C10 haloalkynylthio group, a C2–C10 haloalkenylthio group, a C1–C5 alkoxy C1–C5 alkylthio group, a C1–C5 alkylthio C1–C5 alkylthio group, a C1–C5 haloalkoxy C1–C5 alkylthio group, a C1–C5 haloalkoxy C1–C5 haloalkylthio group, a C1–C5 haloalkylthio C1–C5 alkylthio group, a C1–C5 haloalkylthio C1–C5 haloalkylthio group, a cyano C1–C5 alkylthio group, a C1–C5 alkoxycarbonyl C1–C5 alkylthio group, a C1–C5 alkylthio group substituted with a C3–C8 alicyclic hydrocarbon group which may be substituted with a halogen atom and may contain unsaturated bonds, or a C3–C8 alicyclic hydrocarbon group which may be substituted with a halogen atom and may contain unsaturated bonds.

3. The pyrazolinone derivatives according to claim 1 or 2, wherein in the formula [I], $R^1$, $R^2$, $R^3$, $R^4$ and $R^5$ are identical or different and represent independently a hydrogen atom, a halogen atom, a C1–C5 alkyl group, a C1–C5 haloalkyl group or a C1–C5 alkoxyl group, or adjacent two of $R^1$, $R^2$, $R^3$, $R^4$ and $R^5$ are combined at the ends to represent a group of the formula CH=CH—CH=CH.

4. The pyrazolinone derivatives according to claim 1 or 2, wherein in the formula [I], $R^3$, $R^4$ and $R^5$ are a hydrogen atom.

5. The pyrazolinone derivatives according to claim 1 or 2, wherein in the formula [I], $R^1$ is a halogen atom or a methyl group which may be substituted with a halogen atom, and $R^2$ is a hydrogen atom, a halogen atom or a methyl group which may be substituted with a halogen atom.

6. The pyrazolinone derivatives according to claim 1 or 2, wherein in the formula [I], $R^6$ is a C1–C10 alkyl group, a C3–C10 alkenyl group, a C3–C10 alkynyl group, a C1–C10 haloalkyl group, a C3–C10 haloalkenyl group, a C3–C10 haloalkynyl group, a C3–C8 alicyclic hydrocarbon group which may be substituted with a halogen atom and may contain unsaturated bonds, or a C1–C5 alkyl group substituted with a C3–C8 alicyclic hydrocarbon group which may be substituted with a halogen atom and may contain unsaturated bonds.

7. The pyrazolinone derivatives according to claim 1 or 2, wherein in the formula [I], X is a C1–C10 alkyl group, a C2–C10 alkenyl group, a C2–C10 alkynyl group, a C1–C10 haloalkyl group, a C2–C10 haloalkenyl group, a C2–C10 haloalkynyl group, a phenyl group, phenoxyl group or phenylthio group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxyl groups, a C1–C5 haloalkylthio groups and cyano groups, a C1–C10 alkoxyl group, a C2–C10 alkenyloxy group, a C2–C10 alkynyloxy group, a C1–C10 haloalkoxyl group, C2–C10 haloalkenyloxy group, a C2–C10 haloalkynyloxy group, a C1–C10 alkylthio group, a C2–C10 alkenylthio group, a C2–C10 alkynylthio group, a C1–C10 haloalkylthio group, a C2–C10 haloalkenylthio group or a C2–C10 haloalkynylthio group, or a C3–C8 alicyclic hydrocarbon group which may be substituted with a halogen atom or may contain unsaturated bonds.

8. The pyrazolinone derivatives according to claim 1 or 2, wherein in the formula [I], X is a methylthio group, an ethylthio group, a propylthio group or a 2-propenylthio group.

9. The pyrazolinone derivatives according to claim 1 or 2, wherein in the formula [I], $R^6$ is an isopropyl group, a 1-methylbutyl group or a sec-butyl group.

10. The pyrazolinone derivatives according to claim 1 or 2, wherein in the formula [I], Y is an oxygen atom.

11. A plant disease controlling agent characterized in that it contains a pyrazolinone derivative set forth in claim 1 or 2 as an active ingredient.

12. The pyrazolinone compounds represented by the formula [II]:

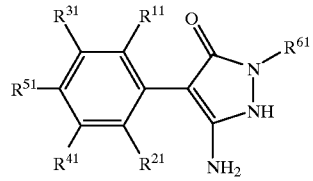

wherein $R^{11}$ and $R^{21}$ may be identical or different and represent independently a hydrogen atom, a halogen atom, an alkyl group, a haloalkyl group, an alkoxyl group, an alkoxyalkyl group, an alkoxyalkoxyl group, a haloalkoxyl group, an alkylthio group, a haloalkylthio group, a cyano group, a nitro group, an optionally substituted phenyl group or an optionally substituted phenoxyl group, $R^{31}$, $R^{41}$ and $R^{51}$ represent a hydrogen atom, $R^{61}$ represents an optionally substituted alkyl group, an optionally substituted alkenyl group, an optionally substituted alkynyl group or an optionally substituted alicyclic hydrocarbon group.

13. The pyrazolinone compounds according to claim 12, wherein in the formula [II], $R^{11}$ and $R^{21}$ are identical or different and represent independently a hydrogen atom, a halogen atom, a C1–C5 alkyl group, a C1–C5 haloalkyl group, a C1–C5 alkoxyl group, a C1–C3 alkoxy C1–C3 alkyl group, a C1–C3 alkoxy C1–C3 alkoxyl group, a C1–C5 haloalkoxyl group, a C1–C5 alkylthio group, a C1–C5 haloalkylthio group, a cyano group, a nitro group, a phenyl group or phenoxyl group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano groups, $R^{61}$ is a C1–C10 alkyl group, a C3–C10 alkenyl group, a C3–C10 alkynyl group, a C1–C10 haloalkyl group, a C3–C10 haloalkenyl group, a C3–C10 haloalkynyl group, a C1–C5 alkoxy C1–C5 alkyl group, a C1–C5 alkylthio C1–C5 alkyl group, a C1–C5 haloalkoxy C1–C5 alkyl group, a C1–C5 haloalkoxy C1–C5 haloalkyl group, a C1–C5 haloalkylthio C1–C5 alkyl group, a C1–C5 haloalkylthio C1–C5 haloalkyl group, a cyano C1–C5 alkyl group, a cyano C1–C5 haloalkyl group, a C1–C5 alkoxycarbonyl C1–C5 alkyl group, a C3–C8 alicyclic hydrocarbon group which may be substituted with a halogen atom and may contain unsaturated bonds, a C1–C5 alkyl group substituted with a C3–C8 alicyclic hydrocarbon group which may be substituted with a halogen atom and may contain unsaturated bonds, or a C7–C17 aralkyl group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano groups.

14. The pyrazolinone compounds according to claim 12 or 13, wherein in the formula [II], $R^{11}$ and $R^{21}$ are identical or different and represent independently a hydrogen atom, a halogen atom, a C1–C5 alkyl group, a C1–C5 haloalkyl group or a C1–C5 alkoxyl group.

15. The pyrazolinone compounds according to claim 12 or 13, wherein in the formula [II], $R^{11}$ is a halogen atom or a methyl group which may be substituted with a halogen atom, and $R^{21}$ is a hydrogen atom, a halogen atom or a methyl group which may be substituted with a halogen atom.

16. The pyrazolinone compounds according to claim 12 or 13, wherein in the formula [II], $R^{61}$ is an isopropyl group, a 1-methylbutyl group or a sec-butyl group.

17. The pyrazolinone compounds represented by the formula [III]:

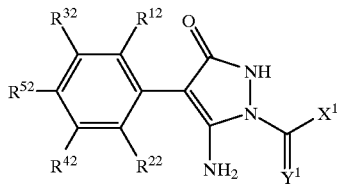

wherein $R^{12}$, $R^{22}$, $R^{32}$, $R^{42}$ and $R^{52}$ may be identical or different and represent independently a hydrogen atom, a halogen atom, an alkyl group, a haloalkyl group, an alkoxyl group, an alkoxyalkyl group, an alkoxyalkoxyl group, a haloalkoxyl group, an alkylthio group, a haloalkylthio group, a cyano group, a nitro group, an optionally substituted phenyl group or an optionally substituted phenoxyl group, or adjacent two of $R^{12}$, $R^{22}$, $R^{32}$, $R^{42}$ and $R^{52}$ are combined at the ends to represent a group of the formula CH=CH—CH=CH, a methylenedioxy group which may be substituted with a halogen atom or an alkylene group which may contain one oxygen atom and may be substituted with an alkyl group;

$X^1$ represents an optionally substituted alkyl group, an optionally substituted alkenyl group, an optionally substituted alkynyl group, an optionally substituted phenyl group, an optionally substituted alkoxyl group, an optionally substituted alkenyloxy group, an optionally substituted alkynyloxy group, an optionally substituted phenoxyl group, an optionally substituted alkylthio group, an optionally substituted alkenylthio group, an optionally substituted alkynylthio group, an optionally substituted phenylthio group or an optionally substituted alicyclic hydrocarbon group; and $Y^1$ represents an oxygen atom or a sulfur atom.

18. The pyrazolinone compounds according to claim 17, wherein in the formula [III], $R^{12}$, $R^{22}$, $R^{32}$, $R^{42}$ and $R^{52}$ are identical or different and represent independently a hydrogen atom, a halogen atom, a C1–C5 alkyl group, a C1–C5 haloalkyl group, a C1–C5 alkoxyl group, a C1–C3 alkoxy C1–C3 alkyl group, a C1–C3 alkoxy C1–C3 alkoxyl group, a C1–C5 haloalkoxyl group, a C1–C5 alkylthio group, C1–C5 haloalkylthio group, a cyano group, a nitro group or a phenyl or phenoxyl group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano groups, or adjacent two of $R^{12}$, $R^{22}$, $R^{32}$, $R^{42}$ and $R^{52}$ are combined at the ends to represent a group of the formula CH=CH—CH=CH, a methylenedioxy group (which may be substituted with a halogen atom), a trimethylene group, a tetramethylene group, a group represented by the formula $OCH_2CH_2$ or a group represented by the formula $OCH_2CH(CH_3)$; and $X^1$ represents a C1–C10 alkyl group, a C2–C10 alkenyl group, a C2–C10 alkynyl group, a C1–C10 haloalkyl group, a C2–C10 haloalkenyl group, a C2–C10 haloalknyl group, a C1–C5 alkoxy C1–C5 alkyl group, a C1–C5 alkylthio C1–C5 alkyl group, a C1–C5 haloalkoxy C1–C5 alkyl group, a C1–C5 haloalkoxy C1–C5 haloalkyl group, a C1–C5 haloalkylthio C1–C5 alkyl group, a C1–C5 haloalkylthio C1–C5 haloalkyl group, a cyano C1–C5 alkyl group, a cyano C1–C5 haloalkyl group, a C1–C5 alkyl group substituted with a C1–C5 alkoxycarbonyl group, a C1–C5 alkyl group substituted with a C3–C8 alicyclic hydrocarbon group which may be substituted with a halogen atom and may contain unsaturated bonds, a phenyl, C7–C17 aralkyl, phenoxyl, C7–C17 aralkyloxy, phenylthio or C7–C17 aralkylthio group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano groups, a C1–C10 alkoxyl group, a C2–C10 alkenyloxy group, a C2–C10 alkynyloxy group, a C1–C10 haloalkoxyl group, a C2–C10 haloalkenyloxy group, a C2–C10 haloalkynyloxy group, a C1–C5 alkoxy C1–C5 alkoxyl group, a C1–C5 alkylthio C1–C5 alkoxyl group, a C1–C5 haloalkoxy C1–C5 alkoxyl group, a C1–C5 haloalkoxy C1–C5 haloalkoxyl group, a C1–C5 haloalkylthio C1–C5 alkoxyl group, a C1–C5 haloalkylthio C1–C5 haloalkoxyl group, a cyano C1–C5 alkoxyl group, a C1–C5 alkoxycarbonyl C1–C5 alkoxyl group, a C1–C5 alkoxyl or C1–C5 alkylthio group substituted with a C3–C8 alicyclic hydrocarbon group which may be substituted with a halogen atom and may contain unsaturated bonds, a C1–C10 alkylthio group, a C2–C10 alkenylthio group, a C2–C10 alkynylthio group, a C1–C10 haloalkylthio group, a C2–C10 haloalkenylthio group, a C2–C10 haloalkynylthio group, a C1–C5 alkoxy C1–C5 alkylthio group, a C1–C5 alkylthio C1–C5 alkylthio group, a C1–C5 haloalkoxy C1–C5 alkylthio group, a C1–C5 haloalkoxy C1–C5 haloalkylthio group, a C1–C5 haloalkylthio C1–C5 alkylthio group, a C1–C5 haloalkylthio C1–C5 haloalkylthio group, a cyano C1–C5 alkylthio group, a C1–C5 alkoxycarbonyl C1–C5 alkylthio group or a C3–C8 alicyclic hydrocarbon group which may be substituted with a halogen atom and may contain unsaturated bonds.

19. The pyrazolinone compounds according to claim 17 or 18, wherein in the formula [III], $R^{12}$, $R^{22}$, $R^{32}$, $R^{42}$ and $R^{52}$ are identical or different and represent independently a hydrogen atom, a halogen atom, a C1–C5 alkyl group, a C1–C5 haloalkyl group or a C1–C5 alkoxyl group, or adjacent two of $R^{12}$, $R^{22}$, $R^{32}$, $R^{42}$ and $R^{52}$ are combined at the ends to represent a group of the formula CH=CH—CH=CH.

20. The pyrazolinone compounds according to claim 17 or 18, wherein in the formula [III], $R^{32}$, $R^{42}$ and $R^{52}$ are a hydrogen atom.

21. The pyrazolinone compounds according to claim 17 or 18, wherein in the formula [III], $R^{12}$ is a halogen atom or a methyl group which may be substituted with a halogen atom, and $R^{22}$ is a hydrogen atom, a halogen atom or a methyl group which may be substituted with a halogen atom.

22. The pyrazolinone compounds according to claim 17 or 18, wherein in the formula [III], $X^1$ is a C1–C10 alkyl group, a C2–C10 alkenyl group, a C2–C10 alkynyl group, a C1–C10 haloalkyl group, a C2–C10 haloalkenyl group, a C2–C10 haloalkynyl group, a C1–C10 alkoxyl group, a C1–C10 haloalkoxyl group, a C2–C10 alkenyloxy group, a C2–C10 haloalkenyloxy group, a C2–C10 alkynyloxy group, a C2–C10 haloalkynyloxy group, a phenyl, phenoxyl or phenylthio group which may be substituted with at least one group selected from the group consisting of halogen atoms, C1–C5 alkyl groups, C1–C5 alkoxyl groups, C1–C5 alkylthio groups, C1–C5 haloalkyl groups, C1–C5 haloalkoxyl groups, C1–C5 haloalkylthio groups and cyano groups, a C1–C10 alkylthio group, a C2–C10 alkenylthio group, a C2–C10 alkynylthio group, a C1–C10 haloalkylthio group, a C2–C10 haloalkenylthio group, C2–C10 haloalkynylthio group or a C3–C8 alicyclic hydrocarbon group which may be substituted with a halogen atom and may contain unsaturated bonds.

23. The pyrazolinone compounds according to claim 17, or 18, wherein in the formula [III], $X^1$ is a methylthio group, an ethylthio group, a propylthio group or a 2-propenylthio group.

24. The pyrazolinone compounds according to claim 17, or 18, wherein in the formula [III], $Y^1$ is an oxygen atom.

25. A method for controlling plant diseases which comprises applying a pyrazolinone derivative of the formula [I] set forth in claim 1 as an active ingredient to a place where the germs of plant diseases propagate.

* * * * *